US007894993B2

(12) United States Patent
Jung et al.

(10) Patent No.: US 7,894,993 B2
(45) Date of Patent: *Feb. 22, 2011

(54) DATA ACCESSING TECHNIQUES RELATED TO TISSUE CODING

(75) Inventors: Edward K. Y. Jung, Bellevue, WA (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Livermore, CA (US)

(73) Assignee: The Invention Science Fund I, LLC

( * ) Notice: Subject to any disclaimer, the term of this patent is extended or adjusted under 35 U.S.C. 154(b) by 1195 days.

This patent is subject to a terminal disclaimer.

(21) Appl. No.: 11/343,965

(22) Filed: Jan. 31, 2006

(65) Prior Publication Data

US 2007/0055454 A1    Mar. 8, 2007

Related U.S. Application Data

(63) Continuation-in-part of application No. 11/314,730, filed on Dec. 21, 2005, and a continuation-in-part of application No. 11/311,906, filed on Dec. 19, 2005, and a continuation-in-part of application No. 11/286,133, filed on Nov. 23, 2005, and a continuation-in-part of application No. 11/262,499, filed on Oct. 28, 2005, and a continuation-in-part of application No. 11/241,868, filed on Sep. 30, 2005, and a continuation-in-part of application No. 11/222,031, filed on Sep. 8, 2005.

(51) Int. Cl.
*G06F 19/00* (2006.01)
*G06G 7/58* (2006.01)
*G06G 7/00* (2006.01)

(52) U.S. Cl. .............................. 702/19; 706/21; 703/11

(58) Field of Classification Search ........................ None
See application file for complete search history.

(56) References Cited

U.S. PATENT DOCUMENTS

| 5,953,704 | A | 9/1999 | McIlroy et al. |
| 6,615,209 | B1 | 9/2003 | Gomes et al. |
| 6,826,578 | B2 | 11/2004 | Brackett et al. |
| 6,904,434 | B1 | 6/2005 | Wallach et al. |
| 6,963,878 | B2 | 11/2005 | Anson |
| 7,581,191 | B2 * | 8/2009 | Rice et al. .................... 715/764 |
| 2002/0083075 | A1 | 6/2002 | Brummel et al. |
| 2002/0099273 | A1 | 7/2002 | Bocionek et al. |
| 2002/0099686 | A1 | 7/2002 | Schwartz et al. |
| 2002/0186818 | A1 | 12/2002 | Arnaud et al. |
| 2003/0069758 | A1 | 4/2003 | Anderson et al. |
| 2004/0009459 | A1 | 1/2004 | Anderson et al. |
| 2004/0039602 | A1 | 2/2004 | Greenberg et al. |
| 2004/0068514 | A1 | 4/2004 | Chundi et al. |
| 2004/0215651 | A1 | 10/2004 | Markowitz et al. |

2004/0267574 A1   12/2004   Stefanchik et al.

OTHER PUBLICATIONS

Aird et al.; "Vascular Bed-Specific Expression of an Endothelial Cell Gene Is Programmed by the Tissue Microenvironment"; The Journal of Cell Biology; Bearing a date of Sep. 8, 1997; pp. 1117-1124; vol. 138, No. 5; © The Rockefeller University Press.
Brody, Lawrence C.; "Treating Cancer by Targeting a Weakness," The New England Journal of Medicine; Bearing a date of Sep. 1, 2005, Aug. 31, 2005 and 2005; pp. 949-950; © Massachusetts Medical Society.
Bryant et al.; "Specific killing of BRCA2-deficient tumours with inhibitors of poly(ADP-ribose) polymerase," Nature; Bearing a date of Apr. 14, 2005 and 2005; vol. 434; pp. 917-921; Nature Publishing Group.
Cahalan et al.; "Real-time imaging of lymphocytes in vivo"; Current Opinion in Immunology; Bearing a date of 2003; pp. 372-377; vol. 15.
Carver et al.; "Caveolae: Mining Little Caves for New Cancer Targets"; Nature Reviews; Bearing dates of Aug. 2003 and 2003; pp. 571-581; vol. 3; Nature Publishing Group.
Condeelis et al.; "Intravital Imaging of Cell Movement in Tumours"; Nature Reviews; Bearing a date of Dec. 2003; pp. 921-930; vol. 3.
Contag et al.; "The writing is on the vessel wall"; Nature; Bearing dates of Jun. 10, 2004 and 2004; pp. 618-619; vol. 429; Nature Publishing Group.
"DrugTarget Portal™"; LifeSpan Biosciences; Bearing a date of 2005; printed on Sep. 12, 2005; pp. 1-2; located at: https://www.lsbio.com/products/expression/DrugTargetDB.aspx; LifeSpan, Inc.
Essler et al.; "Molecular specialization of breast vasculature: A breast-homing phage-displayed peptide binds to aminopeptidase P in breast vasculature"; bearing a date of Feb. 19, 2002; pp. 2252-2257; vol. 99; No. 4.
Farmer et al.; "Targeting the DNA repair defect in *BRCA* mutant cells as a therapeutic strategy," Bearing dates of Apr. 14, 2005 and 2005; Nature, vol. 434; pp. 913-917; © Nature Publishing Group.
Folkman, Judah; "Looking for a good endothelial address"; Cancer Cell; Bearing a date of Mar. 2002; pp. 113-115.
"Gene Family Localization Data"; LifeSpan Biosciences; Bearing a date of 2005; printed on Sep. 12, 2005; pp. 1-3; located at: https://www.lsbio.com/products/expression/familyspecific.aspx.

(Continued)

*Primary Examiner*—Lori A Clow
(74) *Attorney, Agent, or Firm*—Keller LaPuma Woodard PC

(57) ABSTRACT

An apparatus, device, methods, computer program product, and system are described that access a first dataset in response to a first request associated with a treatment parameter and a first predictive basis, determine a graphical illustration of a first possible outcome of a use of the treatment parameter with respect to at least one body portion, based on the first dataset, access a second dataset in response to a second request associated with the treatment parameter and a second predictive basis, and determine a modified graphical illustration of a second possible outcome of the use of the treatment parameter with respect to the at least one body portion, based on the second dataset.

40 Claims, 26 Drawing Sheets

OTHER PUBLICATIONS

Hood et al.; "Tumor Regression by Targeted Gene Delivery to the Neovasculature"; Science; Bearing dates of Jun. 28, 2002 and Oct. 2002; pp. 2404-2407 and 1; vol. 296.

Hsu et al.; "Neural Systems Responding to Degrees of Uncertainty in Human Decision-Making"; Science; bearing a date of Dec. 9, 2005; pp. 1680-1683; vol. 310.

Hu et al.; "Targeting tissue factor on tumor vascular endothelial cells and tumor cells for immunotherapy in mouse models of prostatic cancer"; PNAS; Bearing dates of Aug. 9, 2001 and Oct. 9, 2001; vol. 98; No. 21.

Kaplan et al.; "VEGFR1-positive haematopoietic bone marrow progenitors initiate the pre-metastatic niche"; Nature; Bearing dates of Dec. 8, 2005 and 2005; vol. 438; pp. 820-827; © 2005 Nature Publishing Group.

"LifeSpan DrugTarget™"; Lifespan Biosciences; Bearing a date of 2005; printed on Sep. 12, 2005; pp. 1-2; located at: https://www.lsbio.com/products/expression/DrugTargetDB.aspx; LifeSpan, Inc.

"LifeSpan FlexModule Database™"; LifeSpan Biosciences; Bearing a date of 2005; printed on Sep. 12, 2005; pp. 1-2; located at: https://www.lsbio.com/products/expression/flexmodule.aspx; LifeSpan, Inc.

M'Rini et al.; "A Novel Enodthelial L-Selectin Ligand Activity in Lymph Node Medulla That Is Regulated by $^{\alpha 1}$ (1,3)-Fucosyltransrerase-IV"; J. Exp. Med.; Bearing a date of Nov. 3, 2003; vol. 198, No. 9; © The Rockefeller University Press.

Madri et al.; "Capillary Endothelial Cell Cultures: Phenotypic Modulation by Matrix Components"; The Journal of Cell Biology; Bearing a date of Jul. 1983; pp. 153-165; vol. 97; © The Rockefeller University Press.

McIntosh et al.; "Targeting endothelium and its dynamic caveolae for tissue-specific transcytosis in vivo: A pathway to overcome cell barriers to drug and gene delivery"; PNAS; Bearing a date of Feb. 19, 2002; pp. 1996-2001; vol. 99; No. 4.

Oh et al.; "Immunoisolation of Caveolae with High Affinity Antibody Binding to the Oligomeric Caveolin Cage"; The Journal of Biological Chemistry; Bearing dates of Aug. 13, 1999, Aug. 31, 1998, and May 10, 1999; pp. 23144-23154; vol. 274, No. 33.

Oh et al.; "Subtractive Proteomic Mapping of the Endothelial Surface in Lung and Solid Tumors for Tissue-Specific Therapy"; Nature; Bearing dates of Jun. 10, 2004 and 2004; pp. 629-635; vol. 429; © 2004 Nature Publishing Group.

Pasqualini et al.; "Organ targeting in vivo using phage display peptide libraries"; Nature; Bearing a date of Mar. 28, 1996; pp. 364-366; vol. 380.

Pasqualini et al.; "Probing the structural and molecular diversity of tumor vasculature"; TRENDS in Molecular Medicine; Bearing dates of Dec. 2002 and 2002; pp. 563-571; vol. 8 No. 12; © 2002 Elsevier Science Ltd.

Perou et al.; "Molecular portraits of human breast tumours"; Nature; Bearing a date of Aug. 17, 2000; pp. 747-752; vol. 406; © 2000 Macmillan Magazines Ltd.

Rajotte et al.; "Molecular Heterogeneity of the Vascular Endothelium Revealed by In Vivo Phage Display"; J. Clin. Invest.; Bearing dates of Feb. 6, 1998, May 21, 1998 and Jul. 1998; pp. 430-437; vol. 102, No. 2; © The American Society for Clinical Investigation, Inc.

Schnitzer et al.; "Separation of Caveolae from Associated Microdomains of GPI-Anchored Proteins"; Science; Bearing a date of Sep. 8, 1995; pp. 1435-1439; vol. 269.

"Tissue Specific Localization Data"; LifeSpan Biosciences; Bearing a date of 2005; printed Sep. 12, 2005; pp. 1-6; located at: https://www.lsbio.com/products/expression/tissuespecific.aspx; LifeSpan, Inc.

"3-D Computer Display Brings Precision to Burn Assessment"; ScienceDaily; Bearing a Date of Oct. 18, 1997; pp. 1-3; located at: http://www.sciencedaily.com/releases/1997/10/971017065158.htm.

U.S. Appl. No. 11/586,439, Jung et al.
U.S. Appl. No. 11/586,349, Jung et al.
U.S. Appl. No. 11/585,784, Jung et al.
U.S. Appl. No. 11/585,662, Jung et al.
U.S. Appl. No. 11/540,927, Jung et al.
U.S. Appl. No. 11/516,689, Jung et al.
U.S. Appl. No. 11/503,501, Jung et al.
U.S. Appl. No. 11/478,295, Jung et al.
U.S. Appl. No. 11/471,289, Jung et al.
U.S. Appl. No. 11/362,545, Jung et al.
U.S. Appl. No. 11/347,804, Jung et al.

\* cited by examiner

FIG. 5

| | 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
|---|---|---|---|---|---|---|---|---|
| 502 | Lung Tissue | Non-Lung Tissue | Endothelial Tissue proximate to Lung Tissue | Endothelial Tissue proximate to Non-Lung Tissue | APP associated with Intermediate Target | I-labeled monoclonal APP Antibodies | Essentially Direct | Radio-immunotherapy via Low-Levels of radionuclides |
| 504 | Lung Tissue | Non-Lung Tissue | Endothelial Tissue proximate to Lung Tissue | Endothelial Tissue proximate to Non-Lung Tissue | APP associated with Intermediate Target | Binding Agent X | Essentially Direct | Treatment Agent X |
| 506 | Diseased Lung Tissue | Non-Diseased Lung Tissue | Endothelial Tissue proximate to Diseased Lung Tissue | Endothelial Tissue proximate to Non-Diseased Lung Tissue | 15 differentially expressed proteins associated with Endothelial Tissue | I-labeled monoclonal APP Antibodies generated for selected one(s) of the 15 proteins | Essentially Direct | Radio-immunotherapy via Low-Levels of radionuclides |

FIG. 6

| 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent and/or 402 Treatment Agent Precursor |
|---|---|---|---|---|---|---|---|
| Breast Tissue | Pancreas Tissue | Vascular Beds of Breast Tissue | Vascular Beds of Pancreas Tissue | APP of Vascular Bed of Breast Tissue | CPGPEGAGC peptide | Essentially Direct | Phages |
| Melanoma Tumors | Surrounding Non-tumor tissues | Endothelial Cells having Integrin avB3 | Endothelial Cells without Integrin avB3 | Integrin avB3 | AvB3 ligand | Cationic polymerized lipid-based nanoparticles | Coupled gene |

602 ↗ (first data row)

604 ↗ (second data row)

FIG. 7

| | 306 Treatment Parameter Direct End Target | 308 Discriminated End Target | 310 Direct Intermediate Targets | 312 Discriminated Intermediate Targets | 314 Target-Related, Tissue Ancestry-Correlated Binding Site | 316 Target-Related, Tissue Ancestry-Correlated Binding Agent | 318 Treatment Agent Delivery Mechanism Relative to Target-Related, Tissue Ancestry-Correlated Binding Agent | 320 Treatment Agent |
|---|---|---|---|---|---|---|---|---|
| 702 | Lung Tissue(s) | Tissues other than Lung | Endothelial Cell Caveolae Proximate to Lung | Endothelial Cell Caveolae Distal from Lung | Antigen to which monoclonal antibody TX3.833 binds | Monoclonal antibody TX3.833 | Essentially Direct via Endothelial Cell Caveolae | Gold |
| 704 | Prostrate Tumors in Mice | All other tissues | Tissue Factor(s) expressed by/on endothelial cells near tumor and by/on tumor itself | Tissue Factor in Other Locations | Tissue Factor | Factor VII, a ligand for tissue factor | Essentially Direct | Fc Effector Domain |
| 706 | Metastatic Niche(s) | Tissues other than Metastatic Niche(s) | Endothelial cells at Metastatic Niche(s) | Endothelial Cells at Other Locations | VEGFR1 | Antibody to VEGFR1 | Essentially Direct | Antibody to VEGFR1 |

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Pro Gly Pro Glu Gly Ala Gly Cys
1               5
```

DATA ACCESSING TECHNIQUES RELATED TO TISSUE CODING

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Kunin, Benefit of Prior-Filed Application, USPTO Electronic Official Gazette, Mar. 18, 2003. The present applicant entity has provided below a specific reference to the application(s)from which priority is being claimed as recited by statute. Applicant entity understands that the statute is unambiguous in its specific reference language and does not require either a serial number or any characterization such as "continuation" or "continuation-in-part." Notwithstanding theforegoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation in part of currently co-pending U.S. patent application entitled Data Techniques Related to Tissue Coding, naming Edward K. Y. Jung, Robert W. Lord, and Lowell L. Wood, Jr., as inventors, U.S. Ser. No. 11/222,031, filed Sep. 8, 2005.

2. For purposes of the USPTO extra-statutory requirements, the present application constitutes a continuation in part of currently co-pending U.S. patent application entitled Data Techniques Related to Tissue Coding, naming Edward K. Y. Jung, Robert W. Lord, and Lowell L. Wood, Jr., as inventors, U.S. Ser. No. 11/241,868, filed Sep. 30, 2005.

3. For purposes of the USPTO extra-statutory requirements, the present application constitutes a continuation in part of currently co-pending U.S. patent application entitled Accessing Data Related to Tissue Coding, naming Edward K. Y. Jung, Robert W. Lord, and Lowell L. Wood, Jr., as inventors, U.S. Ser. No. 11/262,499, filed Oct. 28, 2005.

4. For purposes of the USPTO extra-statutory requirements, the present application constitutes a continuation in part of currently co-pending U.S. patent application entitled Accessing Data Related to Tissue Coding, naming Edward K. Y. Jung, Robert W. Lord, and Lowell L. Wood, Jr., as inventors, U.S. Ser. No. 11/286,133, filed Nov. 23, 2005.

5. For purposes of the USPTO extra-statutory requirements, the present application constitutes a continuation in part of currently co-pending U.S. patent application entitled Accessing Predictive Data, naming Edward K. Y. Jung, Royce A. Levien, Robert W. Lord, Mark A. Malamud, John D. Rinaldo, and Lowell L. Wood, Jr., as inventors, U.S. Ser. No. 11/311,906, filed Dec. 19, 2005.

6. For purposes of the USPTO extra-statutory requirements, the present application constitutes a continuation in part of currently co-pending U.S. patent application entitled Accessing Predictive Data, naming Edward K. Y. Jung, Royce A. Levien, Robert W. Lord, Mark A. Malamud, John D. Rinaldo, and Lowell L. Wood, Jr., as inventors, U.S. Ser. No. 11/314,730, filed Dec. 21, 2005.

The subject matter of the material in the associated sequence listing text file, "1105-002-017-000000 Sequence Listing", created on Mar. 23, 2010 (1kb), is hereby incorporated-by-reference.

TECHNICAL FIELD

This description relates to data handling techniques.

SUMMARY

An embodiment provides a method. In one implementation, the method includes but is not limited to accessing a first dataset in response to a first request associated with a treatment parameter and a first predictive basis, determining a graphical illustration of a first possible outcome of a use of the treatment parameter with respect to at least one body portion, based on the first dataset, accessing a second dataset in response to a second request associated with the treatment parameter and a second predictive basis, and determining a modified graphical illustration of a second possible outcome of the use of the treatment parameter with respect to the at least one body portion, based on the second dataset. In addition to the foregoing, other method aspects are described in the claims, drawings, and text forming a part of the present disclosure.

An embodiment provides a computer program product. In one implementation, the computer program product includes but is not limited to a signal-bearing medium bearing at least one of one or more instructions for accessing a first dataset in response to a first request associated with a treatment parameter and a first predictive basis, the signal bearing medium bearing one or more instructions for determining a graphical illustration of a first possible outcome of a use of the treatment parameter with respect to at least one body portion, based on the first dataset, the signal bearing medium bearing one or more instructions for accessing a second dataset in response to a second request associated with the treatment parameter and a second predictive basis, and the signal bearing medium bearing one or more instructions for determining a modified graphical illustration of a second possible outcome of the use of the treatment parameter with respect to the at least one body portion, based on the second dataset. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to access a first dataset in response to a first request associated with a treatment parameter and a first predictive basis, determine a graphical illustration of a first possible outcome of a use of the treatment parameter with respect to at least one body portion, based on the first dataset, access a second dataset in response to a second request associated with the treatment parameter and a second predictive basis, and determine a modified graphical illustration of a second possible outcome of the use of the treatment parameter with respect to the at least one body portion, based on the second dataset. In addition to the foregoing, other system aspects are described in the claims, drawings, and text forming a part of the present disclosure.

An embodiment provides a device. In one implementation, the device comprises a treatment system, the treatment system comprising a treatment data memory that is operable to store treatment data in association with at least a first predictive basis and a second predictive basis, and treatment logic that is operable to access, from the treatment data memory and in response to a first request and a second request, respectively, a first dataset associated with the first predictive basis and a second dataset associated with the second dataset, the treatment logic being operable to determine a graphical illustration of a first possible outcome of a use of the treatment parameter with respect to at least one body portion, based on the first dataset, and to determine a modified graphical illustration of a second possible outcome of the use of the treatment parameter with respect to the at least one body portion, based on the second dataset. In addition to the foregoing, other device aspects are described in the claims, drawings, and text forming a part of the present disclosure.

An embodiment provides a method. In one implementation, the method includes but is not limited to accessing a first dataset in response to a first request associated with a treatment parameter and a first predictive basis, determining data associated with a first possible outcome of a use of the treatment parameter with respect to at least one body portion, based on the first dataset, accessing a second dataset in response to a second request associated with the treatment parameter and a second predictive basis, and determining data associated with a second possible outcome of the use of the treatment parameter with respect to the at least one body portion, based on the second dataset. In addition to the foregoing, other method aspects are described in the claims, drawings, and text forming a part of the present disclosure.

An embodiment provides a computer program product. In one implementation, the computer program product includes but is not limited to a signal-bearing medium bearing at least one of one or more instructions for accessing a first dataset in response to a first request associated with a treatment parameter and a first predictive basis, the signal bearing medium bearing one or more instructions for determining data associated with a first possible outcome of a use of the treatment parameter with respect to at least one body portion, based on the first dataset, the signal bearing medium bearing one or more instructions for accessing a second dataset in response to a second request associated with the treatment parameter and a second predictive basis, and the signal bearing medium bearing one or more instructions for determining data associated with a second possible outcome of the use of the treatment parameter with respect to the at least one body portion, based on the second dataset. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to access a first dataset in response to a first request associated with a treatment parameter and a first predictive basis, determine data associated with a first possible outcome of a use of the treatment parameter with respect to at least one body portion, based on the first dataset, access a second dataset in response to a second request associated with the treatment parameter and a second predictive basis, and determine data associated with a second possible outcome of the use of the treatment parameter with respect to the at least one body portion, based on the second dataset. In addition to the foregoing, other system aspects are described in the claims, drawings, and text forming a part of the present disclosure.

An embodiment provides a device. In one implementation, the device comprises a treatment system, the treatment system comprising a treatment data memory that is operable to store treatment data in association with at least a first predictive basis and a second predictive basis, and treatment logic that is operable to access, from the treatment data memory and in response to a first request and a second request, respectively, a first dataset associated with the first predictive basis and a second dataset associated with the second predictive basis, the treatment logic being operable to determine data associated with a first possible outcome of a use of the treatment parameter with respect to at least one body portion, based on the first dataset, and to determine data associated with a second possible outcome of the use of the treatment parameter with respect to the at least one body portion, based on the second dataset. In addition to the foregoing, other device aspects are described in the claims, drawings, and text forming a part of the present disclosure.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BRIEF DESCRIPTION OF THE DRAWINGS

FIG. 5 illustrates another alternative embodiment of treatment data associated with the clinical system of FIG. 1, with specific examples of treatment data.

FIG. 6 illustrates additional alternative embodiments of treatment data associated with the clinical system of FIG. 1, with specific examples of treatment data, including CPGPE-GAGC (SEQ. ID. NO. 001).

FIG. 7 illustrates additional alternative embodiments of treatment data associated with the clinical system of FIG. 1, with specific examples of treatment data.

The use of the same symbols in different drawings typically indicates similar or identical items.

DETAILED DESCRIPTION

Figure 1:
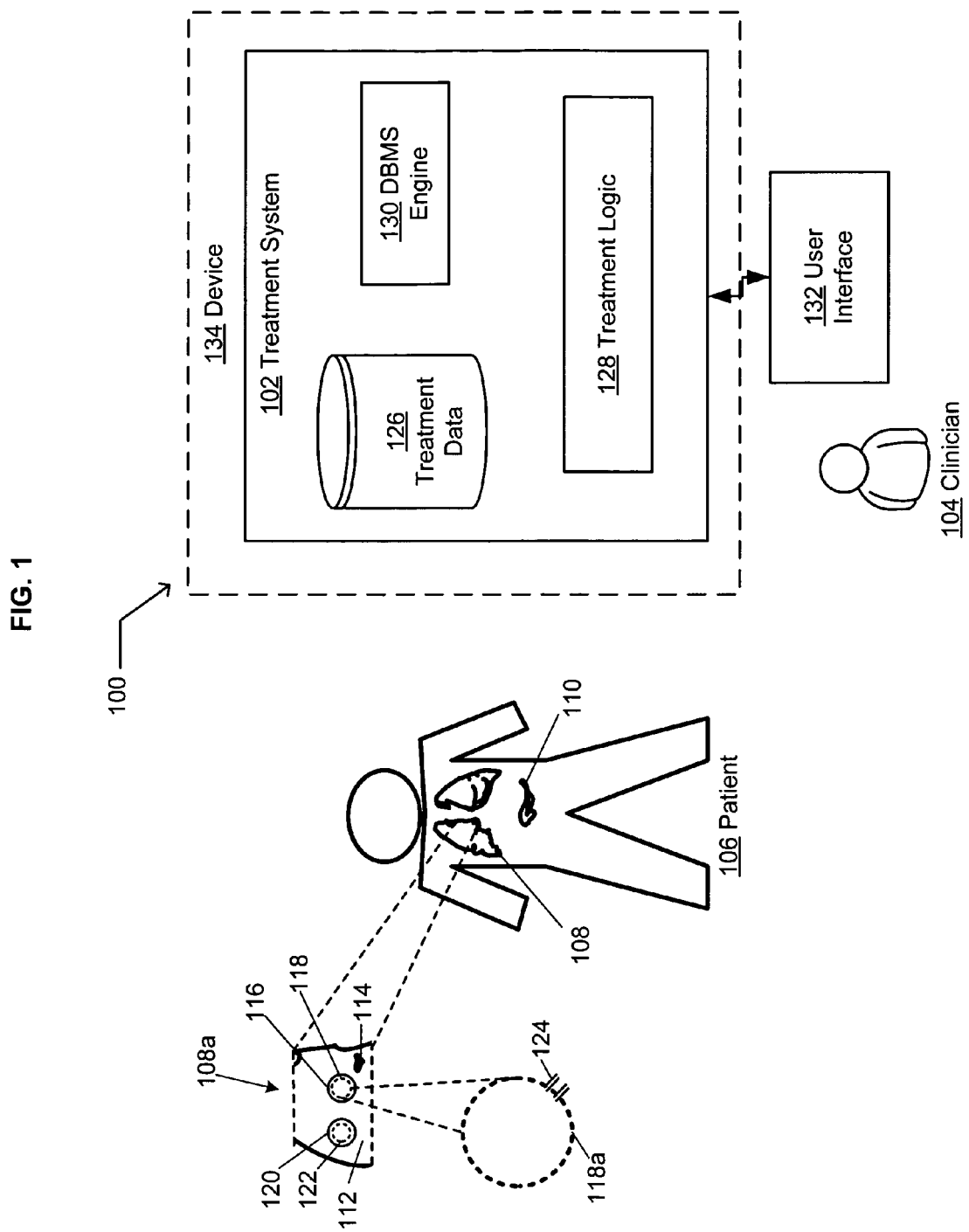
FIG. 1 illustrates an example clinical system in which embodiments may be implemented, perhaps in a device.

FIG. 1 illustrates an example clinical system 100 in which embodiments may be implemented. The clinical system 100 includes a treatment system 102. The treatment system 102 may be used, for example, to store, recall, access, process, implement, or otherwise use information that is beneficial in a clinical setting(s). For example, the treatment system 102 may be used to diagnose or treat patients by storing and/or providing information as to whether or how treatment agent(s) may be applied to a specific region(s) of interest of the human body, such as, for example, a lobe of the lungs, breast tissue, cancerous tissue at a certain bodily location, or other such regions of interest. As a further example, the treatment system 102 may provide information as to whether and/or how to minimize or avoid application of such treatment agents to regions of non-interest (for example, regions to which the treatment agent(s) should not be applied, in order to avoid, e.g., problematic side effects and other undesired results). On the basis of such clinical information, for example, targeted applications of treatment agents (e.g., medication, imaging agents, or other beneficial medical agents) may be carried out in a manner that achieves a desired outcome, while minimizing or eliminating unwanted applications to non-targeted bodily regions.

In FIG. 1, the treatment system 102 is used by a clinician 104. The clinician 104 may, for example, use the treatment system 102 to enter, store, request, or access clinical information such as, for example, the various examples provided herein. The clinician 104 may generally represent, for example, any person involved in health care, including, for example, a doctor, a nurse, a physician's assistant, or a medical researcher. The clinician 104 also may represent someone who is involved in health care in the sense of developing, managing, or implementing the treatment system 102, e.g., a software developer with clinical knowledge (or access to clinical knowledge), a database manager, or an information technologies specialist. Even more generally, some or all of various functions or aspects described herein with respect to the clinician 104 may be performed automatically, e.g., by an appropriately-designed and implemented computing device, or by software agents or other automated techniques.

A patient 106 generally represents any person with an illness, injury, or disease, or who is thought to potentially have such an illness, injury, or disease, or who may be wholly or partially healthy but who is nonetheless studied in order to determine information about such an illness, injury, or disease. The patient 106 also may represent or include other diagnostic and/or animal subjects that may be used in order, for example, to determine an efficacy of a particular medication or treatment, specific examples of which are provided herein. The patient 106 may represent a particular patient in a given clinical setting, such as in a doctor's office, or in a hospital, who is to be diagnosed and/or treated using the treatment system 102. The patient 106 also may represent the more abstract notion of a class of patients (e.g., patients having a certain age, gender, race, genetic makeup, or disposition to illness or disease), or, even more generally, may represent the general notion of a generic patient during basic research and/or development or application of various medical treatments or procedures. In this latter sense, the patient 106 may also represent a non-human animal (such as a primate) believed to be sufficiently similar to a human for the particular purposes that they may usefully substitute for such for the particular purposes.

As such, the patient 106 generally possesses or is associated with, for example, some or all of the various organs, systems, organ systems, organ subsystems, diseased tissue, and/or healthy tissue that may be found in the body. In FIG. 1, the patient 106 is illustrated as having a lung 108 and a pancreas 110, so that these (and other) body parts may be used as the bases for the specific examples given herein. Of course, many other applications of the treatment system 102 exist, over and above the examples provided herein.

In an exploded portion 108a of the lung 108, various example elements are illustrated, although not drawn to scale for the purposes of clarity and ease of illustration and description. For example, the lung 108 may include a healthy tissue portion 112, and a diseased tissue portion 114. The healthy tissue 112 may include, for example, healthy lung tissue, while the diseased tissue 114 may include, for example, a tumor or other cancerous tissue.

The lung 108 also may include a blood vessel 116, which is illustrated in a cut-away view, and which includes a tissue component 118 known as, by way of example nomenclature, the endothelium, endothelial layer, or endothelial cells. The endothelium or endothelial layer 118 generally refers to a layer of cells that lines an interior of a portion of the circulatory system, such as the blood vessel 116. In FIG. 1, the blood vessel 116 and the endothelial layer 118 are illustrated as being in the vicinity of the diseased tissue 114. In contrast, an example of a blood vessel 120 is illustrated that contains endothelial layer 122. The blood vessel 120 is shown as being in the vicinity of the healthy tissue 112 of the lung 108.

Certain properties of the endothelial layer 118 and the endothelial layer 122 may enable the targeted delivery of one or more treatment agents to a vicinity of the diseased tissue 114 and the healthy tissue 112, respectively. For example, blood (and other cells contained therein) will be transported within and along a length of the blood vessel 116, where the length of the blood vessel 116 naturally extends a relatively long distance in either direction toward/away from the diseased tissue 114. However, cells of the endothelial layer 118 that have developed and/or grown over a period of time in a vicinity of the diseased tissue 114 may exhibit characteristics that are unique, or essentially unique, to a site on the endothelial layer 118 in that particular vicinity.

For example, the diseased tissue 114 may include a tumor that has grown over a period of time. During that period of time, a corresponding growth or development of a site on the endothelial layer 118 may reflect, or otherwise be correlated with and/or affected by, the growth of the diseased tissue (tumor) 114. This correlation between the history or ancestry of the site on the endothelial layer 118 in the vicinity of the diseased tissue 114 may result in unique, or almost unique, properties of the tissue ancestry-correlated site, such as, for example, a display of specific and identifiable proteins. Moreover, similar comments may apply to a tissue ancestry-correlated site along the endothelial layer 122 of the blood vessel 120, in the vicinity of the healthy tissue 112. In this way, each such tissue ancestry-correlated site, whether in the lung or in other sites in the body, may be used to provide, effectively, a molecular-level address that specifies a location within the body, e.g., a location of the diseased tissue 114 and/or the healthy tissue 112.

Other mechanisms exist by which such effective molecular-level addresses, such as those that may, in some instances, entail some logical relation to tissue ancestry-correlated sites, may arise at a given location in the body. For example, such sites may originate in or at a first location in the body, and may thereafter undergo transport to, and engraftment/implantation at, a second location in the body. For example, tissue may originate in bone marrow, or in a distant neoplasm, and may be transported through the vasculature to another, second location in the body (e.g., the lungs 108). Such tissue, which may be, for example, as small as a single cell, may embed at the second location and thereafter serve as a molecular-level address or site to which other agent(s) may bind.

Accordingly, such tissue ancestry-correlated sites may be used to direct treatment agents (such as, for example, medications, imaging agents, or radio-immunotherapy agents) in a desired fashion. For example, as described in more detail in certain examples provided herein, radionuclides may be applied to the diseased tissue 114.

In this regard, it should be understood that, without use of the tissue ancestry-correlated site(s) described herein, it may be difficult to direct such treatment agents to desired body regions with a necessary or desired level of precision. For example, many treatment agents may be delivered by injection (or by other delivery modalities, e.g., swallowing or absorption through the skin) into a bloodstream of the patient 106. However, without an effective way to direct the treatment agents once in the bloodstream, a positive impact of the treatment agents may be reduced or eliminated. Moreover, ancillary delivery of the treatment agents to undesired regions (e.g., delivery of radionuclides to the healthy tissue 112 and/or to the pancreas 110 or other organs) may result in harm to the patient 106. Such harm may be particularly acute or problematic in cases where, for example, a concentration, dosage, or amount of the treatment agent in the bloodstream is required to be increased relative to an optimal treatment amount, simply to ensure that some portion of the treatment agent reaches and affects a desired end target. Similar comments may apply to other treatment modalities. For example, treatment of the diseased tissue 114 (e.g., a tumor) may be performed by radiation therapy in which the patient is exposed to radiation, and, again, the net effect of such treatment(s) may be negative due to harm caused by the radiation to the healthy tissue 112.

As just described, then, tissue ancestry-correlated sites may exist within and along the endothelial layers 118 and/or 122, in the vicinity of correlated tissues that may serve as target(s) (e.g., the diseased tissue 114) for certain treatment agent(s). For example, these target-related tissue ancestry-correlated sites may include, as described herein, certain proteins that may be known to bind to/with certain other agents. In one specific example discussed herein, a target-related tissue ancestry-correlated binding site includes a protein, aminopeptidase-P (APP), that is known to bind with an agent such as, for example, I-labeled monoclonal antibodies. If a treatment agent (such as, for example, radionuclides) is associated with the target-related tissue ancestry-correlated binding agent (e.g., the I-labeled monoclonal antibodies), then injection of the target-related tissue ancestry-correlated binding agent into the bloodstream will result in delivery of the treatment agent (e.g., radionuclides) to the target-related tissue ancestry-correlated binding site (e.g., APP in the vicinity of the lung 108). That is, as the target-related tissue ancestry-correlated binding agent moves through the bloodstream, the target-related tissue ancestry-correlated binding agent will bind with the target-related tissue ancestry-correlated binding site in the vicinity of the, in this example, diseased tissue 114, thus resulting in effective application of the attached treatment agent in the desired region of the body of the patient 106.

In many cases, delivery of the treatment agent(s) to the vicinity of desired body regions, by delivering the treatment agents to defined sites along a blood vessel wall(s) in the desired vicinity, may be sufficient to obtain a desired result, even if the treatment agents are continually contained within the blood vessel(s) at the target-related tissue ancestry-correlated binding sites. In various cases, treatment agent delivery should occur with greater or lesser levels of specificity and/or efficacy. For example, in some cases, it may be sufficient to provide the treatment agent in the lung 108, while in other cases the treatment agent must or should be applied substantially only to the diseased tissue 114.

Additionally, in some cases, it may be possible and/or desirable to breach or penetrate a wall of the blood vessel(s) 116/120, in order to reach associated tissue(s) directly. For example, in FIG. 1, an enlarged view 118a of the endothelial layer 118 is illustrated that includes a mechanism by which the treatment agents may directly access a direct end target of tissue (e.g., the diseased tissue 114). Specifically, FIG. 1 illustrates a mechanism 124 that may include, for example, structures known as caveolae. Although the mechanism (e.g., caveolae) 124 are shown conceptually in FIG. 1 as tubes or access points, caveolae generally refer to small invaginations of a surface of the blood vessel 116 that carry out certain transport and/or signaling functions between cells within the blood vessel 116 and cells outside of the blood vessel 116 (e.g., the diseased tissue 114). Further discussion regarding caveolae 124 is provided in various examples, herein.

Although many other examples are provided herein and with reference to the various figures, it should be understood that many types and instances of treatment data may play a role in the use and application of the various concepts referenced above and described in more detail herein. The treatment system 102 may store such treatment data 126 in a database or other memory, for easy, convenient, and effective access by the clinician 104.

The treatment data 126 may include, for example, not only the target-related tissue ancestry-correlated binding site(s) and/or the related target-related tissue ancestry-correlated binding agent(s), but also various other parameters and/or characteristics related to treatment of the patient 106, examples of which are provided herein. Through detailed storage, organization, and use of the treatment data 126, the clinician 104 may be assisted in determining optimal treatment techniques for the patient 106, in order, for example, to select and deliver an appropriate type and/or level of a treatment agent, with an appropriate degree of accuracy, to a desired end target (based on an appropriate target-related tissue ancestry-correlated binding site and/or an appropriate target-related tissue ancestry-correlated binding agent), while minimizing any negative impact of such a selection/delivery, if any, on other regions of the body of the patient 106. Ordered assignment and/or storage of information within the treatment data 126, as described herein, facilitates and/or enables such recall, access, and/or use of the treatment data by the clinician 104 in treating the patient 106.

In the treatment system 102, treatment logic 128 may be used to store, organize, access, recall, or otherwise use the information stored in the treatment data 126. For example, the treatment logic 128 may access a database management system (DBMS) engine 130, which may be operable to perform computing operations to insert or modify new data into/within the treatment data 126, perhaps in response to new research or findings, or in response to a preference of the clinician 104. For example, if a new treatment agent is discovered to be effective on the diseased tissue 114, the clinician 104 may access the treatment system 102 using a user interface 132, in order to use the DBMS engine 130 to associate the new treatment agent with one or more instances of the target-related tissue ancestry-correlated binding site(s) and/or target related tissue ancestry-correlated binding agent(s) that may be known to be useful in targeting the diseased tissue 114, within the treatment data database 126 (assuming that the treatment agent is suitable for direct or indirect delivery via the target-related tissue ancestry-correlated binding agent, as described herein). As another example, if a new target-related tissue ancestry-correlated binding site is identified in the endothelial layer 118 in the vicinity of the diseased tissue 114, then this new target-related tissue ancestry-correlated binding site may be associated with one or more instances of a target-related tissue ancestry-correlated binding agent, e.g., there may be more than one agent that is useful in attaching to the new target-related tissue ancestry-correlated binding site for delivery of one or more treatment agents.

Similarly, in a case where the clinician 104 seeks, for example, to diagnose or treat the patient 106, the clinician 104 may access the user interface 132 to use the treatment logic 128 and/or the DBMS Engine 130 to determine best known methods or treatments to be applied in a given clinical scenario. For example, if the patient 106 has a certain type of disease or illness in a certain region of the body, then the clinician may input this information via the user interface 132 in order to obtain one or more options for treating the disease or illness. For example, if the patient 106 exhibits the diseased tissue 114, then the clinician 104 may select the (type of) diseased tissue 114 in the lung 108 as an end target, and the treatment logic 128 may then interface with the DBMS engine 130 to obtain, from the treatment data 126, one or more options for providing the treatment agent to the diseased tissue 114, e.g., one or more target-related tissue ancestry-correlated binding sites (such as, for example, two different proteins that are expressed or displayed in the endothelial layer 118 in the vicinity of the diseased tissue 114). As another example, if the clinician 104 is already aware of a target-related tissue ancestry-correlated binding site in the vicinity of the diseased tissue 114, then the clinician 104 may input this information into the treatment system 102 and be provided with one or more, for example, target-related tissue ancestry-correlated binding agents that may be known to attach to the known target-related tissue ancestry-correlated binding site.

In this regard, it should be understood that multiple instances of a target-related tissue ancestry-correlated binding site, as described, may be present at any one location in the body, and, moreover, virtually any region or site in the body having a blood-tissue interface may also exhibit an associated, target-related tissue ancestry-correlated binding site. Further, new instances of target-related tissue ancestry-correlated binding sites may be discovered and/or approved for clinical use on a relatively frequent basis. Still further, there may be many different treatment parameters and/or characteristics that may be related to the various target-related tissue ancestry-correlated binding site(s) and/or target-related tissue ancestry-correlated binding agent(s), such as, for example, treatment agents and/or delivery mechanisms.

As a result, the clinician 104, e.g., a physician in the field, may not be aware of all currently-available content of the treatment data 126. Thus, the treatment system 102 provides the clinician with readily-available, accurate, current, and/or comprehensive treatment information, and also provides techniques to ensure that the treatment information remains accurate, current, and/or comprehensive, by allowing the addition and/or modification of the existing treatment data 126, as new treatment information becomes available.

In FIG. 1, the treatment system 102 is illustrated as possibly being included within a device 134. The device 134 may include, for example, a mobile computing device, such as a personal digital assistant (PDA), or a laptop computer. Of course, virtually any other computing device may be used to implement the treatment system 102, such as, for example, a workstation, a desktop computer, or a tablet PC.

Additionally, not all of the treatment system 102 need be implemented on a single computing device. For example, the treatment data 126 may be stored on a remote computer, while the user interface 132 and/or treatment logic 128 are implemented on a local computer. Further, aspects of the treatment system 102 may be implemented in different combinations and implementations than that shown in FIG. 1. For example, functionality of the DBMS engine 130 may be incorporated into the treatment logic 128 and/or the treatment data 126.

The treatment data 126 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
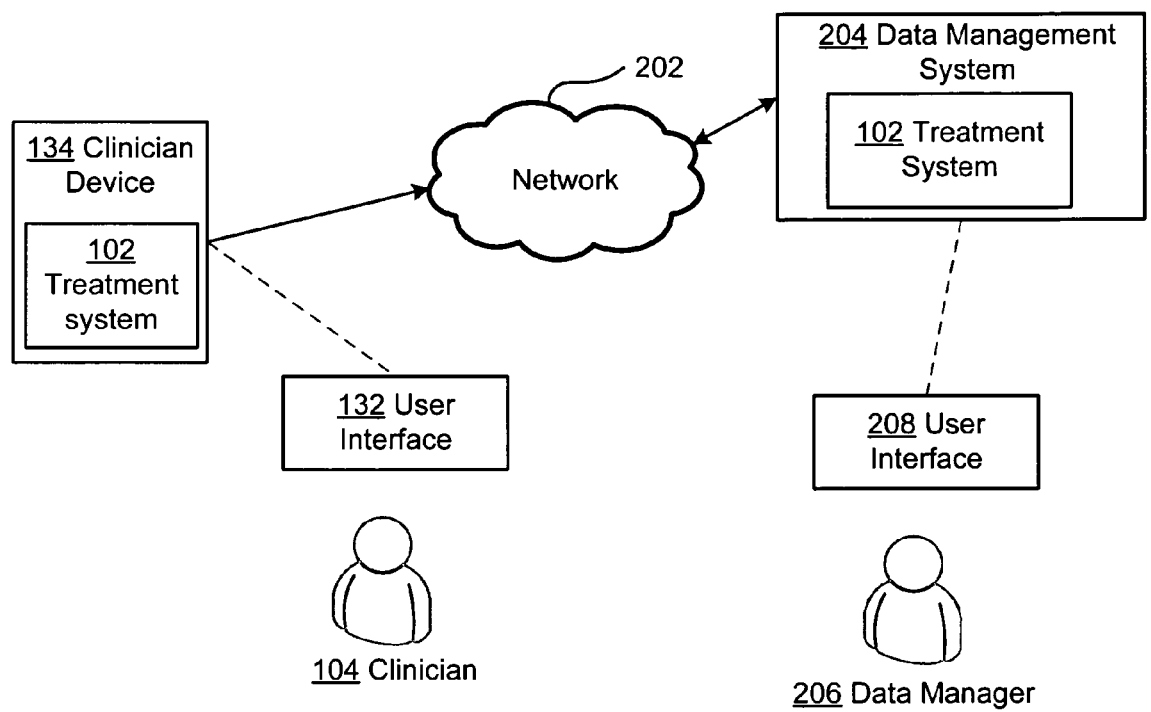
FIG. 2 illustrates certain alternative embodiments of the clinical system of FIG. 1.

FIG. 2 illustrates certain alternative embodiments of the clinical system 100 of FIG. 1. In FIG. 2, the clinician 104 uses the user interface 132 to interact with the treatment system 102 deployed on the clinician device 134. The clinician device 134 is in communication over a network 202 with a data management system 204, which is also running the treatment system 102; the data management system 204 may be interacted with by a data manager 206 through a user interface 208. Of course, it should be understood that there may be many clinicians other then the specifically-illustrated clinician 104, each with access to an individual implementation of the treatment system 102. Similarly, multiple data management systems 204 may be implemented.

In this way, the clinician 104, who may be operating in the field, e.g., in an office and/or hospital environment, may be relieved of a responsibility to update or manage contents in the treatment data 126, or other aspects of the treatment system 102. For example, the data management system 204 may be a centralized system that manages a central database of the treatment data 126, and/or that deploys or supplies updated information from such a central database to the clinician device 134.

Figure 3:
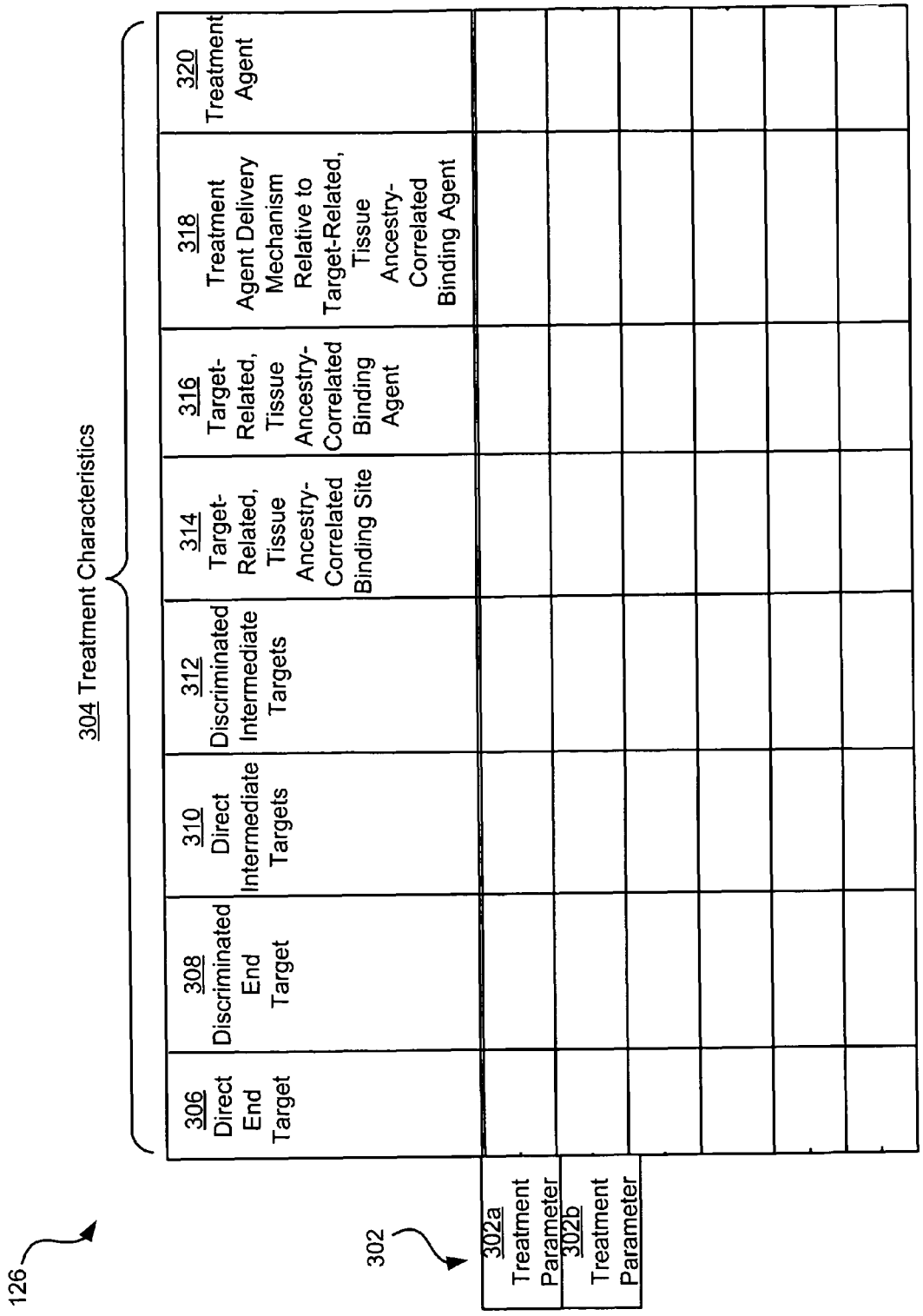
FIG. 3 illustrates an alternative embodiment of treatment data associated with the clinical system of FIG. 1.

FIG. 3 illustrates an alternative embodiment of the treatment data 126 associated with the clinical system 100 of FIG. 1. In FIG. 3, and in the various examples herein, a particular nomenclature is used for the terms described above and related terms, in order to provide consistency and clarity of description. However, it should be understood that other terminology may be used to refer to the same or similar concepts.

In FIG. 3, treatment parameters 302 are stored and organized with respect to a plurality of treatment characteristics 304. The treatment characteristics 304 include many of the terms and concepts just described, as well as additional, but not exhaustive, terms and concepts that may be relevant to a use and operation of the treatment system 102.

For example, the treatment characteristics 304 include a direct end target 306. The direct end target 306 may refer, for example, to any tissue, organ, organ system, organ subsystem (or type thereof), or any other body part or region that may be targeted for healing, destruction, repair, enhancement, and/or imaging that may be targeted—directly or indirectly—via an associated target-related tissue ancestry-correlated binding site 314 and/or an associated target-related tissue ancestry-correlated binding agent 316 and/or an associated treatment agent delivery mechanism relative to the target-related tissue ancestry-correlated binding agent 318 and/or an associated treatment agent 320. A discriminated end target 308 refers to targets that should be avoided during implementation of the healing, destruction, repair, enhancement and/or imaging actions that may be discriminated—directly or indirectly—via an associated target-related tissue ancestry-correlated binding site 314 and/or an associated target-related tissue ancestry-correlated binding agent 316 and/or an associated treatment agent delivery mechanism relative to the target-related tissue ancestry-correlated binding agent 318 and/or an associated treatment agent 320. For example, in FIG. 1, the lung 108 may include the direct end target 306 as the diseased tissue 114, and may include the discriminated end target 308 as the healthy tissue 112, and/or the pancreas 110.

Somewhat analogously, a direct intermediate target 310 refers to targets that are connected to, associated with, or in the vicinity of the direct end target that may be targeted via an associated target-related tissue ancestry-correlated binding site 314 and/or an associated target-related tissue ancestry-correlated binding agent 316 and/or an associated treatment agent delivery mechanism relative to the target-related tissue ancestry-correlated binding agent 318 and/or an associated treatment agent 320. For example, a portion of the endothelial layer 118 in a vicinity of the diseased tissue 114 (or other end target) may act as a direct intermediate target 310. Then, a discriminated intermediate target 312 may refer to endothelial tissue of the layer 118 that is not in a vicinity of the diseased tissue 114 that may be discriminated via an associated target-related tissue ancestry-correlated binding site 314 and/or an associated target-related tissue ancestry-correlated binding agent 316 and/or an associated treatment agent delivery mechanism relative to the target-related tissue ancestry-correlated binding agent 318 and/or an associated treatment agent 320.

As already referenced, a target-related tissue ancestry-correlated binding site 314 refers to a determined chemical and/or genetic and/or biological structure to which various chemical compounds and/or genes may be affixed. For example, the target-related tissue ancestry-correlated binding site 314 may include a specific protein that is displayed at the endothelial layer 118 in a vicinity of the diseased tissue 114. The target-related tissue ancestry-correlated binding site 314 may be selectively associated with the direct end target 306 either directly or through the direct intermediate target 310.

A target-related tissue ancestry-correlated binding agent 316, then, may refer to some specific chemical and/or genetic and/or biological structure that more or less selectively binds or attaches to a related one of the target-related tissue ancestry-correlated binding sites 314. The target-related tissue ancestry-correlated binding agent 316 also may be associated with a treatment agent delivery mechanism relative to the target-related tissue ancestry-correlated binding agent 318, which may refer either to something that may be directly attached to (or associated with) the target-related tissue ancestry-correlated binding agent 316, and/or something that may be attached to (or associated with) one or more intermediary or indirect structures that attach to the target-related tissue ancestry-correlated binding agent 316 and that act to house and/or deliver a treatment agent 320. As an example of the intermediary or indirect structures just referenced, a nano-container may be used that dissolves and/or otherwise opens in a vicinity of the target-related tissue ancestry-correlated binding site 314, and thereby releases and/or delivers the treatment agent 320 included inside.

The treatment agent 320 thus binds/attaches to, or otherwise is associated with, either directly or indirectly, the target-related tissue ancestry-correlated binding agent 316. Thus, as described, the treatment agent 320 may be effectively transported to the appropriate direct intermediate target 310 and thereby to the target-related tissue ancestry-correlated binding site 314. In this way, the treatment agent 320 may be delivered to the direct end target 306 (or at least to a vicinity of the direct end target 306), while not being delivered either to the discriminated intermediate target(s) 312 and/or the discriminated end target(s) 308.

FIG. 3 thus illustrates that there may be many different relationships or associations between any one (or more) of the treatment characteristics 304. For example, one or more instances of any one or more of the treatment characteristics 304 may be considered to be one of the treatment parameters 302, and thereafter associated with one or more instances of the remaining treatment characteristics 304. For example, the direct end target 306 may be considered to be the treatment parameter(s) 302, where a first instance 302a of the direct end target 306 may refer to diseased lung tissue, and the second instance 302b may refer to diseased breast tissue, and both instances may be associated with an instance of the target-related tissue ancestry-correlated binding agent 316. Similarly, two or more instances of the target-related tissue ancestry-correlated binding agent 316 (e.g., I-labeled APP monoclonal antibodies targeted on two different antigens) may be associated with one treatment agent 320 (e.g., radio-immunotherapy via application of low levels of radionuclides).

Many other examples of relationships and associations between the various treatment parameters 302 and/or the treatment characteristics 304 (and/or other treatment information) may be defined or determined and stored in the treatment data 126 according to the treatment logic 128. Certain of these examples are provided herein.

Additionally, although the treatment data 126 is illustrated conceptually in FIG. 3 as a flat table in which one or more of the selected treatment parameters 302 are associated with one or more of the treatment characteristics, it should be understood that this illustration is for explanation and example only, and is not intended to be limiting in any way with respect to the various ways in which the treatment data 126 may be stored, organized, accessed, recalled, or otherwise used.

For example, the treatment data 126 may be organized into one or more relational databases. In this case, for example, the treatment data 126 may be stored in one or more tables, and the tables may be joined and/or cross-referenced in order to allow efficient access to the information contained therein. Thus, the treatment parameter(s) 302 may define a record of the database(s) that is associated with various ones of the treatment characteristics 304.

In such cases, the various tables may be normalized so as, for example, to reduce or eliminate data anomalies. For example, the tables may be normalized to avoid update anomalies (in which the same information would need to be changed in multiple records, and which may be particularly problematic when treatment data database 126 is large), deletion anomalies (in which deletion of a desired field or datum necessarily but undesirably results in deletion of a related datum), and/or insertion anomalies (in which insertion of a row in a table creates an inconsistency with another row(s)). During normalization, an overall schema of the database may be analyzed to determine issues such as, for example, the various anomalies just referenced, and then the schema is decomposed into smaller, related schemas that do not have such anomalies or other faults. Such normalization processes may be dependent on, for example, desired schema(s) or relations between the treatment parameters 302 and/or treatment characteristics 304, and/or on desired uses of the treatment data 126.

Uniqueness of any one record in a relational database holding the treatment data 126 may be ensured by providing or selecting a column of each table that has a unique value within the relational database as a whole. Such unique values may be known as primary keys. These primary keys serve not only as the basis for ensuring uniqueness of each row (e.g., treatment parameter) in the database, but also as the basis for relating or associating the various tables within one another. In the latter regard, when a field in one of the relational tables matches a primary key in another relational table, then the field may be referred to a foreign key, and such a foreign key may be used to match, join, or otherwise associate (aspects of) the two or more related tables.

FIG. 3 and associated potential relational databases represent only one example of how the treatment data may be stored, organized, processed, accessed, recalled, and/or otherwise used.

Figure 4:
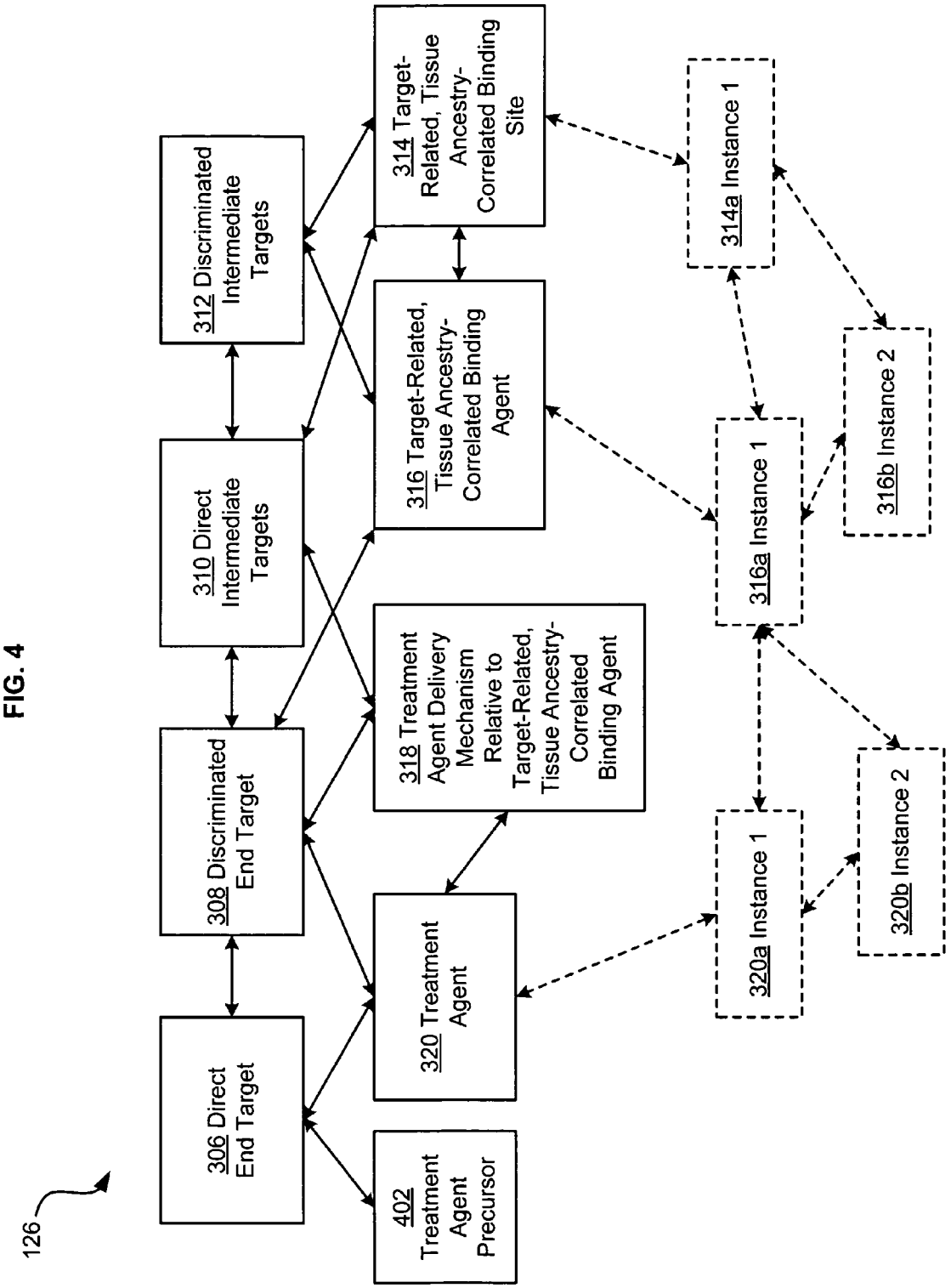
FIG. 4 illustrates another alternative embodiment of treatment data associated with the clinical system of FIG. 1.

FIG. 4 illustrates another alternative embodiment of treatment data 126 associated with the clinical system 100 of FIG. 1, in which the treatment data 126 is conceptually illustrated as being stored in an object-oriented database.

In such an object-oriented database, the various treatment parameter(s) 302 and/or treatment characteristic(s) 304, and/or instances thereof, may be related to one another using, for example, links or pointers to one another. FIG. 4 illustrates a conceptualization of such a database structure in which the various types of treatment data are interconnected, and is not necessarily intended to represent an actual implementation of an organization of the treatment data 126.

The concepts described above may be implemented in the context of the object-oriented database of FIG. 4. For example, two instances 320a and 320b of the treatment agent 320 may be associated with one (or more) instance 316a of the target-related tissue ancestry-correlated binding agent 316. Meanwhile, two instances 316a and 316b of the target-related tissue ancestry-correlated binding agent 316 may be associated with an instance 314a of the target-related tissue ancestry-correlated binding site 314.

Also, other data may be included in the treatment data 126. For example, in FIG. 4, a treatment agent precursor 402 is shown that refers generally to an agent used to facilitate application of the treatment agent 320, e.g., an immune-response element that is used to identify/mark/bond with the target-related tissue ancestry-correlated binding site 314 and/or a substance that when metabolized becomes treatment agent 320, such as with prodrugs.

Many other examples of databases and database structures also may be used. Other such examples include hierarchical models (in which data are organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

As referenced herein, the treatment system 102 may be used to perform various data querying and/or recall techniques with respect to the treatment data 126, in order to facilitate treatment and/or diagnosis of the patient 106. For example, where the treatment data are organized, keyed to, and/or otherwise accessible using one or more of the treatment parameters 302 and/or treatment characteristics 304, various Boolean, statistical, and/or semi-Boolean searching techniques may be performed.

For example, SQL or SQL-like operations over one or more of the treatment parameters 302/treatment characteristics 304 may be performed, or Boolean operations using the treatment parameters 302/treatment characteristics 304 may be performed. For example, weighted Boolean operations may be performed in which different weights or priorities are assigned to one or more of the treatment parameters 302/treatment characteristics 304, perhaps relative to one another. For example, a number-weighted, exclusive-OR operation may be performed to request specific weightings of desired (or undesired) treatment data to be included (excluded).

For example, the clinician 104 may wish to determine examples of the direct end target 306 that are associated with examples of the discriminated end target 308 that are highly discriminated against with respect to delivery of the target-related tissue ancestry-correlated binding agent 316, for highly-specific delivery of the treatment agent 320. For example, the clinician 104 may want to know instances of the treatment agent 320 that may be delivered to the lungs as the direct end target 306, without substantially affecting the pancreas, liver, or other tissue, organ, or organ system/subsystem. In other examples, the clinician may be willing to tolerate lower levels of discrimination (e.g., increased delivery of the treatment agent 320 to other body regions), perhaps because the patient 106 is in an advanced stage of illness. As another example, the clinician 104 may start with a preferred (type of) the treatment agent 320, and may request from the treatment system 102 various delivery techniques (e.g., target-related tissue ancestry-correlated binding agent 316) that may be available, perhaps with varying levels of efficacy.

The clinician 104 may specify such factors using, for example, the user interface 132. For example, the clinician 104 may be able to designate one or more of the treatment parameters 302/treatment characteristics 304, and assign a weight or importance thereto, using, for example, a provided ranking system. In this regard, and as referenced herein, it should be understood that the clinician 104 may wish to deliver a particular instance of the treatment agent 320, e.g., a particular radionuclide to be delivered to a tumor. However, such a treatment agent, if applied by conventional techniques, may be problematic or prohibited (e.g., where a current physiological condition of the patient 106 and/or state of an immune system of the patient 106 is insufficient to allow the clinician 104 to use the desired treatment agent). Moreover, the clinician 104 may not be aware that a suitable target-related tissue ancestry-correlated binding site 314 and/or target-related tissue ancestry-correlated binding agent 316 has (have) been discovered for delivering the treatment agent with a desired/required level of accuracy. However, the clinician 104 may query the treatment system 102 based on the desired treatment agent 320, and may thereby discover the technique(s) by which the treatment agent may be applied, and with the necessary level of specificity.

Similarly, data analysis techniques (e.g., data searching) may be performed using the treatment data 126, perhaps over a large number of databases. For example, the clinician 104 may perform a physical screening of the patient 106, and may input some body system, tissue, organ, or organ system/subsystem parameters against which screening is to be performed. Then, the clinician should receive a listing of target-related tissue ancestry-correlated binding sites and/or target-related tissue ancestry-correlated binding agents that are ranked according to some criteria. For example, the clinician 104 may receive a listing of instances of the target-related tissue ancestry-correlated binding site 314 that provide a particularly high or low level of discrimination with respect to a particular direct end target 306, discriminated end target 308, and/or treatment agent 320. In this way, for example, if the patient 106 has an organ or organ subsystem that requires protection from a given instance of the treatment agent 320, then the clinician 104 may select an instance of the target-related tissue ancestry-correlated binding site 314 and/or of the target-related tissue ancestry-correlated binding agent 316 accordingly, even if some relative sacrifice of binding strength/accuracy is associated with such a selection.

By way of further example, other parameters/characteristics may be factored in. For example, elimination pathways may be tracked, databased, and/or weighted for use in the treatment data 126 and/or the treatment system 102. For example, if a particular instance of the target-related tissue ancestry-correlated binding agent is especially readily eliminated by the liver, then, in a case where the patient 106 has impaired hepatic function, such an instance may be selected for delivering the treatment agent 320, even if an otherwise superior instance of the target-related tissue ancestry-correlated binding agent 316 is known. Algorithms implementing such query/recall/access/searching techniques may thus use Boolean or other techniques to output, for example, a thresholded, rank-ordered list. The treatment logic 128 may then assign a key or other identifier to such a list(s), for easier use thereof the next time a like query is performed.

Design and testing of querying techniques in particular implementations of the treatment system 102 may involve, for example, entry of candidate treatment parameters 302/treatment characteristics 304 (or instances thereof) into a database(s), along with associated test results and/or affinity metrics that may be used to determine/weight targets or sets of targets. Then, an identifier may be generated that is unique to the target(s) set(s).

Still other examples/applications include avoiding an autoimmune response of the patient 106, in order to achieve a desired result. For example, the treatment system 102 may be used to determine/catalog/use treatment data that relates to treatment parameters 302/treatment characteristics 304 that are known or suspected to avoid self-epitopes (i.e., those unlikely to generate an undesired autoimmune response). FIG. 5 illustrates another alternative embodiment of treatment data associated with the clinical system 100 of FIG. 1, with specific examples of treatment data. In particular, all of FIGS. 5-7 provide or refer to example results from related technical papers, which are specifically referenced below.

For example, rows of the table of FIG. 5 (e.g., rows 502, 504, and 506, respectively) refer to examples that may be found in Oh, P. et al., "Subtractive Proteomic Mapping of the Endothelial Surface in Lung and Solid Tumours for Tissue-Specific Therapy," Nature, vol. 429, pp. 629-635 (Jun. 10, 2004), which is hereby incorporated by reference in its entirety, and which may be referred to herein as the Oh reference.

In the Oh reference, it is generally disclosed that regions of endothelium may change or alter over time, based on what tissues are in the vicinity thereof, as referenced herein. The Oh reference, for example, identified lung-induced and/or lung-specific endothelial cell surface proteins based on a hypothesis that a surrounding tissue (micro) environment of the endothelial cell surface proteins modulates protein expression in the vascular endothelium. The Oh reference identified specific proteins that were found to be expressed at an endothelial surface by specifying two regions of interest (e.g., a "lung region" and a "non-lung region"), and then determining proteins within the two regions. Then, by subtracting the two sets of proteins from one another, non-common proteins were identified.

In this way, uniquely occurring proteins at a specific endothelial site (e.g., the target-related tissue ancestry-correlated binding site 314 at a specific direct intermediate target 310) were identified. Then, these uniquely-occurring proteins were used as targets for generated antibodies. As a result, it was possible to target, for example, lung-specific tissues as opposed to non-lung-specific tissues, and/or to target tumors as opposed to non-tumor tissues. More specifically, for example, it was determined to be possible to target tumor-induced endothelial cell proteins (e.g., target-related tissue ancestry-correlated binding sites 314) for delivery thereto of drugs, imaging agents, and/or radiation agents (e.g., treatment agents 320) that were attached to appropriate antibodies (target-related tissue ancestry-correlated binding agents 316).

Thus, to set forth specific examples, a row 502 illustrates an example in which the direct end target 306 includes a treatment parameter of "lung tissue." In this example, the discriminated end target 308 includes "non-lung tissue." The direct intermediate target 310 includes endothelial tissues that are proximate to the lung tissue, while the discriminated intermediate target 312 includes endothelial tissue that is proximate to the non-lung tissue.

The target-related tissue ancestry-correlated binding site 314 in this example includes aminopeptidase-P (APP), which is a protein that was detected substantially only in endothelial plasma membranes from the lung tissue (e.g., direct end target 306). In order to take advantage of the immuno-accessibility of APP in vivo, $I^{125}$-labeled monoclonal antibodies were used as the target-related tissue ancestry-correlated binding agent 316, and were intravenously injected into test rats. Subsequent imaging of the lungs illustrated rapid and specific targeting of APP antibody to the lung (e.g., direct end target 306), with significantly reduced accumulation of the injected dose at non-lung tissue (e.g., the discriminated end target 308). Thus, by selecting the treatment agent 320 to include radio-immunotherapy via low levels of radionuclides (e.g., 100 µCi of $I^{125}$), a treatment agent delivery mechanism relative to target-related tissue ancestry-correlated binding agent 318 may involve essentially direct delivery, in that the radionuclide(s) may be affixed to the monoclonal APP antibodies, similarly to how the $I^{125}$ was affixed as described in Oh, et al. Further, although the term antibody is used herein in various examples, it should be understood that other immuno-reactive features of the adaptive immune system also may be used in a similar or analogous manner, including entities that serve to mediate antibody generation, such as, for example, helper T cells or dendritic cells.

In the row 504 of FIG. 5, a conceptual secondary example drawn from/based on the Oh reference is included, in order to illustrate various concepts described herein, e.g., with respect to FIGS. 1-4. Specifically, in the row 504, various ones of the treatment parameters and/or treatment characteristics are the same as in the row 502, except that a second example of the target-related tissue ancestry-correlated binding agent 316 is illustrated generically as "Binding Agent X," and, similarly, a second example of a generically-referenced treatment agent 320 is illustrated as "Treatment Agent X." As such, the row 504 illustrates, for example, that two separate instances of the target-related tissue ancestry-correlated binding agent 316 and/or the treatment agent 320 may be associated with, e.g., an instance of either the direct end target 306, and/or with an instance of the target-related tissue ancestry-correlated binding site 314.

The row 506 illustrates another example from the Oh reference. In the row 506, the direct end target 306 is illustrated as "diseased lung tissue," while the discriminated end target 308 is illustrated as "non-diseased lung tissue." Thus, the direct intermediate target 310 is illustrated as "endothelial tissue proximate to the diseased lung tissue," while the discriminated intermediate target 312 is illustrated as "endothelial tissue that is proximate to non-diseased lung tissue."

Then, the target-related tissue ancestry-correlated binding site 314 is illustrated as fifteen differentially-expressed proteins (e.g., expressed according to the subtractive techniques described herein) associated with the direct intermediate target 310, e.g., the endothelial tissue proximate to the diseased lung tissue. As a result, the target-related tissue ancestry-correlated binding agent 316 is selected and illustrated as I-labeled monoclonal APP antibodies that may be generated for one or more of the fifteen differentially-expressed proteins. As in the row 502, the treatment agent delivery mechanism relative to target-related tissue ancestry-correlated binding agent 318 may involve essentially direct attachment of the treatment agent 320 that is illustrated as radio-immunotherapy via low-levels of radionuclides. In this way, such radionuclides may be concentrated in, and may thereby destroy, tumors. In particular, for example, an identified tumor target was the 34 KDa protein recognized by annexin A1 (AnnA1) antibodies, which was significantly present in substantially only in tumor endothelial plasma membrane.

FIG. 6 illustrates additional alternative embodiments of treatment data associated with the clinical system 100 of FIG. 1, with specific examples of treatment data. In FIG. 6, a row 602 illustrates examples that may be found in Essler et al., "Molecular Specialization of Breast Vasculature: A Breast-Homing Phage-Displayed Peptide Binds to Aminopeptidase P in Breast Vasculature," Proceedings of the National Academy of Sciences, vol. 99, No. 4, pp. 2252-2257 (Feb. 19, 2002), which is hereby incorporated by reference in its entirety, and which may be referred to herein as the Essler reference.

In the Essler reference, a plurality of peptides (e.g., two or more amino acids joined together via a peptide bond) having a general structure of CX7C (where C is cysteine and X is any amino acid) I-labeled monoclonal antibodies were injected into mice. Then tissues of interest were observed to determine a presence of phage(s), and thereby to determine which peptide of the plurality of peptides honed in on the observed tissue(s). In this way, it was determined that the CPGPE-GAGC (SEQ. ID. NO. 001) peptide was useful in providing a homing point for phages of the patient's immune system, and, in particular, was useful as a binding agent for the breast tissue, while not binding to pancreas tissue. Although these specific examples of peptides are provided for illustration and explanation, it should be understood that the term peptide as used herein may refer to virtually any lineal peptide-bonded string of amino acid residues, which include various structures thereof, unless context dictates otherwise. For example, a lipopeptide may be interpreted to include virtually all lipoproteins, while glycopeptides may include virtually all glycoproteins.

Thus, in the row 602, the direct end target 306 is illustrated as breast tissue, while the discriminated end target 308 is illustrated as pancreas tissue. The direct intermediate target 310 is illustrated as vascular beds of breast tissue, while the discriminated intermediate target 312 is illustrated as vascular beds of pancreas tissue.

The target-related tissue ancestry-correlated binding site 314 includes a protein, aminopeptidase-P (APP), of the vascular bed of breast tissue. The target-related tissue ancestry-correlated binding agent 316 includes a cyclic nonapeptide known as the CPGPEGAGC (SEQ. ID. NO. 001) peptide, which is shown in the Essler paper to home to the aminopeptidase P receptor. The treatment agent precursor 402 is shown to include phages, which were essentially directly delivered via the CPGPEGAGC (SEQ. ID. NO. 001) peptide to the APP of the vascular bed of breast tissue, and which facilitate attachment of additional/alternative treatment agents 320 to the APP.

A row 604 of FIG. 6 illustrates an example from Hood et al., "Tumor Regression by Targeted Gene Delivery to the Neovasculature," Science, vol. 296, pp. 2404-2407 (Jun. 28, 2002), which is incorporated by reference in its entirety and which is referred to herein as the Hood reference. The Hood reference refers to the molecule integrin avB3 that plays a role in endothelial cell survival during formation of new blood vessels in a given region, and is preferentially expressed therein. A cationic polymerized lipid-based nanoparticle was synthesized and covalently coupled to a small organic avB3 ligand; that is, the ligand was demonstrated to serve as a binding agent for the integrin avB3 that is preferentially expressed in endothelial cells.

Accordingly, in the row 604, melanoma tumors were used as the direct end target 306, while the discriminated end target 308 is shown as surrounding non-tumor tissues. The direct intermediate target 310 is illustrated as endothelial cells having integrin avB3, while the discriminated intermediate target 312 is shown as endothelial cells without integrin avB3. Thus, the target-related tissue ancestry-correlated binding site 314 is shown to include the integrin avB3, while the target-related tissue ancestry-correlated binding agent 316 is shown to include the avB3 ligand that attaches to the integrin avB3. The treatment agent 320 included a gene selected to disrupt formation of new blood vessels in the tumor(s), which was delivered using the cationic polymerized lipid-based nanoparticle(s), and which thereby deprived the tumor(s) of blood and destroyed the tumor(s).

FIG. 7 illustrates additional embodiments of treatment data associated with the clinical system 100 of FIG. 1, with specific examples of treatment data. In a row 702, an example is illustrated from McIntosh et al., "Targeting Endothelium and Its Dynamic Caveolae for Tissue-Specific Transcytosis in vivo: A Pathway to Overcome Cell Barriers to Drug and Gene Delivery," Proceedings of the National Academy of Sciences, vol. 99, no. 4, pp. 1996-2001 (Feb. 19, 2002), which is hereby incorporated by reference and which may be referred to herein as the McIntosh reference. In the McIntosh reference, endothelial cell plasma membranes from the lungs were analyzed to determine monoclonal antibodies targeted thereto. Additionally, the McIntosh reference illustrated use of the caveolae 124 to allow the treatment agent 320 to cross the endothelium and be delivered directly to lung tissue.

Thus, in the row 702, the direct end target 306 is shown as lung tissue, while the discriminated end target 308 is shown as non-lung tissue. The direct intermediate target 310 is shown as endothelial cell caveolae proximate to the lung tissue, while the discriminated intermediate target 312 is shown as endothelial cell caveolae that is distal from the lung tissue.

The target-related tissue ancestry-correlated binding site 314 is shown as a determined/selected antigen to which the monoclonal antibody TX3.833 binds, so that the target-related tissue ancestry-correlated binding agent 316 is shown as the monoclonal antibody TX3.833 itself. In this way, the treatment agent 320 of gold affixed directly to the TX3.833 antibody was transported over the endothelial plasma membrane into the tissues of interest (e.g., lung tissues); in other words, the caveolae 124 was used to conduct transcytosis.

A row 704 illustrates an example from Zhiwei et al., "Targeting Tissue Factor on Tumor Vascular Endothelial Cells and Tumor Cells for Immunotherapy in Mouse Models of Prostatic Cancer," Proceedings of the National Academy of Sciences, vol. 98, no. 21, pp. 12180-12185 (Oct. 9, 2001), which is hereby incorporated by reference in its entirety, and which may be referred to as the Zhiwei reference. In the Zhiwei reference, a "tissue factor" is identified as a transmembrane receptor that forms a strong and specific complex with an associated ligand, factor VII (fvII). Such tissue factor, although not normally expressed on endothelial cells, may be expressed on tumor endothelial cells of the tumor vasculature.

Thus, in the example of the row 704, the direct end target 306 includes prostrate tumors, while the discriminated end target 308 includes all other tissues. The direct intermediate target 310 includes tissue factor(s) expressed by/on endothelial cells near the tumor(s) and by/on the tumor itself. The target-related tissue ancestry-correlated binding site 314 includes the tissue factor, while the target-related tissue ancestry-correlated binding site agent 316 includes the factor VII (fvII), the ligand for the tissue factor. In this way, the direct treatment agent 320 of an Fc effector domain was used to provide a marker for an induced immune response.

In a row 706, an example is illustrated from Kaplan et al., "VEGFR1-positive haematopoietic bone marrow progenitors initiate the pre-metastatic niche," Nature, vol. 438, no. 4, pp. 820-827 (December 2005), which is hereby incorporated by reference and which may be referred to herein as the Kaplan reference. In the Kaplan reference, metastasis is described as a process in which tumor cells mobilize bone-marrow cells to form a site or "pre-metastatic niche" at particular regions (distant from the primary tumor itself), at which the subsequent metastasis may then develop. More specifically, Kaplan describes the idea that cells of a tumor may secrete a molecular/humoral factor(s) that mobilizes bone marrow cells and stimulates fibroblast cells at a distant (future metastatic) site, thereby upregulating fibronectin (a binding, tissue-promoting protein) that serves as a "docking site" for the bone marrow cells. Some of the bone marrow cells were positive for proteins characteristic of haematopoietic progenitor cells, including, for example, vascular endothelial growth factor receptor 1 (VEGFR1), which, in turn, is described as promoting attachment and motility of tumor cells, thereby leading to metastasis. For example, protease production associated with the bone marrow cells may lead to growth factors (e.g., vascular endothelial growth factor (VEGF) that support the developing niche, through, e.g., angiogenesis). In other words, the VEGFR1-positive bone marrow cells serve to form the "pre-metastatic niche" by colonizing a site distant from the tumor, so that subsequently-arriving tumor cells find a hospitable environment at such a site.

Thus, in the example of the row 706, the direct end target 306 may include one-or-more metastatic and/or pre-metastatic niches or sites that are distant from a primary tumor. For example, such niches may be present in the lungs when the primary tumor includes a melanoma. Then, the discriminated end target 308 may include tissues other than these metastatic niches. The direct intermediate target 310 may include endothelial cells at the metastatic niches, while the discriminated intermediate target 312 may include endothelial cells at other locations. Additionally and/or alternatively, the direct intermediate target 310 may include endothelial cellular structures at the metastatic or pre-metastatic niches, while the discriminated intermediate target 312 may include endothelial cellular structures at other locations. In the example of the row 706, the target-related tissue ancestry correlated binding site 314 includes VEGFR1, which, as referenced above, includes a receptor protein on the endothelial cells (to which VEGF may bind). In this case, and as referenced in the Kaplan reference, the target-related tissue ancestry correlated binding agent 316 may include an antibody to VEGFR1, so that the treatment agent delivery mechanism relative to the target-related tissue ancestry correlated binding agent 318 includes an essentially direct delivery of this antibody, where the antibody to VEGFR1 thereby serves as the treatment agent 320 by blocking the VEGFR1 and preventing formation of, occupying, and/or blocking subsequent interactions with development of the pre-metastatic niche. Of course, the row 706 includes merely one example of target-related tissue ancestry correlated binding site(s) and/or target-related tissue ancestry correlated binding agent(s) that may be located within, or in association with, the pre-metastatic niche(s), where appropriate discovery and/or targeting thereof may be performed by any of the techniques described herein, or other techniques. Moreover, it should be understood from the above description that such target-related tissue ancestry correlated binding site(s) and/or target-related tissue ancestry correlated binding agent(s) may be time-dependent, e.g., with respect to formation and metastasis of the primary tumor. Accordingly, application of the just-referenced techniques may be determined and/or occur based on such time-dependencies, e.g., by applying the techniques for patients at high risk of metastatic disease, but for whom metastatic disease has not yet actualized in the form of established metastases.

In other, related, examples, the treatment(s) just described (e.g., use of an antibody to VEGFR1) should be understood to represent merely an example(s) of how to reduce or eliminate development of the pre-metastatic niche(s) and/or metastasis of the primary tumor. For example, molecular addressing as described herein may be used to slow or stop the upregulation of fibronectin. In such examples, and considering the time-dependent nature of metastasis and treatment just referenced, the alternative treatment modalities (e.g., regulating a presence or development of VEGFR1 and fibronectin) may be seen as complementary to one another. For example, such treatment modalities may be implemented cyclically for the patient 106, the better to disrupt the pre-metastatic/metastatic pathway as a whole, and thereby to increase an efficacy of the overall treatment of the patient 106. Of course, similar comments apply to treatment modalities applied at other points in the pathway, as well as to other pathways, as would be apparent.

Figure 8:
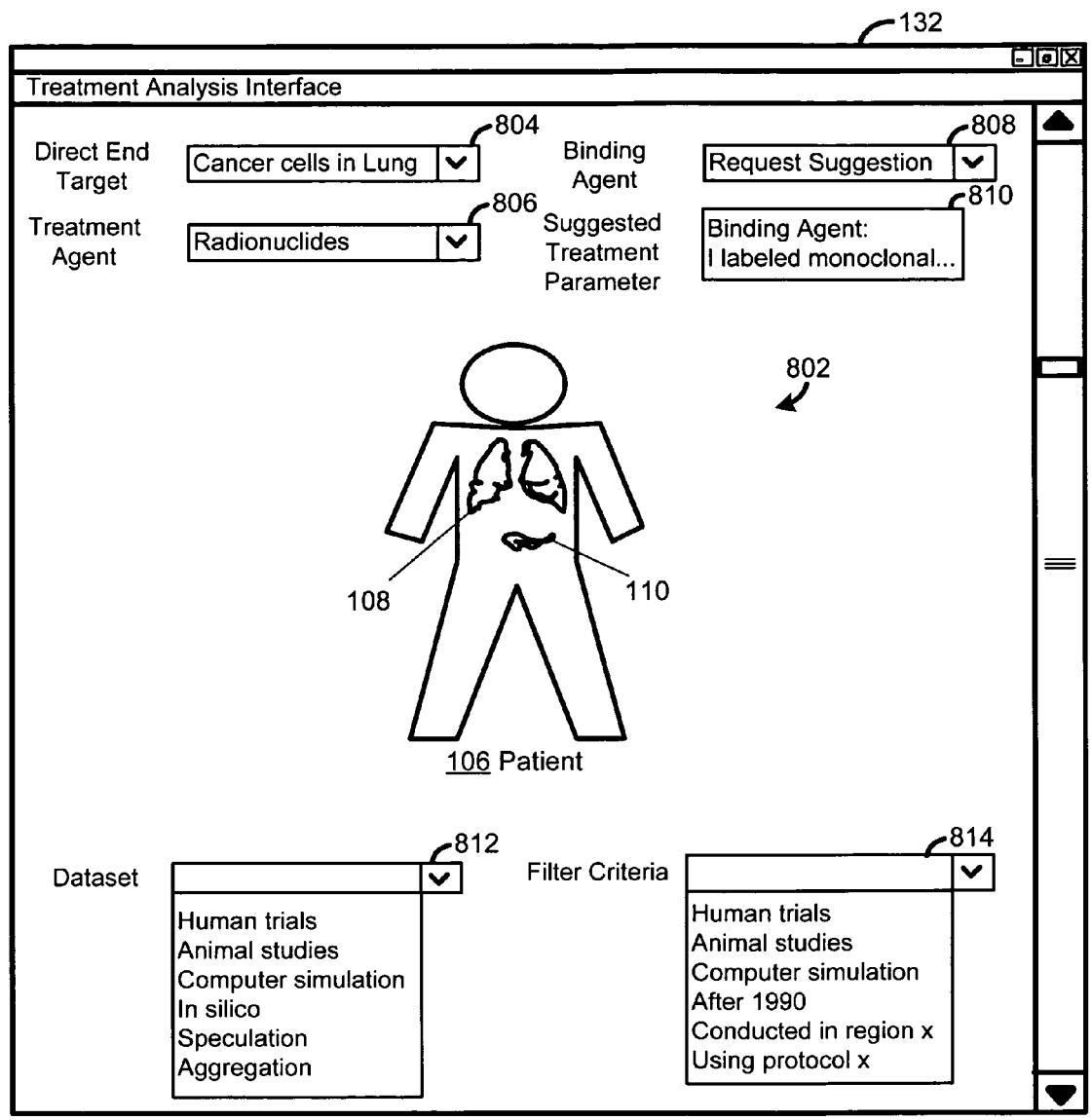
FIG. 8 illustrates an example screenshot of a graphical user interface for accessing predictive data.

FIG. 8 illustrates an example screenshot of a graphical user interface for accessing predictive data. In FIG. 8, an example of the user interface 132 of FIG. 1 is illustrated as providing a graphical illustration 802 of the patient 106. For example, the graphical illustration 802 may include an image of some or all of the patient 106, where the image may include various colors, highlights, or other visual indicators designed to provide information regarding the patient 106, or regarding a diagnosis or treatment of the patient 106. The graphical illustration 802 may illustrate internal organs of interest, and surrounding or related body portions, with varying (and variable) levels of resolution. For example, user controls (not shown in FIG. 8) may be provided that allow the clinician 104 to view the graphical illustration 802 by zooming in or out, or by moving a viewing focus of/on the graphical illustration 802. Although illustrated in FIG. 8 as an outline, the graphical illustration 802 may include other visual representations of the patient 106, which may be generic to a class of patient or specific to a particular patient, and which may include a photograph or other illustration derived from image sensor(s), or a three-dimensional representation of the patient 106. Additionally, or alternatively, the graphical illustration 802 may include a chart, graph, diagram, table, or other representation of data that may be useful to the clinician 104 in diagnosing or treating the patient 106.

In the example of FIG. 8, the user interface 132 includes a plurality of fields 804, 806, 808, 810, 812, and 814. In some implementations, the fields 804-814 allow the clinician to access, analyze, or otherwise consider or use the treatment data 126 of FIG. 1 to diagnose and/or treat the patient 106. For example, as referenced herein, the clinician 104 may determine or consider treatment techniques to select and deliver an appropriate type and/or level of a treatment agent, with an appropriate degree of accuracy, to a desired (direct) end target, while minimizing a negative impact of such a selection/delivery, if any, on other regions of the body of the patient 106. In some implementations, the user interface 132 thus provides the clinician 104 with bases for speculation or conjecture regarding a potential course of treatment or research that may be undertaken with regard to the patient 106. In other words, for example, the user interface 132 allows the clinician 104 to hypothesize about an efficacy, risk, unwanted impact, or side effect of a particular course of treatment that may be undertaken.

For example, the field 804 may include a drop-down menu by which the clinician 104 may select a direct end target that is desired for treatment or analysis. In the example of FIG. 8, the field 804 is illustrated as showing a selection of "cancer cells in lung" as the direct end target. Meanwhile, the field 806 illustrates a selection of "radionuclides" as a potential treatment agent.

As described herein, delivery of radionuclides or other appropriate treatment agents to a desired bodily location may be accomplished by using a "molecular address" provided by a target-related tissue ancestry-correlated binding site, e.g., by associating the treatment agent (radionuclides) with a target-related tissue ancestry-correlated binding agent that is known to deliver the treatment agent to the target-related tissue ancestry-correlated binding site (and thereby, for example, to surrounding target tissue), while discriminating against, or avoiding, ancillary or undesired delivery of the treatment agent to non-target tissue(s). Thus, in the example of FIG. 8, once the clinician 104 selects a desired direct end target using the field 804, and a desired treatment agent in the field 806, then the clinician 104 may select "request suggestion" in the field 808 associated with a target-related tissue ancestry-correlated binding agent, as shown. In this case, the system 100 or similar system (e.g., the system 900 of FIG. 9, discussed in more detail, below) may thus provide a suggestion for the target-related tissue ancestry-correlated binding agent of "I-labeled monoclonal antibodies" in the field 810, for consideration and possible use by the clinician 104 in applying the treatment agent (radionuclides) of the field 806 of the direct end target (cancer cells in lung) of the field 804.

Of course, FIG. 8 and the above discussion provide merely a few examples of how the user interface 132 may be used in conjunction with the treatment logic 128 of the treatment system 102 to access the treatment data 126. In other examples, the clinician 104 may request a suggestion for the direct end target in the field 804, or may request a suggestion for the treatment agent 806, or, on the other hand, may simply specify all desired treatment parameters (in which case no suggested treatment parameter need be provided in the field 810). Further, although FIG. 8 is illustrated for the sake of example as including fields for the direct end target, the treatment agent, and the target-related tissue ancestry-correlated binding agent, it should be understood that any of the various treatment parameters mentioned herein, or other treatment parameters, may be selected or provided in conjunction with the user interface 132.

However the treatment parameter(s) are selected and/or provided in the user interface 132, the graphical illustration 802 may be used to provide possible outcomes of a use of the treatment parameter(s) with respect to one or more body portions. For example, in the illustrated example of FIG. 8, where the treatment parameters of the fields 804-810 are selected or provided, the graphical illustration 802 may be used to illustrate a possible outcome of the use of the treatment parameters with respect to the lungs 108 and/or the pancreas 110. For example, since cancer cells in the lungs 108 are intended to be used as the direct end target, as specified in the field 804, the graphical illustration 802 may be used to illustrate an effect of delivering the specified treatment agent (radionuclides) of the field 806 to the lungs 108, using the target-related tissue ancestry-correlated binding agent suggested in the field 810 (also using, it will be appreciated, the appropriate target-related tissue ancestry-correlated binding site associated with the lungs 108 to which the target-related tissue ancestry-correlated binding agent is known to bind). For example, a color scheme or other visual indicator(s) may be used to indicate an efficacy of the specified treatment parameters with respect to the lungs 108, e.g., by providing the illustration of the lungs 108 in different colors to indicate the efficacy of the specified treatment parameters. Of course, other audio or visual indicators may be used, e.g., the graphical illustration 802 may include a brightness or other visual aspect of the illustration of the lungs 108 that is varied in direct or indirect correspondence with an efficacy of the specified treatment parameters.

As a result, the clinician 104 may, for example, observe and judge an efficacy of a plurality of successively-specified treatment parameters, simply by selecting or requesting examples and combinations thereof, using the fields 804-810. By use in part of such visual indicators as those just described, the clinician 104 may quickly and easily make judgments about which treatment parameter(s) may be most useful in a given diagnostic, treatment, or research scenario.

In some implementations, the graphical illustration 802 may be used to provide other possible outcomes of the use of the treatment parameter(s), beyond illustrating an efficacy thereof. For example, the graphical illustration 802 may automatically illustrate side effects, unwanted impacts, or other risks, ambiguities or consequences of using the specified treatment parameter(s). For example, as described herein, it may be the case that use of the specified treatment parameter(s) may result in an undesired side effect of, for example, delivery of the treatment agent (e.g., radionuclides) to other body portions. Accordingly, the graphical illustration 802 may illustrate body portions that may be affected by the use of the treatment parameter(s) in an undesired, unwanted, and/or detrimental manner. For example, the graphical illustration 802 may include a representation of the pancreas 110, which may be affected by the treatment agent (radionuclides) in an undesired manner. Again, visual indicators may be used to indicate a nature and/or extent of the undesired effect, using, e.g., a designated color scheme, highlighting, numerical or graphical representation, or other visual indications.

Thus, again, the clinician 104 may gain useful information for diagnosing or treating the patient 106, or for general research/inquiry into uses of different treatment parameters. For example, by specifying different (combinations of) treatment parameters, the clinician may observe an efficacy of a desired treatment, relative to a nature and extent of unwanted impacts thereof. For example, the clinician 104 may be reminded (or made aware) of certain side effects that may not otherwise have been considered or known, and may respond accordingly. For example, if the patient 106 is known to have a weakened or somewhat dysfunctional pancreas, then different treatment parameters may be selected to find combinations thereof that retain a desired level of efficacy, while avoiding dangerous or unwanted application of the treatment agent to the pancreas 110.

In providing the graphical illustration 802, including possible outcomes (both beneficial and detrimental) of the use of the specified treatment parameters, the user interface 132 may access and use the treatment data 126, using the treatment logic 128. In the example of FIG. 8, the treatment data 126 may include a plurality of datasets used by the treatment logic 128 to provide the graphical illustration 802, where each dataset may be associated with at least one predictive basis for providing the possible outcome(s) of the use of the various treatment parameters.

For example, a first such dataset may be associated with a first predictive basis that may include previous studies or trials performed on human subjects. That is, results of previous studies or trials performed on human subjects may be stored in the first dataset, and these results may be tagged, identified, or otherwise characterized within the treatment data 126 as having a certain type or degree of predictive value. For example, the first dataset may be characterized as being more predictively useful than results from a second dataset associated with studies or trials based on animals, simply by virtue of having been performed on human subjects. In other examples, the results in the first dataset may be characterized as having been performed in a certain timeframe or environment, under certain funding and/or procedural guidelines, within a defined area or type of medical practice, or having some other predictive basis and/or value. In these and other such examples, the first dataset may be designated to have more or less predictive value than a second dataset that also stores results of studies or trials performed on human subjects, but where the identified characteristic(s) is different in quantity or quality (e.g., performed in a different timeframe or environment, or under more or less stringent funding and/or procedural guidelines, or in a different area of medical practice (e.g., holistic/alternative as compared to traditional)).

In the example of FIG. 8, a field 812 is included that allows the clinician 104 to specify one or more datasets to be used by the treatment logic 128 in generating the graphical illustration 802. For example, the field 812 illustrates that the clinician 104 may select one or more datasets associated with human studies, animal studies, computer simulations, "in silico" datasets, speculated datasets, or aggregated datasets (where, for example, the clinician 104 may specify different combinations or aggregations of the different datasets, e.g., by selecting multiple ones of the listed examples). Of course, these are just examples, and any other knowledge source may be used, as would be apparent, including, for example, any type of in vivo or in vitro or in silico study.

In this way, for example, the clinician 104 may use the user interface 132 as a convenient tool to perform analysis, speculation, or prediction of a possible outcome of the use of specified treatment parameters, based on the different datasets having different predictive bases. For example, for the treatment parameters specified in the fields 804-810, the clinician may first select "human studies" in the field 812, whereupon the user interface 132 may provide the graphical illustration 802 with a first illustration of the lungs 108, perhaps in association with a certain color or other visual indicator designed to illustrate an efficacy of the treatment parameters with respect to the lungs 108 (or, more specifically, with respect to certain types of cancer cells within the lungs 108). In this first example, the pancreas 110 may not initially be illustrated (or may be illustrated but not visually marked or altered), since, for example, the human studies providing the first predictive basis of the first dataset may not have shown any adverse effects with respect to the pancreas 110.

Then, the clinician may specify a second dataset having a second predictive basis, such as, for example, a dataset associated with "animal studies," as selected from the field 812. In this case, the user interface 132 may modify the graphical illustration 802 to provide a modified graphical illustration 802 that includes the pancreas 110 (and/or a visual indicator associated therewith), and that thereby illustrates that the results of the second dataset indicate that a possible outcome of the use of the specified treatment parameters includes unwanted application of the treatment agent to the pancreas 110.

As a result, for example, the clinician 104 may make a more informed decision about a future course of action regarding a diagnosis or treatment of the patient 106. For example, the fact that the animal studies of the second dataset indicate the possible outcome of unwanted impact on the pancreas 110 may not be considered to be conclusive with regard to predicting the same or similar effect on the patient 106 (assuming that the patient 106 is human in this example). Nonetheless, for example, the clinician 104 may be reminded of a possible side effect or other concern that may otherwise have been discounted or forgotten, or, as another example, where the clinician 104 knows that the patient 106 has a weakened or dysfunctional pancreas, the above-described information provided by the user interface 132 may be sufficient for the clinician 104 to continue specifying different treatment parameters in the fields 804-810, in an attempt to determine a more appropriate treatment for the patient 106.

Similar comments apply regarding an efficacy of specified treatment parameter(s) with regard to the lungs 108. For example, the first dataset associated with the human studies may indicate a certain degree of efficacy of the specified treatment parameters of the fields 804-810 (e.g., by way of an appropriate visual indicator, such as color), while the second dataset associated with the animal studies may indicate a greater (or lesser) degree of efficacy. In this case, the clinician 104 may select the specified treatment parameters for use with the patient 106, as compared to alternate treatment parameters. That is, where the clinician 104 is choosing between two or more possible courses of treatment, the clinician 104 may arrive at a selection of a treatment based on a consideration of possible outcomes illustrated by the user interface 132, based on different ones of the datasets of the field 812.

In addition to diagnosis and treatment of the patient 106, the user interface 132 may be used, for example, as a research or speculation tool for determining and assessing possible future treatments. For example, the clinician 104 may be in the process of determining a future course of research with respect to different (combinations of) treatment parameters. In deciding between the different courses of research that may be taken, the clinician 104 may consider possible outcomes of the treatment parameters, using the various datasets of the field 812. For example, if a particular combination of treatment parameters shows a high degree of efficacy (and/or a low degree of unwanted side effects) based on multiple ones of the datasets of the field 812, then the clinician 104 may consider that the particular combination merits further research or clinical-use consideration.

Further in FIG. 8, a field 814 allows the clinician 104 to apply a filter criteria to the dataset(s) specified in the field 812. For example, the filter criteria may remove portions of the current dataset(s) that the clinician 104 may feel have less predictive value in determining the possible outcome(s) of using the specified treatment parameters. For example, the clinician may begin consideration of possible outcomes of the specified treatment parameters by selecting "aggregation" in the field 812, so that the graphical illustration 802 illustrates the possible outcome of use of the treatment parameters based on all of the datasets of the field 812. Then, the clinician 104 may selectively remove a contribution of a selected one or more of the datasets, by, for example, selecting a dataset associated with "animal studies" in the field 814, or selecting a filter criteria of "computer simulation(s)" to remove computer-simulated results from the combined datasets.

In other examples, the filter criteria may not correspond directly or in a one-to-one relationship with one of the datasets of the field 812. For example, the filter criteria may filter information from a combination of datasets, i.e., information that is common to each of the datasets. For example, if the clinician 104 selects "human studies" and "animal studies" using the field 812, then the clinician 104 may select "after 1990" in the field 814 to remove all results from both datasets that were collected prior to 1990. Similarly, as shown in FIG. 8, the field 814 may be used to filter results from one or more datasets based on whether the results were obtained in a particular geographical region (i.e., "region x"), or were obtained in studies conducted according to a particular protocol (i.e., "protocol x").

Thus, FIG. 8 illustrates an example of a graphical user interface including at least a first portion (e.g., one or more of the fields 804-814) configured to receive a first request to provide a graphical illustration (e.g., the graphical illustration 802) of a first possible outcome of a use of a treatment parameter with respect to at least one body portion (e.g., the lungs 108 and/or the pancreas 110), based on a first dataset associated with a first predictive basis (e.g., the first dataset/first predictive basis selected using the field 812). FIG. 8 further illustrates that such a graphical user interface may include at least a second portion (e.g., one or more of the fields 804-814) configured to receive a second request to provide a modified graphical illustration (e.g., a modified version of the graphical illustration 802) of a second possible outcome of the use of the treatment parameter, based on a second dataset associated with a second predictive basis (e.g., the second dataset/second predictive basis selected using the field 812). Thus, the graphical user interface also may include a third portion configured to illustrate the graphical illustration and the modified graphical illustration (e.g., the portion of the user interface 132 of FIG. 8 including the graphical illustration 802), so as, for example, to include at least a portion of the at least one body portion (e.g., at least a portion of the lungs 108), and/or to include one other body portion (e.g., the pancreas 110) in addition to the at least one body portion (e.g., the lungs 108).

Figure 9:
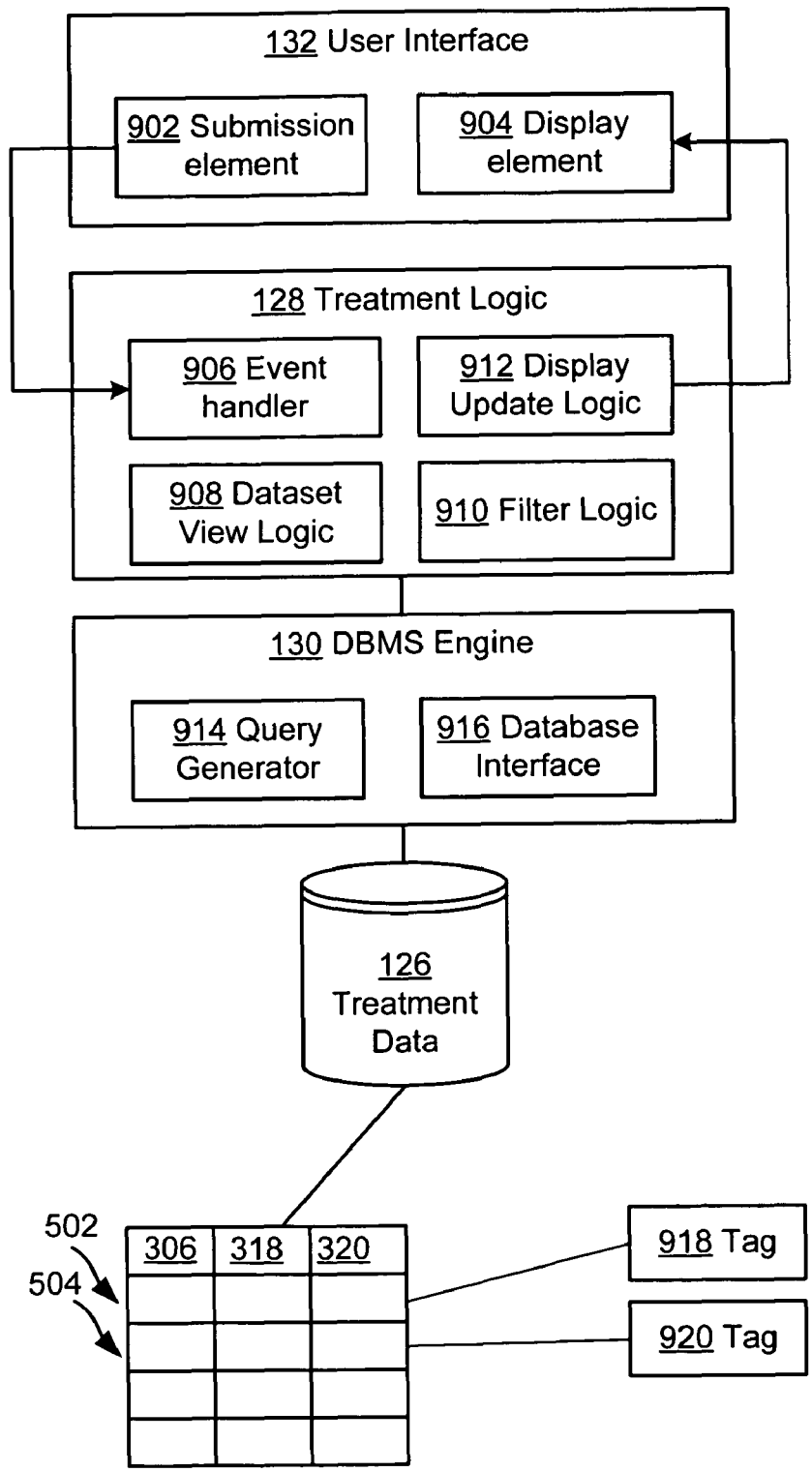
FIG. 9 illustrates an alternative embodiment of the clinical system of FIG. 1 in which the clinical system is configured to provide access to predictive data.

FIG. 9 illustrates an alternative embodiment of the clinical system of FIG. 1 in which the clinical system is configured to provide access to predictive data. Thus, FIG. 9 illustrates examples by which the user interface 132 may be used to access or otherwise interact with the treatment data 126, in order to provide, for example, the various features, functionalities, and effects described above with respect to FIG. 8.

In the example of FIG. 9, the user interface 132 is illustrated as containing generic elements 902 and 904, i.e., a submission element 902 and a display element 904. Generally, the submission element 902 may include any icon, button, field, menu, or box that may be used by the clinician 104 to select, submit, or request information. The display element 904 may include any element of the user interface 132 used to provide information to the clinician 104, where it should be understood that in some cases the submission element 902 and the display element 904 may include the same element, or related elements, since the clinician 104 may enter or select data using a given element and then may view the results of the entry or selection using the same element. Thus, and as should be apparent from FIG. 8, the submission element 902 may include, for example, any of the fields 804, 806, 808, 812, or 814, since the clinician 104 may submit treatment parameters, datasets, and/or filter criteria therewith. Meanwhile, any of the fields 804-814 may be considered to be an example of the display element 904, since any of these may be used to display information (e.g., a result of a selection of a treatment parameter, dataset, or filter criteria). Of course, the graphical illustration 802 is another example of the display element 904.

Thus, for example and as described herein, the clinician 104 may utilize the submission element(s) 902 to select the treatment parameters (or to request a suggestion of one or more treatment parameters), or to specify one or more datasets to be used in providing the possible outcome(s) of using the treatment parameters, or to specify a filter criteria to be used in filtering the dataset(s). For example, when the clinician 104 uses the field 812 to select the dataset "human studies," then this submission is passed to the treatment logic 128, or, more specifically, is passed to an event handler 906 that receives the submission and performs an initial classification, logging, routing, or other handling of the type and value of the submission event, e.g., here, the type including a specification of a dataset to be used and the value including the selected dataset "human studies."

For example, a submission event associated with a use of the submission element 902 by the clinician 104 may be passed by the event handler 906 either to dataset view logic 908 and/or filter logic 910. As described in more detail herein, the dataset view logic 908 and the filter logic 910 represent aspects of the treatment logic 128 associated with analyzing specified treatment parameters with respect to specific portions (e.g., datasets) of the treatment data 126, so as, for example, to provide the uses and effects described above with respect to the graphical illustration 802, e.g., by using display update logic 912 to update the display element(s) 904.

More specifically, for example, the dataset view logic 908 may be used to analyze a submission event from the event handler 906 and determine, for example, that the clinician 104 has selected both "human studies" and "animal studies" using the field 812. The dataset view logic 908 may then interact with a query generator 914 of the DBMS engine 130 to generate a query that may be passed by a database interface 916 to the treatment data 126. In this case, it also may occur that the event handler 906 may pass a second submission event (which may occur concurrently or in a sequence), in which the clinician 104 selects "before 1990" as a filter criteria in the field 814, to the filter logic 910. Thus, the event handler 906 is responsible for correlating the two submission events, so that the filter logic 910 may correspond the specified filter criteria against the (in this case, two) datasets specified to the dataset view logic 908.

In these and other examples, then, the treatment logic 128 may interact with the DBMS engine 130 to construct a query and pass the query to the treatment data 126. For instance, in the example just given, a query may be built that includes a Boolean combination of a first dataset associated with "human studies" AND a second dataset associated with "animal studies," where the query is generated with a form and structure that is appropriate for the treatment data 126 (e.g., using the Structured Query Language (SQL) in a case where the treatment data 126 implements a relational database).

In FIG. 9, example data results and/or datasets are referenced to FIG. 5, where, as shown in FIG. 5, rows 502 and 504 include (abbreviated) data results for a direct end target 306, a target-related, tissue ancestry-correlated binding agent 316, and a treatment agent 320. In this case, for example, data from the row 502 may be associated with a tag 918 indicating that data from the row 502 is associated with human studies and should therefore be included in a first dataset, while data from the row 504 may be associated with a tag 920 indicating that data from the row 504 is associated with animal studies and should therefore be included in a second dataset (where such examples are intended to illustrate a use of the tags 918, 920 with respect to a query from the DBMS engine 130, and are not intended, necessarily, with specific reference to the Oh reference of FIG. 5). In some implementations, for example, the tags 918 and 920 may be associated with use of the extensible Markup Language (XML) in constructing the treatment data 126, where use of XML or other semi-structured databases is discussed in more detail, herein. In this case, then, the database interface 916 may include an XML interface.

It should be understood, then, that the tags 918, 920 may be used in generating and executing queries against the treatment data 126 by either the dataset view logic 908 or the filter logic 910. For example, the filter logic 910 may interact with the query generator 914 to generate a query against the treatment data 126 (or against a result set of a query generated in conjunction with the dataset view logic 908), using the tags 918, 920 to identify, and thereby remove/exclude, data that matches the filter criteria from a corresponding result set.

Once an appropriate result set(s) has been generated by the dataset view logic 908 and/or the filter logic 910, the display update logic 912 may be used to update the display element 904 appropriately, as referenced herein. For example, the display update logic 912 may include logic for implementing the color schemes mentioned above, or for providing any other visual indicator(s) that may be used to convey information in association with the graphical illustration 802.

Figure 10:
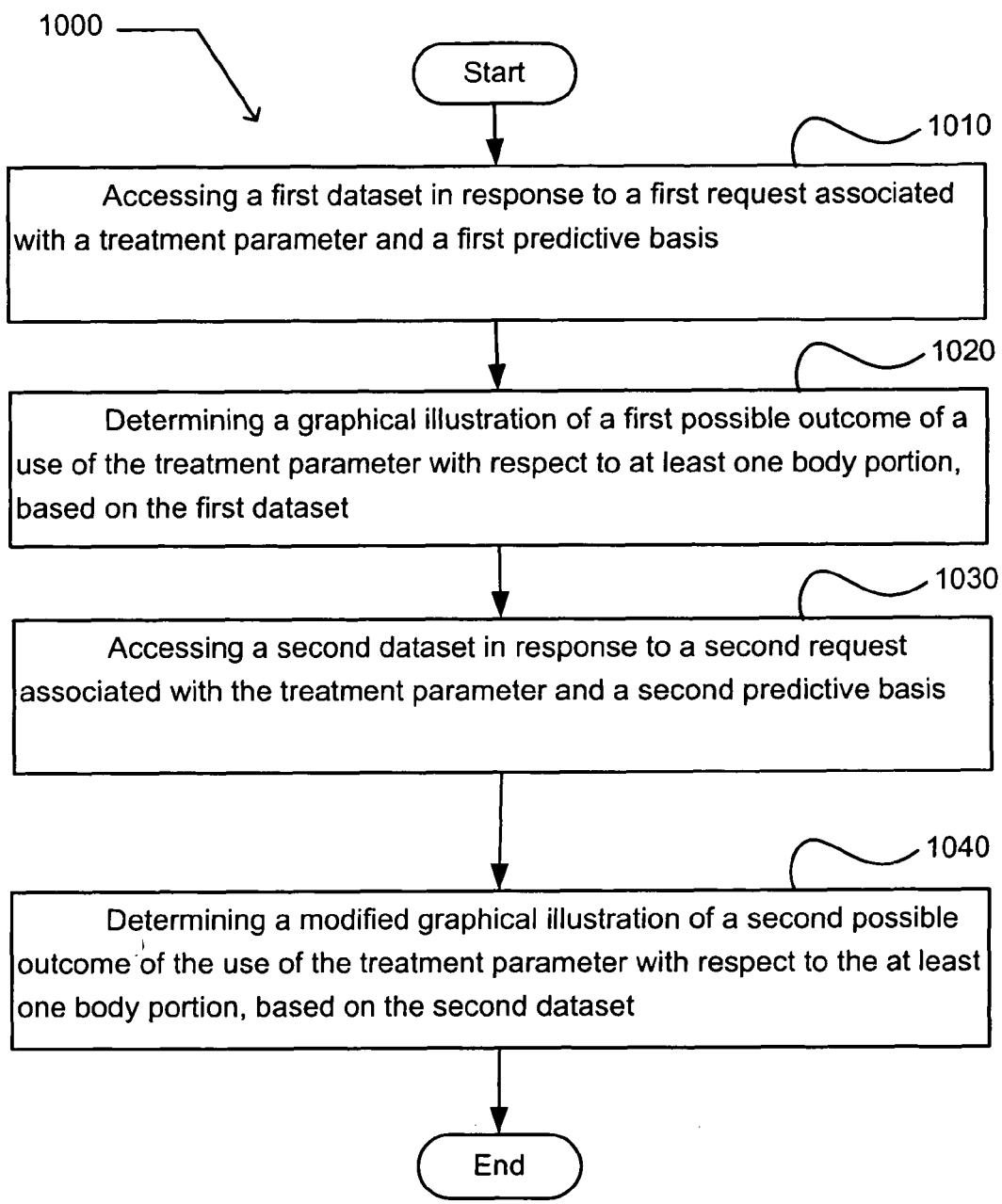
FIG. 10 illustrates an operational flow representing example operations related to accessing predictive data.

FIG. 10 illustrates an operational flow representing example operations related to accessing predictive data. In FIG. 10 and in following figures that include various examples of operational flows, discussion and explanation may be provided with respect to the above-described examples of FIGS. 1-9, and/or with respect to other examples and contexts. However, it should be understood that the operational flows may be executed in a number of other environments and contexts, and/or in modified versions of FIGS. 1-9. Also, although the various operational flows are presented in the sequence(s) illustrated, it should be understood that the various operations may be performed in other orders than those which are illustrated, or may be performed concurrently.

After a start operation, the operational flow 1000 moves to an accessing operation 1010 where a first dataset may be accessed in response to a first request associated with a first treatment parameter and a first predictive basis. For example, as shown in FIG. 9, a first dataset may be accessed from treatment data 126, in response to a first request received from/through the submission element 902 of the user interface 132, where the submission element 902 may include, for example, one or more of the fields 804-814. For example, the first request, as received at the event handler 906 and forwarded to the dataset view logic 908 within the treatment logic 128, may include a treatment agent "radionuclides" specified in the field 806, as well as a first predictive basis (e.g., "human trials") specified in the field 812. Accordingly, and as described herein (e.g., with reference to FIG. 9), the dataset view logic 908 may thus communicate/interface with the DBMS engine 130 to access the treatment data 126 and obtain the (corresponding) first dataset therefrom. In other example implementations, the first request may be acquired from a source other than the user interface 132. For example, the first request may be received as part of, or in association with, a currently-performed procedure, and/or may be acquired from instruments measuring data related to the currently-performed procedure, for example, for a course of treatment of the patient 106 (so that, for example, such data may be used as part of the first request, or as part of a process for generating the first request).

In some implementations, the first request may include the treatment parameter or otherwise be directly associated therewith, while in other example implementations, the first request may be more indirectly associated with the treatment parameter, perhaps through mediation by an additional associated parameter. For example, the first request may include an associated parameter, such as, for example, a diagnostic, symptomatic, screening, preventative, and/or research parameter(s) that may be correlated, e.g., in the treatment data 126 and/or by the treatment logic 128, with a treatment parameter(s).

As a more specific example of such an associated parameter, an inflammation marker may be used to diagnose or recognize an increased risk of certain diseases (e.g., heart disease). Such parameters, in a diagnostic setting, may lead to a diagnosis indicating use of a corresponding treatment parameter(s) to achieve a desired effect (e.g., a corresponding anti-inflammatory treatment agent, which may be delivered to an appropriate bodily location(s) by way of appropriate target-related tissue-ancestry correlated binding site(s), associated target-related tissue-ancestry correlated binding agent(s), and/or treatment agent(s)).

Thus, for example, it should be understood that the user interface 132 and/or the treatment system 102 may be used by the clinician 104 with little or no external reference to the treatment parameters/treatment characteristics 302-320 of FIGS. 3-7 being visible to, or directly used by, the clinician 104. For example, the user interface 132 may present (and/or allow the clinician 104 to specify) a particular illness, and corresponding (suggested) medical procedure(s), where such illness(es) and procedures may be related/applicable to one another through application of, for example, appropriately-selected target-related tissue-ancestry correlated binding site(s) and target-related tissue-ancestry correlated binding agent(s). In such cases, then, the treatment system 102 acts transparently, so that the clinician 104 need not consider, or even be aware of, these particular mechanisms underlying the suggested procedure(s), and, instead, may simply be provided by the user interface 132 with a suggested procedure (and indicated efficacy thereof) for a specified illness.

Then, in a determining operation 1020, a graphical illustration of a first possible outcome of a use of the treatment parameter with respect to at least one body portion may be determined, based on the first dataset. For example, the dataset view logic 908 may determine the first possible outcome of a use of the treatment agent specified in the field 806 (and included in the first request), based on the first dataset, where the first possible outcome may include, for example, an efficacy of the treatment agent on a direct end target as the at least one body portion (e.g., on "cancer cells in lung," as may be specified in the field 804 and/or included in the first request), and/or a risk, side effect, or consequence of the treatment agent on the at least one body portion, or on at least one other body portion (e.g., the pancreas 110). Then, continuing the example, the dataset view logic 908 may determine, perhaps in conjunction with the display update logic 912, the graphical illustration, e.g., the graphical illustration 802 of at least a portion of a human body in which the lungs 108 and/or pancreas 110 (or portions thereof) are included. In determining the graphical illustration, the various effects described herein may be employed, e.g., coloring, highlighting, or otherwise visually indicating the at least one body portion in order to indicate or convey the first possible outcome (e.g., a degree of brightness corresponding to a degree of efficacy or risk associated with the treatment agent). As should be apparent, then, the graphical illustration 802 may be provided using the user interface 132, e.g., by updating the display element 904 accordingly.

As described herein, the first possible outcome may thus be based on a first dataset that may be specified, for example, using the field 812, where the first predictive basis may correspond to the first dataset and may be pre-configured, defined, or characterized (e.g., as being either relatively more or less predictively useful than a comparison dataset). Although the graphical illustration 802 includes specific body portions such as the lungs 108 and pancreas 110, it should be understood that the graphical illustration 802 may be determined with respect to an entire body of the patient 106 (e.g., where the treatment parameter includes a blood pressure or other characteristic of the patient 106 that is not localized to a particular body portion), and/or may be determined as an additional or alternative representation of data (e.g., as a blood pressure chart illustrated along with, or as some or all of, the graphical illustration 802).

In an accessing operation 1030, a second dataset may be accessed in response to a second request associated with the treatment parameter and a second predictive basis. For example, the dataset view logic 908, as just described, may receive the second request from the event handler 906 and/or the submission element(s) 902, where the second request may include the same treatment parameter (e.g., the treatment agent "radionuclides" specified in the field 806), but a different, or second, predictive basis (e.g., "animal studies," as specified in the field 812). Accordingly, the resulting accessing of the treatment data 126 may result in the accessing of an additional/alternative, or second, dataset therefrom.

Then, in a determining operation 1040, a modified graphical illustration of a second possible outcome of the use of the treatment parameter with respect to the at least one body portion may be determined, based on the second dataset. For example, and continuing the example(s) just given with respect to the operations 1010-1030, the dataset view logic 908 may determine the second possible outcome as including an efficacy of the treatment agent (e.g., "radionuclides") on the at least one body portion (e.g., the direct end target "cancer cells in lung"), as predicted by the second predictive basis (e.g., "animal studies"), based on the second dataset. Then, the modified graphical illustration (e.g., a modified version of the graphical illustration 802) may be determined, including a corresponding/modified altering, coloring, or indicating of the at least one body portion.

As a result, for example, the clinician 104 may first specify the treatment parameter(s) of the fields 804-810, as well as one or more predictive bases of the field 812, and the treatment logic 128 and the treatment data 126 may be used to generate the first possible outcome, accordingly (e.g., may illustrate the lungs 108 (or portion thereof) with a first level of brightness or shade of color). Then, for the clinician's use and consideration, the clinician 104 may specify a second predictive basis and view a corresponding, second possible outcome. In this way, and as described in more detail herein, the clinician 104 may view a range of possible outcomes, based on a number of different types of predictive bases, where the various predictive bases may be characterized as being more or less predictively useful relative to one another. Accordingly, an ability of the clinician 104 to diagnose and treat patients may be improved.

In this regard, it should be understood that the operation(s) 1010-1040 may be performed with respect to a digital representation (e.g., as digital data), for example, of the treatment parameter, the dataset(s), and/or the filter criteria (e.g., the filter criteria of the field 814). For example, as may be understood with reference to FIGS. 9 and 10, the treatment logic 128 may accept a digital or analog (for conversion into digital) representation of the at least one treatment parameter from the user interface 132 (e.g., from the submission element 902), for presentation to the DBMS engine 130 and/or the treatment data 126. As another example, the treatment logic 128 may provide a digitally-encoded representation of the graphical illustration 802, or a modified version thereof, based on the treatment data 126, where the treatment data 126 may be implemented and accessed locally, and/or may be implemented and accessed remotely.

Thus, an operation(s) may be performed related either to a local or remote storage of the digital data, or to another type of transmission of the digital data. As discussed herein, in addition to accessing, querying, recalling, or otherwise obtaining the digital data for the providing operation, operations may be performed related to storing, assigning, associating, or otherwise archiving the digital data to a memory, including, for example, sending and/or receiving a transmission of the digital data from a remote memory. Accordingly, any such operation(s) may involve elements including at least an operator (e.g., either human or computer) directing the operation, a transmitting computer, and/or a receiving computer, and should be understood to occur within the United States as long as at least one of these elements resides in the United States.

Figure 11:
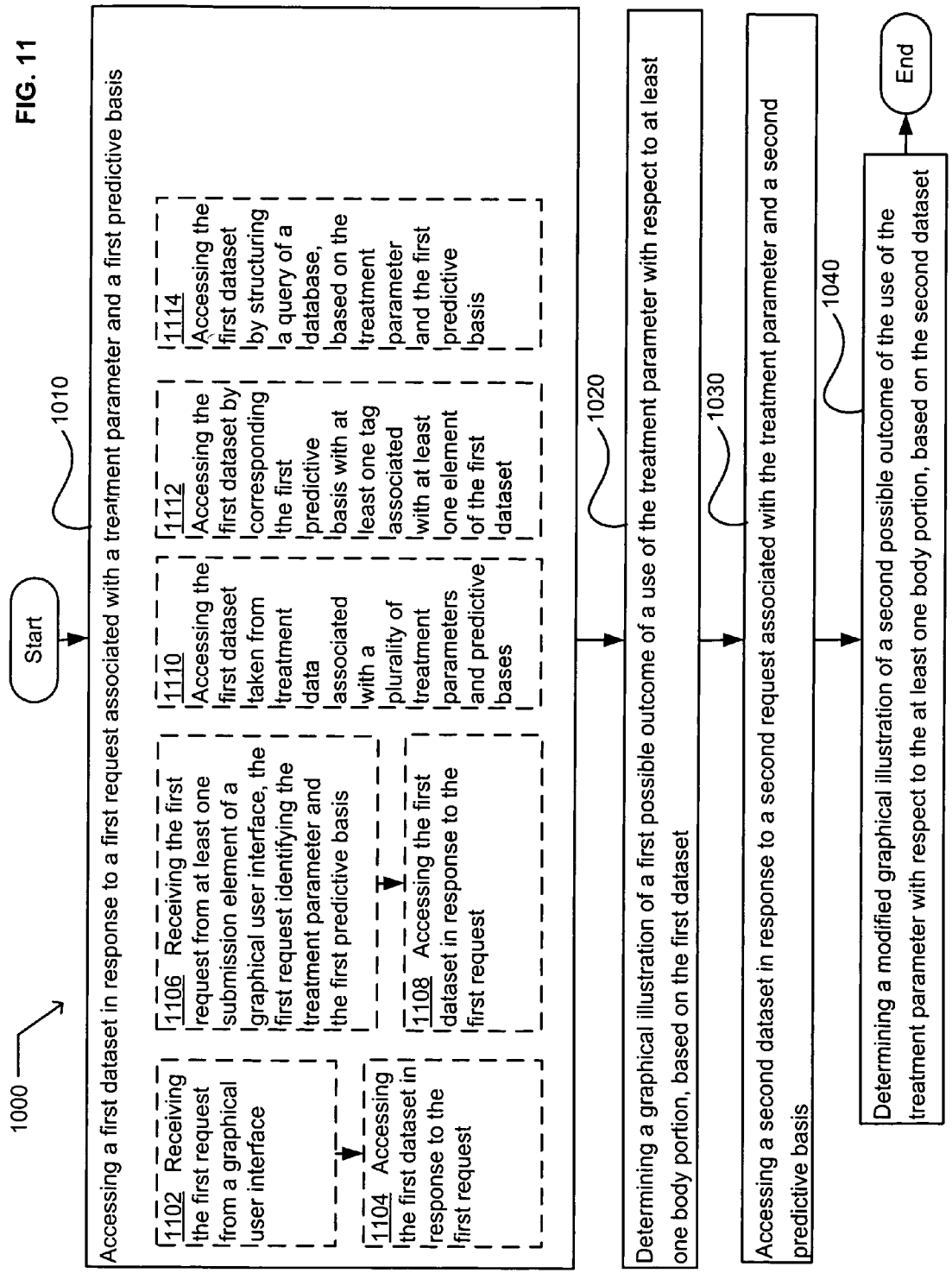
FIG. 11 illustrates an alternative embodiment of the example operational flow of FIG. 10.

FIG. 11 illustrates alternative embodiments of the example operational flow 1000 of FIG. 10. FIG. 11 illustrates example embodiments where the accessing operation 1010 may include at least one additional operation. Additional operations may include operation 1102, operation 1104, operation 1106, operation 1108, operation 1110, operation 1112, and/or operation 1114.

At the operation 1102, the first request may be received from a graphical user interface. For example, the first request (e.g., from the clinician 104) may be received for the graphical illustration 802, using the user interface 132, where, as already discussed, the first request may include or specify the first treatment parameter and the first predictive basis. Then, at the operation 1104, the first dataset may be accessed in response to the first request. For example, the treatment logic 128, e.g., the dataset view logic 908, may access the first dataset from the treatment data 126.

At the operation 1106, the first request may be received from at least one submission element of a graphical user interface, the first request identifying the treatment parameter and the first predictive basis. For example, the first request may be received from the submission element 902 of the user interface 132, where the submission element 902 may include, for example, one or more of the fields 804-814. Then, at the operation 1108, the first dataset may be accessed in response to the first request. For example, as described herein, the treatment logic 128, e.g., the dataset view logic 908, may access the first dataset from the treatment data 126.

At the operation 1110, the first dataset may be accessed by being taken from treatment data associated with a plurality of treatment parameters and predictive bases. For example, the first dataset may be accessed from within the treatment data 126, which, as described herein, may include treatment data such as is also described herein, for example, with respect to FIGS. 5-7, where various examples of treatment parameters 302-320 (and instances thereof) are provided (and where, as noted herein, the various examples of treatment parameters 302-320 also may be referred to as, or considered to be, treatment characteristics or treatment information). Elements of the treatment data 126 may be associated with one or more predictive bases, for accessing of the first dataset based thereon, e.g., by, for example, associating elements of the treatment data with one or more of the tag(s) 918, 920. In this way, the dataset view logic 908 may correspond the first predictive basis of the first request with elements of the treatment data 126, i.e., with elements of the first dataset.

At the operation 1112, the first dataset may be accessed by corresponding the first predictive basis with at least one tag associated with at least one element of the first dataset. For example, and as just referenced, the dataset view logic 908 may correspond the first predictive basis of the first request with one or more of the tag(s) 918, 920, which may include, for example, XML tags associated with element(s) of the treatment data 126, thereby to identify, and thus access, a plurality of data elements that may then be aggregated into the first dataset. As used herein, the term corresponding may refer to, or include, any associating, coupling, relating, and/or matching operation performed with respect to two or more specified elements (e.g., between the first predictive basis and the at least one tag, as just described).

At the operation 1114, the first dataset may be accessed by structuring a query of a database, based on the first treatment parameter and the first predictive basis. For example, the dataset view logic 908 may interact/interface with the DBMS engine 130 (e.g., with the query generator 914) to structure a query of the treatment data 126. For example, SQL or SQL-like operations using the specific (instance of the) treatment parameter of the first request may be performed, and/or Boolean operations using (at least) the first treatment parameter and (at least) the first predictive basis may be performed.

Figure 12:
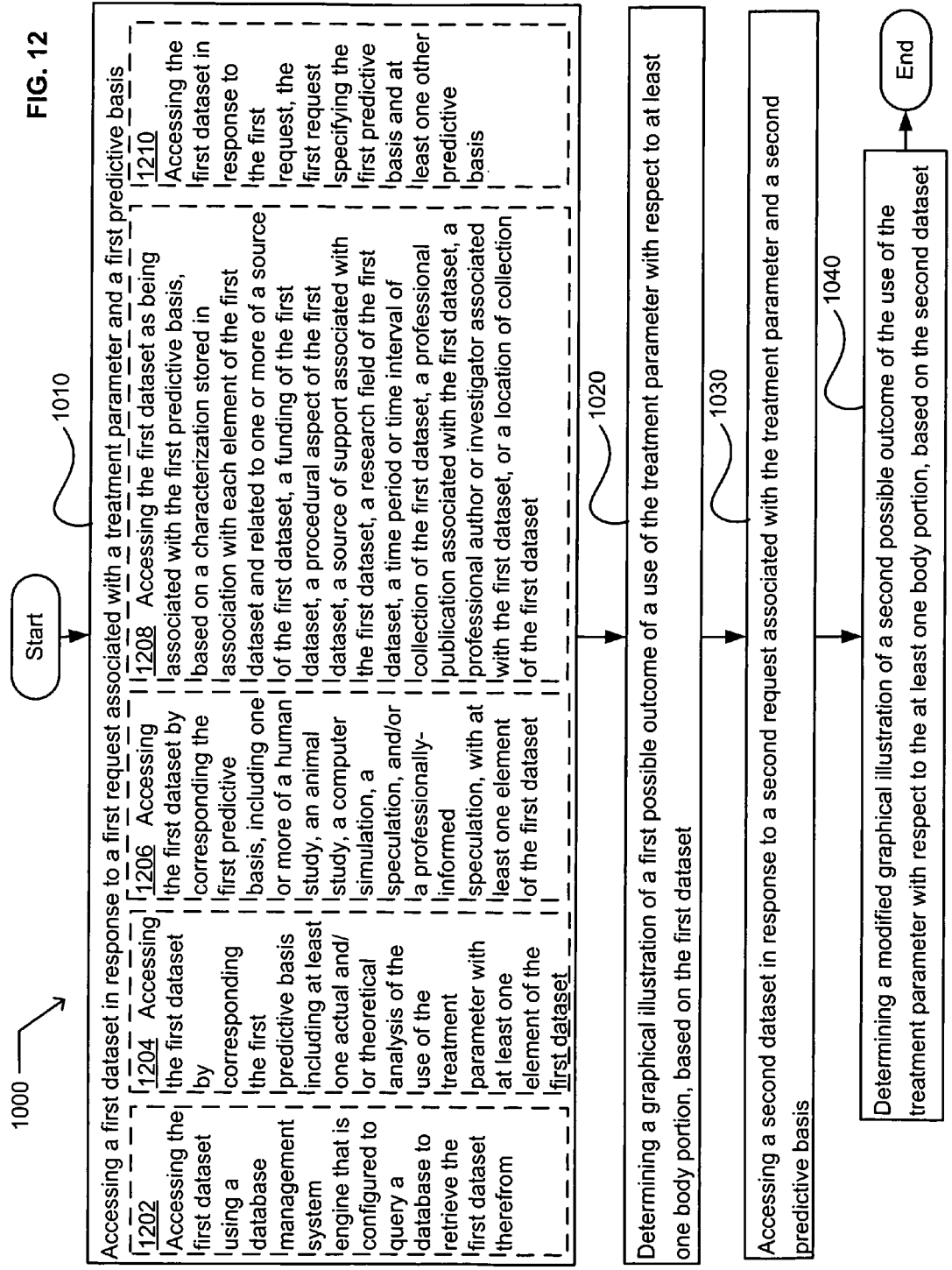
FIG. 12 illustrates an alternative embodiment of the example operational flow of FIG. 10.

FIG. 12 illustrates alternative embodiments of the example operational flow 1000 of FIG. 10. FIG. 12 illustrates example embodiments where the accessing operation 1010 may include at least one additional operation. Additional operations may include operation 1202, operation 1204, operation 1206, operation 1208, and/or operation 1210.

At the operation 1202, the first dataset may be accessed using a database management system engine that is configured to query a database to retrieve the first dataset therefrom. For example, the DBMS engine 130 may be used to query a relational or object-oriented database including the treatment data 126, so that elements of the treatment data 126 may be identified, retrieved, and aggregated as the first dataset.

At the operation 1204, the first dataset may be accessed by corresponding the first predictive basis including at least one actual and/or theoretical analysis of the use of the treatment parameter with at least one element of the first dataset. For example, the dataset view logic 908 may access the treatment data 126 based on the first request, where the first request may be received from the user interface 132 based on a selection of one of the values of the field 812, so that the first request includes or is associated with an actual analysis (e.g., human studies or animal studies, or any in vivo or in vitro study) and/or a theoretical analysis (e.g., in silico and/or computer simulations, or speculation).

At the operation 1206, the first dataset may be accessed by corresponding the first predictive basis, including one or more of a human study, an animal study, a computer simulation, a speculation, and/or a professionally-informed speculation, with at least one element of the first dataset. For example, the dataset view logic 908 may correspond to the first predictive basis of the first request, as received from the field 812, with each element of the first dataset as accessed from the treatment data 126, where the field 812 is used to specify human studies, animal studies, or any of the other predictive bases included therein, or other predictive bases that may be provided, or combinations thereof.

At the operation 1208, the first dataset may be accessed as being associated with the first predictive basis, based on a characterization stored in association with each element of the first dataset and related to one or more of a source of the first dataset, a funding of the first dataset, a procedural aspect of the first dataset, a source of support associated with the first dataset, a research field of the first dataset, a time period or time interval of collection of the first dataset, a professional publication associated with the first dataset, a professional author or investigator associated with the first dataset, or a location of collection of the first dataset. For example, the first dataset may be characterized by a source of funding of the research that supplied the results of the first dataset, where, for example, a certain funding source may be associated with a higher (net) predictive value than others. Similarly, a research field associated with the first dataset (e.g., oncology or hematology) may be associated with, or characterized as, having a greater or lesser predictive value, e.g., through use of the tags 918, 920, or using other data characterization techniques.

At the operation 1210, the first dataset may be accessed in response to the first request, the first request specifying the first predictive basis and at least one other predictive basis. For example, the dataset view logic 908 may access the first dataset specified in the field 812 (e.g., from the treatment data 126) as being associated with the first predictive basis, such as, for example, "human studies," where results from at least one other dataset may be included in the first dataset having another predictive basis, such as "animal studies." In other words, results from different studies, datasets, and/or predictive bases may be combined when accessing the first dataset, so that, as described herein, the clinician 104 may consider such combinations when deciding on a diagnosis, treatment, or course of research. In this regard, and as described in more detail herein, it should be understood that in many cases, a predictive basis of "human studies" may be assumed to be more predictively useful than a predictive basis of "animal studies" in the context of deciding diagnosis, treatment, or research for human patients. More generally, however, a predictive basis and/or a relative predictive value thereof may be assigned or associated with results, data, or datasets within the treatment data 126, prior to a use of the user interface 132 by the clinician 104, using, e.g., the tags 918 and 920, or similar techniques. That is, in some implementations, different predictive bases may be objectively and verifiably designated as having a defined relative value of predictive usefulness (e.g., relative to one another). Accordingly, one skilled in the art would appreciate that no subjectivity is involved in providing the graphical illustration 802 (as described herein) based on the different predictive bases, as those predictive bases may be provided in associated software, hardware, and/or firmware. Of course, the graphical illustration 802 may nonetheless have more or less subjective value to the clinician 104, based on a personal value or judgment of the clinician 104. Moreover, in some implementations, characterizations of the predictive bases may be universal through the treatment data 126, so that, for example, all human studies of a certain type are associated with a first predictive basis or value. In other implementations, such characterizations may be assigned by, or determined for, individual clinicians. For example, different clinicians may assign different predictive values to different (types of) datasets. In still other implementations, an artificial intelligence engine may be used to make semantic decisions regarding assessment(s) of the relative predictive value or usefulness of the different predictive bases.

Figure 13:
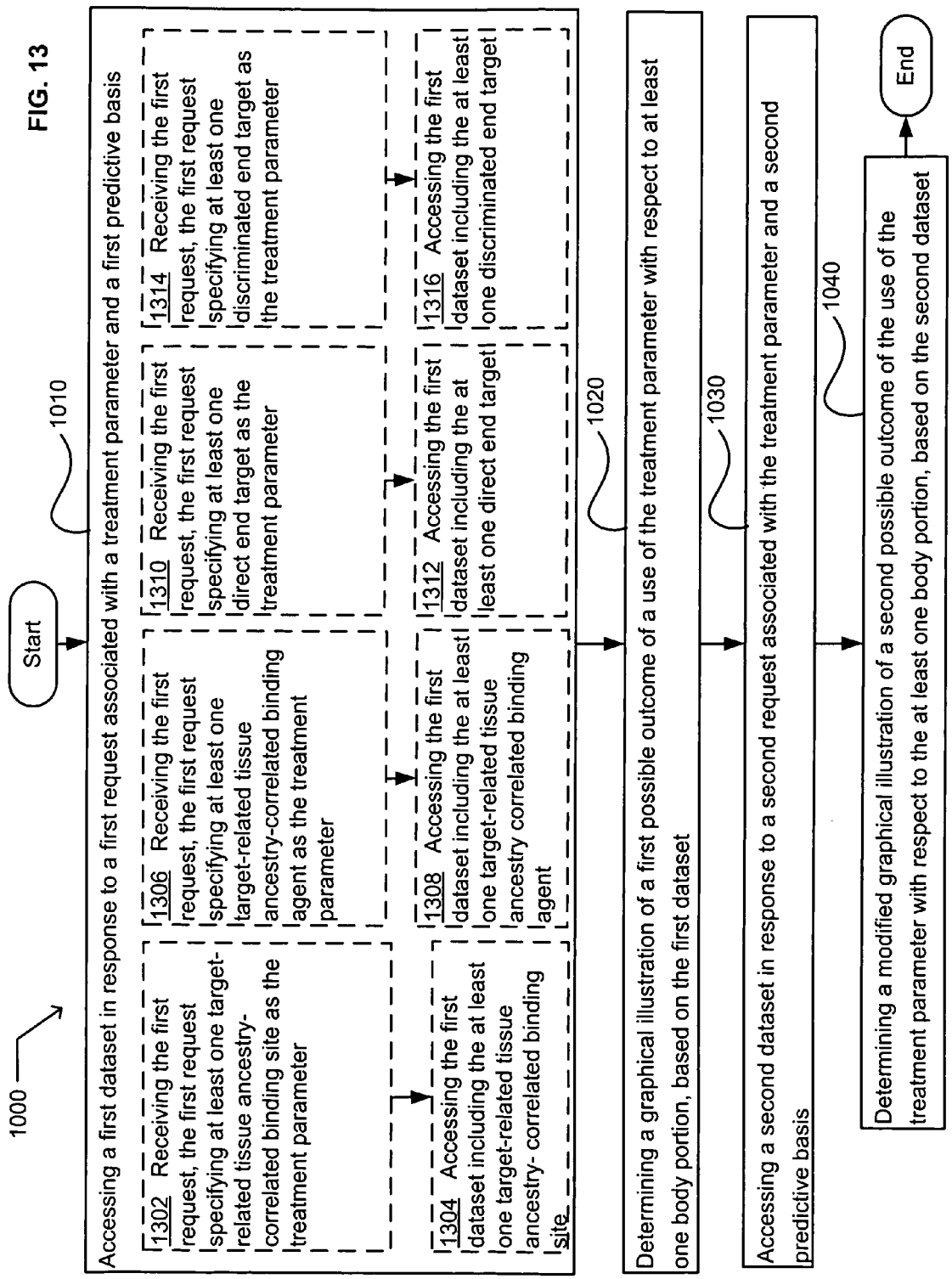
FIG. 13 illustrates an alternative embodiment of the example operational flow of FIG. 10.

FIG. 13 illustrates alternative embodiments of the example operational flow 1000 of FIG. 10. FIG. 13 illustrates example embodiments where the accessing operation 1010 may include at least one additional operation. Additional operations may include operation 1302, operation 1304, operation 1306, operation 1308, operation 1310, operation 1312, operation 1314, and/or operation 1316.

At the operation 1302, the first request may be received, the first request specifying at least one target-related tissue ancestry-correlated binding site as the treatment parameter. For example, the dataset view logic 908 may receive the first request from the user interface 132 (e.g., from a field similar to the fields 804-810, or through another submission element 902, wherein the treatment parameter includes, for example, at least one protein induced and/or expressed at an interface (e.g., the endothelial layer 118) between tissue and/or blood and/or a blood component in the vicinity of the at least one body portion as the at least one target-related tissue ancestry-correlated binding site. Then, at the operation 1304, the first dataset may be accessed including the at least one target-related tissue ancestry-correlated binding site. For example, the treatment logic 128, e.g., the dataset view logic 908, may access the first dataset, including the at least one target-related tissue ancestry-correlated binding site, from the treatment data 126.

At the operation 1306, the first request may be received, the first request specifying at least one target-related tissue ancestry-correlated binding agent as the treatment parameter. For example, the dataset view logic 908 may receive the first request from the user interface 132 (e.g., by way of the field(s) 808 and/or 810). The at least one target-related tissue ancestry-correlated binding agent may include, for example, an I-labeled monoclonal antibody that is known to target and bind to a corresponding target-related tissue ancestry-correlated binding site. Then, at the operation 1308, the first dataset may be accessed including the at least one target-related tissue ancestry-correlated binding agent. For example, the treatment logic 128, e.g., the dataset view logic 908, may access the first dataset, including the at least one target-related tissue ancestry-correlated binding agent, from the treatment data 126.

At the operation 1310, the first request may be received, the first request specifying at least one direct end target as the treatment parameter. For example, the dataset view logic 908 may receive the first request from the user interface 132 (e.g., from the field 804). For example, the direct end target may include the lungs 108, and/or cancerous cells thereof, as the at least one direct end target. Then, at the operation 1312, the first dataset may be accessed including the at least one direct end target. For example, the treatment logic 128, e.g., the dataset view logic 908, may access the first dataset, including the at least one direct end target, from the treatment data 126.

At the operation 1314, the first request may be received, the first request specifying at least one discriminated end target as the treatment parameter. For example, although not illustrated in FIG. 8, the dataset view logic 908 may receive the first request, including an identification of the discriminated end target as the treatment parameter, from a corresponding field of the user interface 132 (not illustrated in FIG. 8). For example, the discriminated end target may include non-lung tissue/organ(s) (e.g., the pancreas 110), and/or non-cancerous lung tissue. Then, at the operation 1316, the first dataset may be accessed including the at least one discriminated end target. For example, the treatment logic 128, e.g., the dataset view logic 908, may access the first dataset, including the at least one discriminated end target, from the treatment data 126.

Figure 14:
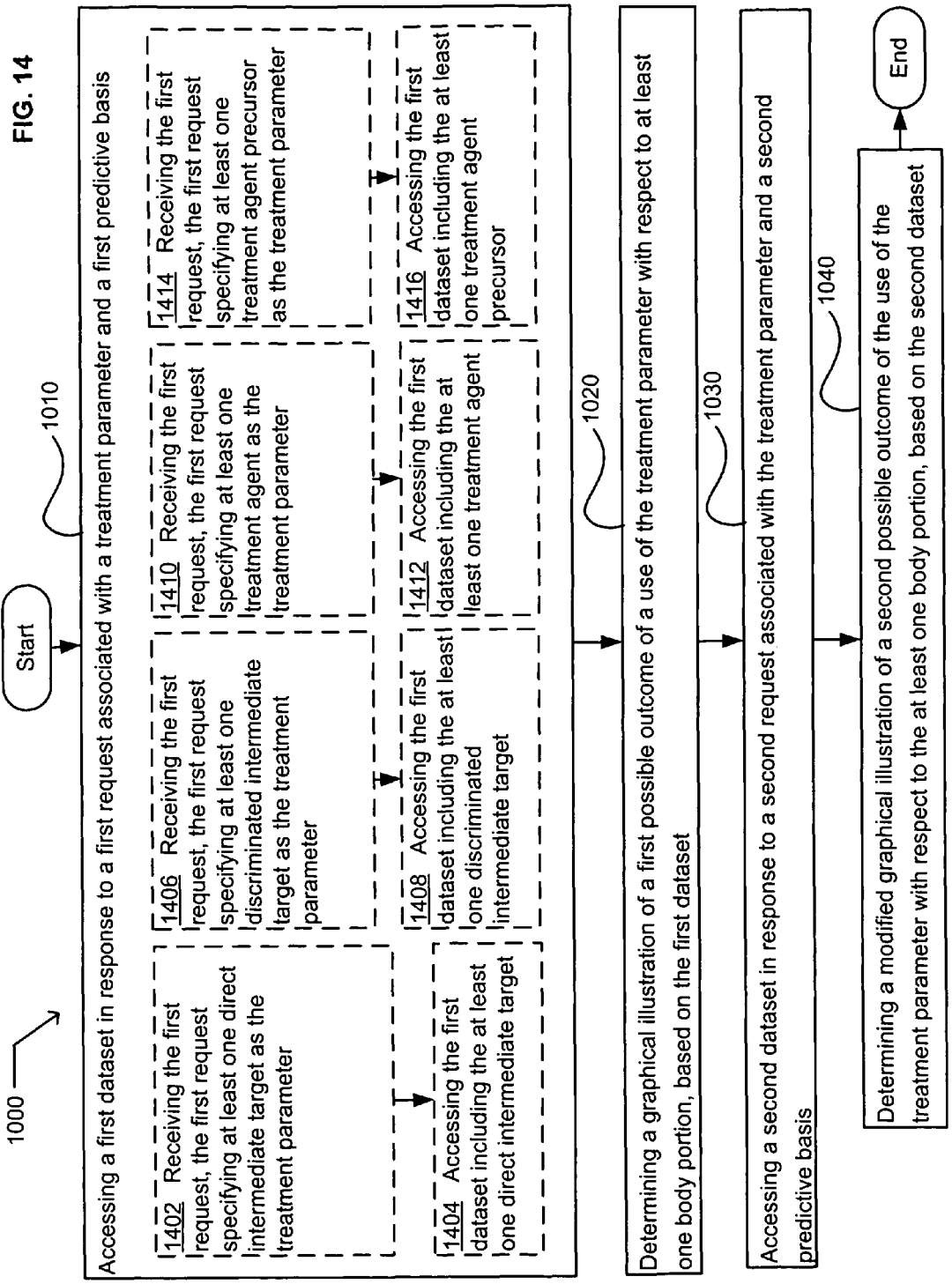
FIG. 14 illustrates an alternative embodiment of the example operational flow of FIG. 10.

FIG. 14 illustrates alternative embodiments of the example operational flow 1000 of FIG. 10. FIG. 14 illustrates example embodiments where the accessing operation 1010 may include at least one additional operation. Additional operations may include operation 1402, operation 1404, operation 1406, operation 1408, operation 1410, operation 1412, operation 1414, and/or operation 1416.

At the operation 1402, the first request may be received, the first request specifying at least one direct intermediate target as the treatment parameter. For example, the direct intermediate target may be specified using a field (not shown) of FIG. 8. For example, the direct intermediate target may include endothelial tissue proximate to (e.g., cancerous) lung tissue. Then, at the operation 1404, the first dataset may be accessed including the at least one direct intermediate target. For example, the treatment logic 128, e.g., the dataset view logic 908, may access the first dataset, including the at least one direct intermediate target, from the treatment data 126.

At the operation 1406, the first request may be received, the first request specifying at least one discriminated intermediate target as the treatment parameter. For example, the discriminated intermediate target may be specified using a field (not shown) of FIG. 8. For example, the discriminated intermediate target may include endothelial tissue proximate to non-lung tissue (e.g., endothelial tissue proximate to the pancreas 110). Then, at the operation 1408, the first dataset may be accessed including the at least one discriminated intermediate target. For example, the treatment logic 128, e.g., the dataset view logic 908, may access the first dataset, including the at least one discriminated intermediate target, from the treatment data 126.

At the operation 1410, the first request may be received, the first request specifying at least one treatment agent as the treatment parameter. For example, the at least one treatment agent may be received at the dataset view logic 908 by way of the field 806. For example, the treatment agent may include radionuclides that are associated with cancer cells in the lung through a desired course of treatment. Then, at the operation 1412, the first dataset may be accessed including the at least one treatment agent. For example, the treatment logic 128, e.g., the dataset view logic 908, may access the first dataset, including the at least one treatment agent, from the treatment data 126.

At the operation 1414, the first request may be received, the first request specifying at least one treatment agent precursor as the treatment parameter. For example, the treatment agent precursor may be specified using a field (not shown) of FIG. 8. For example, the treatment agent precursor may include an agent used to facilitate application of a treatment agent, e.g., an immune-response element that is used to identify/mark/bond with a target-related tissue ancestry-correlated binding site and/or a substance that when metabolized becomes the treatment agent, such as with pro-drugs. Then, at the operation 1416, the first dataset may be accessed including the at least one treatment agent precursor. For example, the treatment logic 128, e.g., the dataset view logic 908, may access the first dataset, including the at least one treatment agent precursor, from the treatment data 126.

Figure 15:
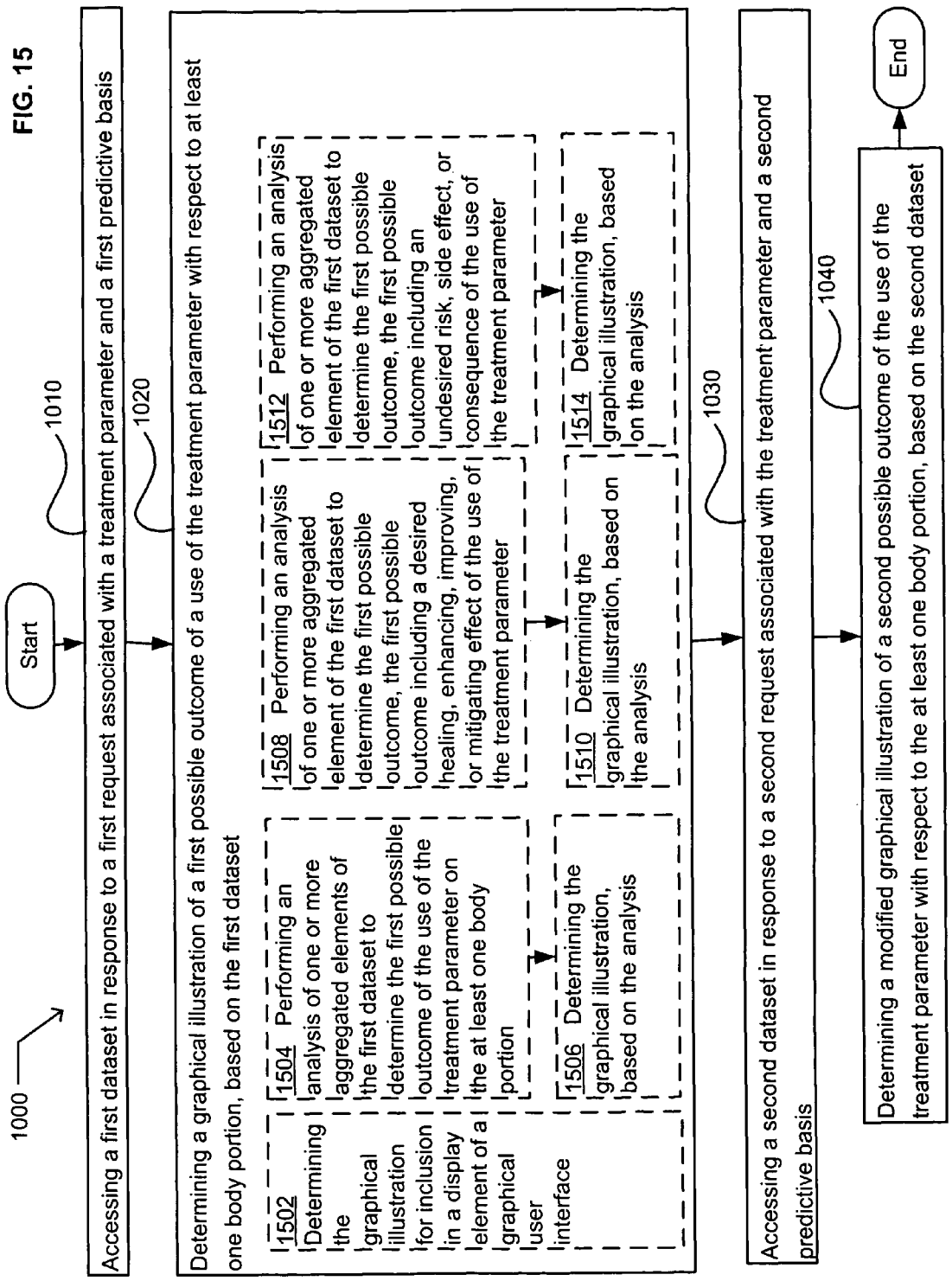
FIG. 15 illustrates an alternative embodiment of the example operational flow of FIG. 10.

FIG. 15 illustrates alternative embodiments of the example operational flow 1000 of FIG. 10. FIG. 15 illustrates example embodiments where the determining operation 1020 may include at least one additional operation. Additional operations may include operation 1502, operation 1504, operation 1506, operation 1508, operation 1510, operation 1512, and/or operation 1514.

At the operation 1502, the graphical illustration may be determined for inclusion in a display element of a graphical user interface. For example, the dataset view logic 908 and/or the display update logic 912 may determine the graphical illustration 802 for inclusion in the display element 904 of the graphical user interface 132.

At the operation 1504, an analysis of one or more aggregated elements of the first dataset may be performed to determine the first possible outcome of the use of the treatment parameter on the at least one body portion. For example, as described herein, the first possible outcome may include an efficacy of the binding agent of the field(s) 808/810 of FIG. 8 in delivering the treatment agent "radionuclides" specified in the field 806 to the direct end target "cancer cells in lung" specified in the field 804 (and/or an efficacy of the radionuclides in reducing or destroying the cancer cells). The first possible outcome may be determined based on, for example, aggregated elements of the first dataset. For example, if the first predictive basis includes "human trials," the first dataset may include data elements derived from a plurality of human trials, so that the dataset view logic 908 may be required to aggregate the data elements accordingly, so that an analysis thereof may be performed to derive the first possible outcome. Similarly, the first predictive basis may include "human trials" and "animal studies," so that the first dataset may include data elements derived from a plurality of human trials and a plurality of animal studies. Again, the dataset view logic 908 may be required to aggregate all such data elements accordingly, and perform a corresponding analysis thereof, to derive the first possible outcome. Then, at the operation 1506, the graphical illustration may be determined, based on the analysis. For example, the dataset view logic 908 and/or the display update logic 912 may determine the graphical illustration 802 including the lungs 108, where the lungs 108 and/or a portion thereof may be visually highlighted within the graphical illustration 802, perhaps with a color or degree of intensity determined to correspond to the determined efficacy of the treatment agent.

At the operation 1508, an analysis of one or more aggregated elements of the first dataset may be performed to determine the first possible outcome, the first possible outcome including a desired healing, enhancing, improving, or mitigating effect of the use of the treatment parameter. For example, as just described, elements of the first dataset may be aggregated by the dataset view logic 908, and an analysis thereof may be performed to determine the first possible outcome, including, for example, an improving of the lungs 108 by reduction or removal of the cancer cells therefrom. Then, at the operation 1510, the graphical illustration may be determined, based on the analysis. For example, as just described, the dataset view logic 908 and/or the display update logic 912 may determine the graphical illustration 802 including the lungs 108, where the lungs 108 and/or a portion thereof may be visually highlighted within the graphical illustration 802, perhaps with a color or degree of intensity determined to correspond to the determined efficacy of the treatment agent.

At the operation 1512, an analysis of one or more aggregated elements of the first dataset may be performed to determine the first possible outcome, the first possible outcome including an undesired risk, side effect, or consequence of the use of the treatment parameter. For example, the dataset view logic 908 may perform an analysis of aggregated elements of the first dataset as accessed from the treatment data 126, to determine an undesired side effect (e.g., damage to the pancreas 110) of the use of the treatment parameter (e.g., the treatment agent "radionuclides"). Then, at the operation 1514, the graphical illustration may be determined, based on the analysis. For example, the dataset view logic 908 and/or the display update logic 912 may determine the graphical illustration 802 including the pancreas 110, where the pancreas 110 and/or a portion thereof may be visually highlighted within the graphical illustration 802.

Figure 16:
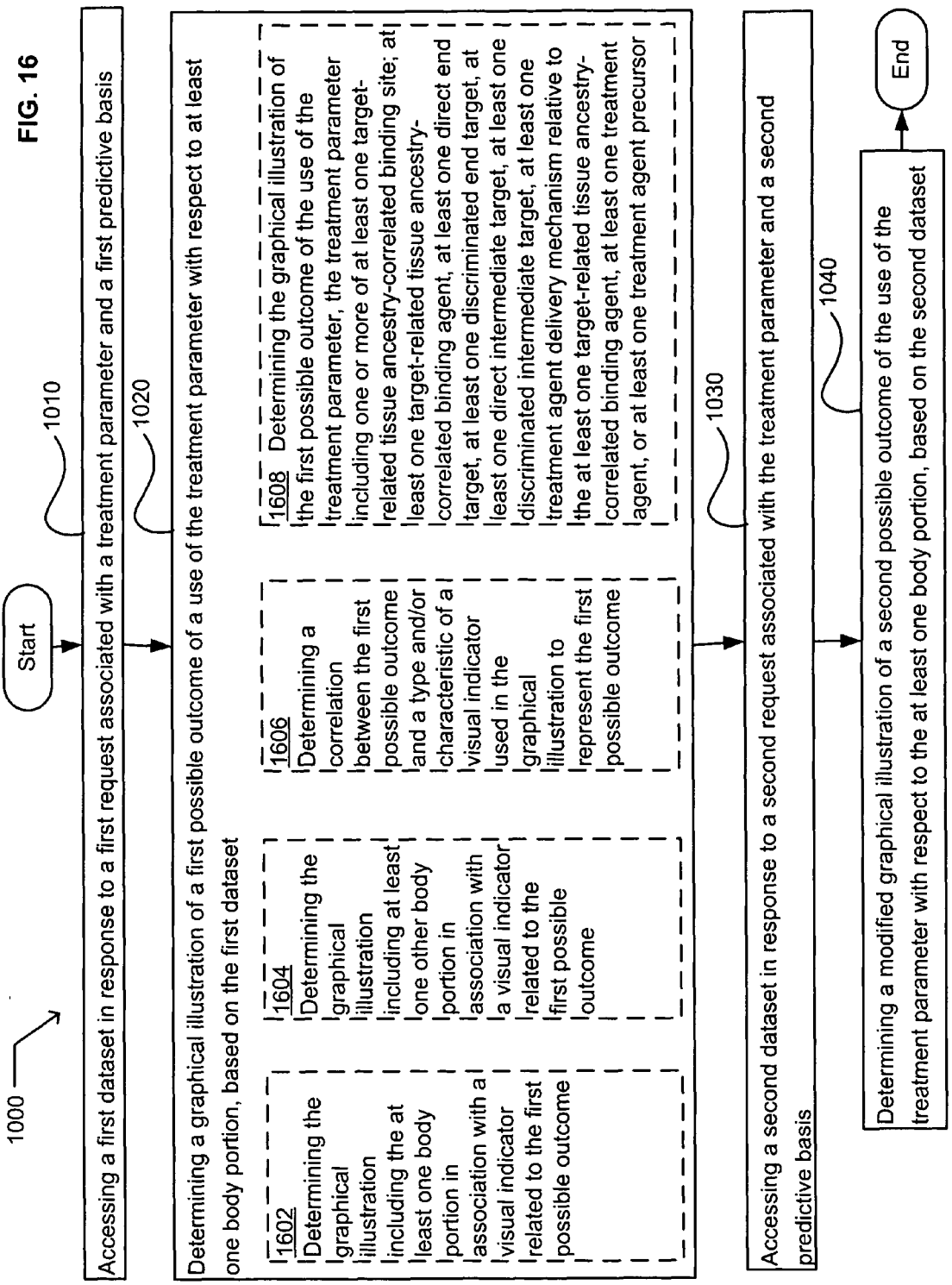
FIG. 16 illustrates an alternative embodiment of the example operational flow of FIG. 10.

FIG. 16 illustrates alternative embodiments of the example operational flow 1000 of FIG. 10. FIG. 16 illustrates example embodiments where the determining operation 1020 may include at least one additional operation. Additional operations may include operation 1602, operation 1604, operation 1606, and/or operation 1608.

At the operation 1602, the graphical illustration may be determined including the at least one body portion in association with a visual indicator related to the first possible outcome. For example, the dataset view logic 908 and/or the display update logic 912 may determine the graphical illustration 802 including the lungs 108, pancreas 110, or other body portion, where the mere inclusion of such a body portion may be considered to be a visual indicator related to the first possible outcome (e.g., where the pancreas 110 is illustrated only when it is determined that possible side effects may be associated with the pancreas 110 when using the lungs 108 (or cancerous cells therein) as a direct end target). In other implementations, and as referenced herein, the visual indicator may include a coloring, highlighting, designating, marking, identifying, shading, cross-hatching, flashing, or other visual effect. In such examples, the visual indicator(s) may be related to, or indicate, the first possible outcome, e.g., the efficacy (or risks, or unwanted consequences) of one or more (combinations of) treatment parameters. For example, the graphical illustration 802 or appropriate portion(s) thereof may have its color changed, or may be highlighted or otherwise marked/designated to indicate a level of efficacy of selected treatment parameter(s). For example, an efficacy of each treatment parameter may be shown individually or together, since, for example, an efficacy of the target-related, tissue ancestry-correlated binding agent of the field 808 may refer to an ability of such an agent to deliver any treatment agent to (a corresponding target-related, tissue ancestry-correlated binding site within) a direct end target of the field 804, irrespective of which treatment agent is associated therewith. Meanwhile, an efficacy of the treatment agent of the field 806 may refer to an actual treatment result (e.g., reduction or destruction of cancer cells), and, in another example, an efficacy of the combination of treatment parameters may refer to an overall success of the treatment, including management or reduction of associated risks and side effects.

At the operation 1604, the graphical illustration may be determined as including at least one other body portion in association with a visual indicator related to the first possible outcome. For example, the dataset view logic 908 and/or the display update logic 912 may determine the graphical illustration 802 including the pancreas 110 as the at least one other body portion, when, for example, the lungs 108 may be included as the at least one body portion.

At the operation 1606, a correlation may be determined between the first possible outcome and a type and/or characteristic of a visual indicator used in the graphical illustration to represent the first possible outcome. For example, the dataset view logic 908 and/or the display update logic 912 may determine that the first possible outcome includes a particularly effective (or ineffective) use of the treatment agent "radionuclides" in treating the direct end target "cancer cells in lung." In this case, the dataset view logic 908 and/or the display update logic 912 also may determine how this first possible outcome may be included in the graphical illustration 802, e.g., using any of the visual indicators described herein. As should be apparent, such different types of visual indicators may be specified, for example, by a user preference of the clinician 104 (e.g., a first clinician may wish to see a particularly effective treatment illustrated using a specified color to illustrate the direct end target in the graphical illustration 802, while a second clinician may wish to see such an outcome illustrated by increasing a brightness of the direct end target).

At the operation 1608, the graphical illustration of the first possible outcome of the use of the treatment parameter may be determined, the treatment parameter including one or more of at least one target-related tissue ancestry-correlated binding site; at least one target-related tissue ancestry-correlated binding agent, at least one direct end target, at least one discriminated end target, at least one direct intermediate target, at least one discriminated intermediate target, at least one treatment agent delivery mechanism relative to the at least one target-related tissue ancestry-correlated binding agent, at least one treatment agent, or at least one treatment agent precursor. For example, the dataset view logic 908 and/or the display update logic 912 may determine the graphical illustration 802 including an illustration of a first possible outcome of the use of one or more of a direct end target, a treatment agent, or a target-related tissue ancestry-correlated binding agent, as these or other examples of the operation 1402 may be selected, provided, or otherwise specified, using the fields 804-810, or similar fields.

Figure 17:
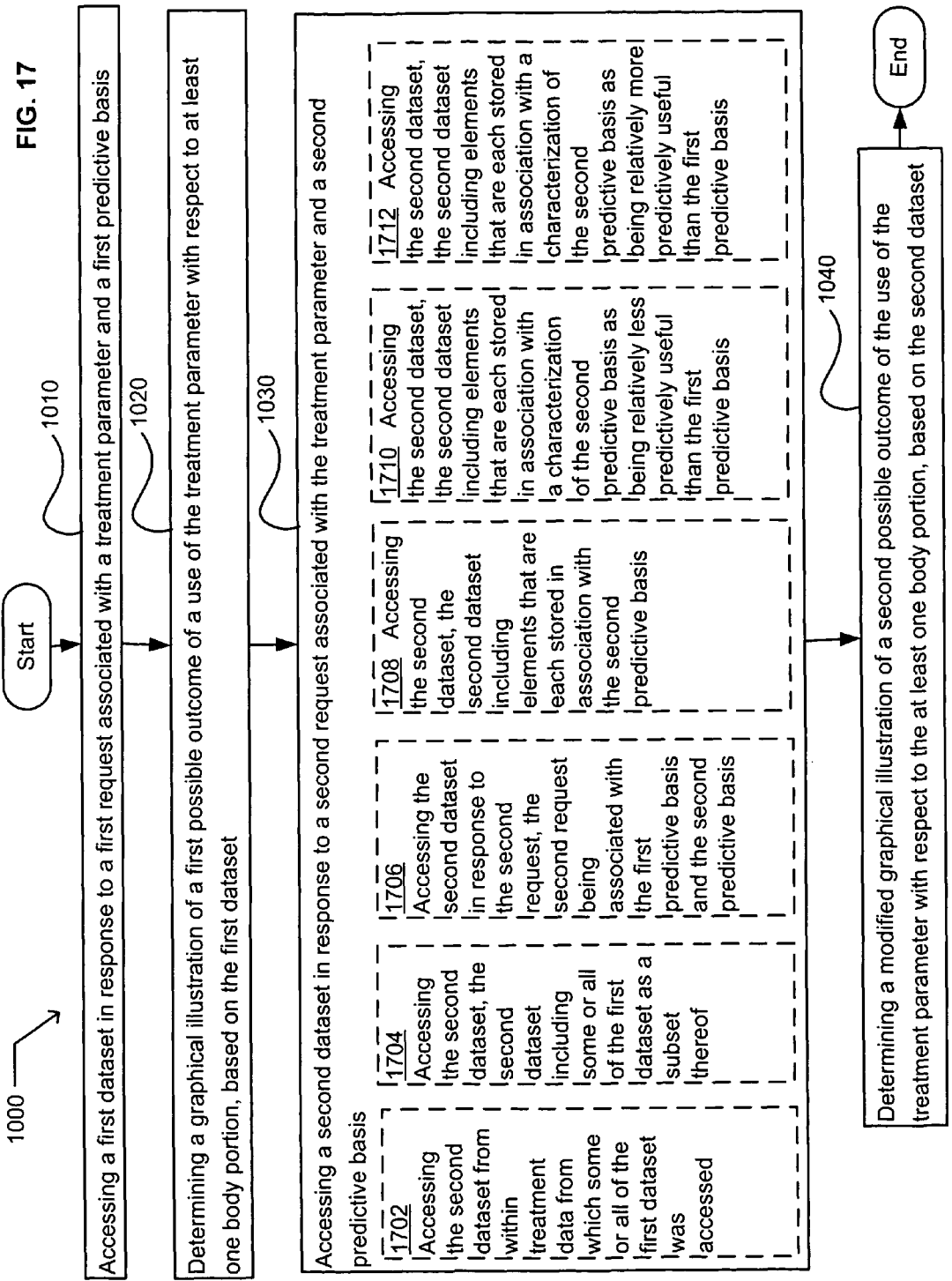
FIG. 17 illustrates an alternative embodiment of the example operational flow of FIG. 10.

FIG. 17 illustrates alternative embodiments of the example operational flow 1000 of FIG. 10. FIG. 17 illustrates example embodiments where the accessing operation 1030 may include at least one additional operation. Additional operations may include operation 1702, operation 1704, operation 1706, operation 1708, operation 1710, and/or operation 1712.

At the operation 1702, the second dataset may be accessed from within treatment data from which some or all of the first dataset was accessed. For example, the dataset view logic 908 may access the second dataset from the treatment data 126, which, as should be apparent from the description herein, also may be the source of the first dataset.

At the operation 1704, the second dataset may be accessed, the second dataset including some or all of the first dataset as a subset thereof. For example, the dataset view logic 908 may access the second dataset including the first dataset (e.g., a dataset associated with "human trials" in the field 812) and another dataset (e.g., a dataset associated with "animal studies" in the field 812), in order to provide a cumulative or combined predictive basis as the second predictive basis. In this way, as described herein, for example, the clinician 104 may expand a prediction of the first possible outcome to include additional data in predicting the second possible outcome.

At the operation 1706, the second dataset may be accessed in response to the second request, the second request being associated with the first predictive basis and the second predictive basis. For example, the dataset view logic 908 may receive the second request from the submission element 902, where the second request may specify both the first predictive basis (e.g., "human trials") and the second predictive basis (e.g., "animal studies") to be accessed from the treatment data 126.

At the operation 1708, the second dataset may be accessed, the second dataset including elements that are each stored in association with the second predictive basis. For example, the dataset view logic 908 may correspond to the second predictive basis of the second request with one or more of the tag(s) 918, 920, which may include, for example, XML tags identifying the second predictive basis and associated with element(s) of the treatment data 126, thereby to identify, and thus access, a plurality of data elements that may then be aggregated into the second dataset.

At the operation 1710, the second dataset may be accessed, the second dataset including elements that are each stored in association with a characterization of the second predictive basis as being relatively less predictively useful than the first predictive basis. For example, a data manager/creator of the treatment data 126, which may include the clinician 104, may make such assignment or association between different predictive bases relative to one another, for later use by the dataset view logic 908 in accessing the second dataset. As described herein, for example, the second dataset associated with "animal studies" may be deemed to be less predictively useful than the first dataset associated with "human studies." In other examples, different types of "human studies" may be included/specified/requested, and may be pre-designated, e.g., using the tags 918, 920, to indicate an assigned level of predictive usefulness, based, for example, on a time, location, or protocol of the studies, or on a preference of the clinician 104, or on some other criteria. In this way, a burden on, or effort of, the clinician 104 may be reduced, while the clinician 104 is allowed, for example, to expand a query as to an efficacy of the treatment parameter by considering datasets being characterized as being relatively less (but still meaningfully) predictively useful.

At the operation 1712, the second dataset may be accessed, the second dataset including elements that are each stored in association with a characterization of the second predictive basis as being relatively more predictively useful than the first predictive basis. For example, and in contrast to the example just given with respect to the operation 1702, the second dataset may include results from "human studies," which may be characterized as being more predictively useful, e.g., in the sense just described.

Figure 18:
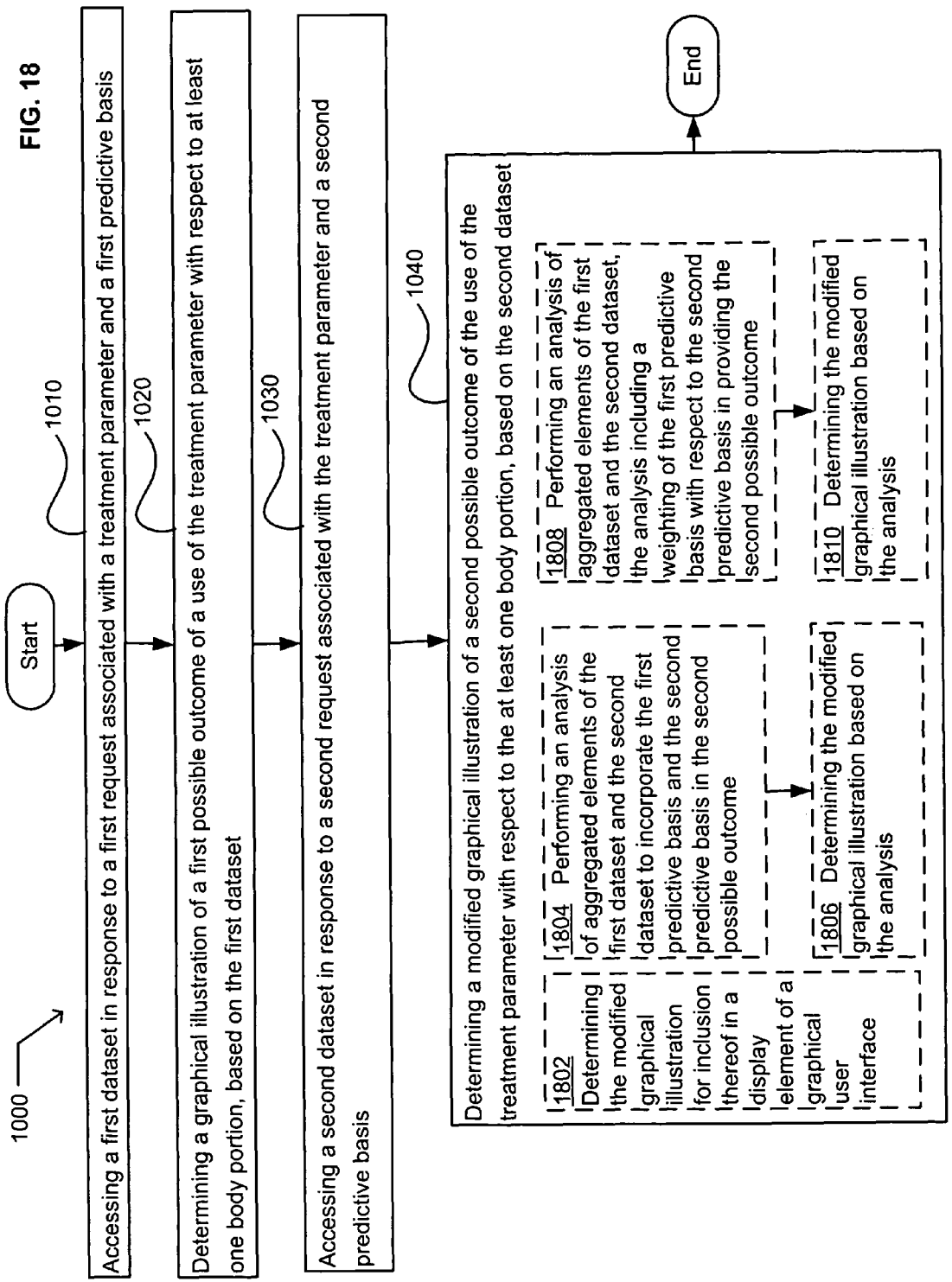
FIG. 18 illustrates an alternative embodiment of the example operational flow of FIG. 10.

FIG. 18 illustrates alternative embodiments of the example operational flow 1000 of FIG. 10. FIG. 18 illustrates example embodiments where the determining operation 1040 may include at least one additional operation. Additional operations may include operation 1802, operation 1804, operation 1806, operation 1808, and/or operation 1810.

At the operation 1802, the modified graphical illustration may be determined for inclusion thereof in a display element of a graphical user interface. For example, the dataset view logic 908 and/or the display update logic 912 may determine the modified graphical illustration to replace the graphical illustration 802, using the display element 904 and using any of the determining operations/techniques described herein, e.g., with respect to the operations 1502-1514, and/or other determining operations/techniques.

At the operation 1804, an analysis of aggregated elements of the first dataset and the second dataset may be performed to incorporate the first predictive basis and the second predictive basis in the second possible outcome. For example, the dataset view logic 908 may perform an analysis of aggregated elements of the first dataset and the second dataset as accessed from the treatment data 126, based on the first request and/or the second dataset, to determine the second possible outcome based thereon. For example, the second request may specify "human trials" and "animal studies" as the first predictive basis and second predictive basis, respectively, so that both human trial-related data elements and animal study-related data elements are aggregated from the treatment data 126 and included in the analysis. Then, at the operation 1806, the modified graphical illustration may be determined based on the analysis. For example, the dataset view logic 908 and/or the display update logic 912 may determine the modified graphical illustration for inclusion in/with the display element 904 based on the analysis, so that the modified graphical illustration illustrates or otherwise conveys or includes a prediction of both the first and second predictive bases in the second possible outcome.

At the operation 1808, an analysis of aggregated elements of the first dataset and the second dataset may be performed, the analysis including a weighting of the first predictive basis with respect to the second predictive basis in providing the second possible outcome. For example, considering a case where the first dataset and the second dataset include datasets for "human trials" and "animal studies," respectively, the dataset view logic 908 may perform the analysis of aggregated elements of the first and second datasets as including a weighting of the two predictive bases relative to one another within the second dataset, e.g., to increase a relative importance of one relative to the other in providing the second predictive basis for the second possible outcome. Then, at the operation 1810, the modified graphical illustration may be determined based on the analysis. For example, the dataset view logic 908 and/or the display update logic 912 may determine the modified graphical illustration for inclusion in/with the display element 904 based on the analysis, so that the modified graphical illustration illustrates or otherwise conveys or includes a prediction of both the first and second predictive bases, as weighted within the analysis, in the second possible outcome.

Figure 19:
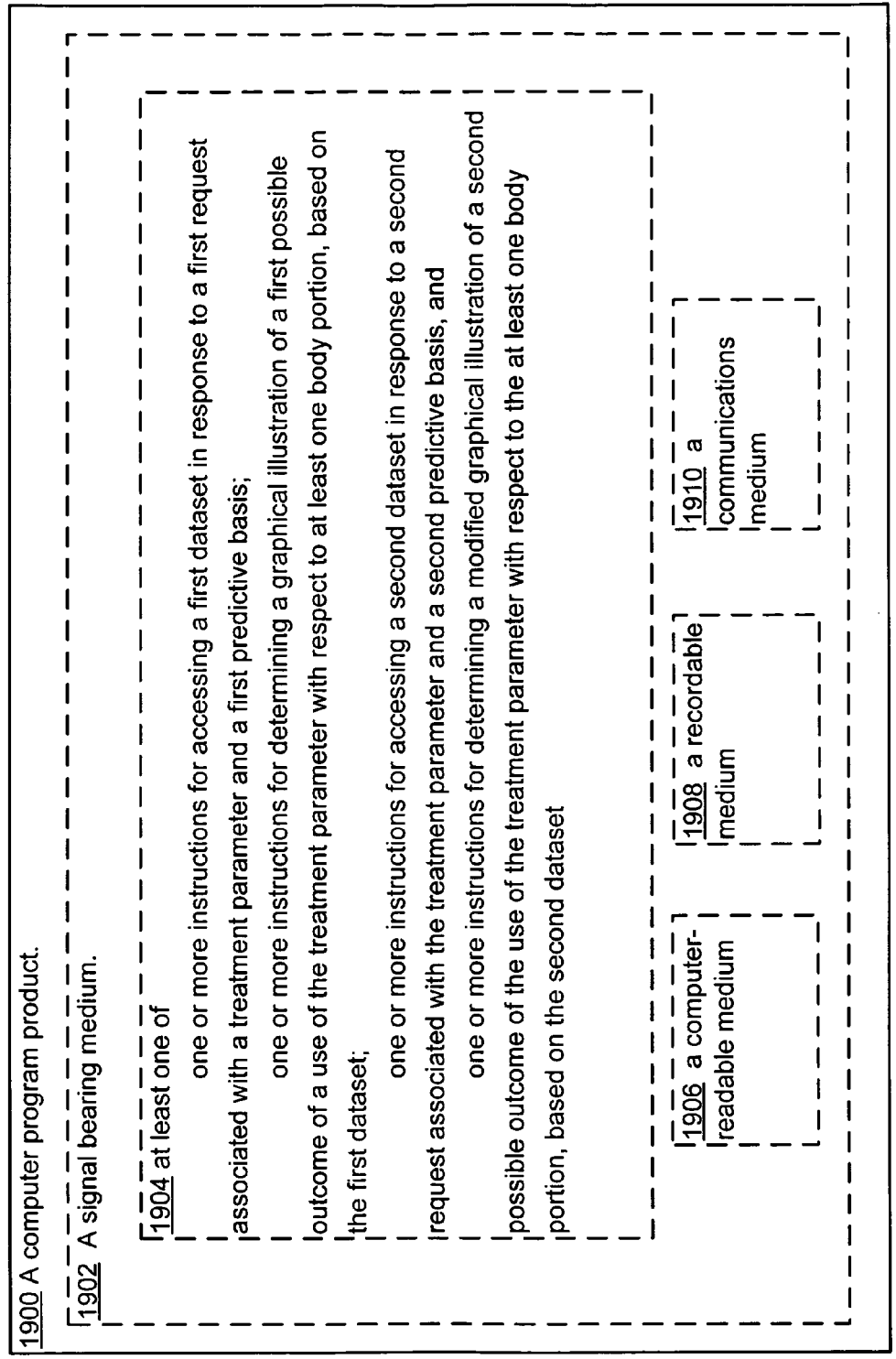
FIG. 19 illustrates a partial view of an example computer program product that includes a computer program for executing a computer process on a computing device.

FIG. 19 illustrates a partial view of an example computer program product 1900 that includes a computer program 1904 for executing a computer process on a computing device. An embodiment of the example computer program product 1900 is provided using a signal bearing medium 1902, and may include at least one of one or more instructions for accessing a first dataset in response to a first request associated with a treatment parameter and a first predictive basis, the signal bearing medium also bearing one or more instructions for determining a graphical illustration of a first possible outcome of a use of the treatment parameter with respect to at least one body portion, based on the first dataset, the signal bearing medium also bearing one or more instructions for accessing a second dataset in response to a second request associated with the treatment parameter and a second predictive basis, and the signal bearing medium also bearing one or more instructions for determining a modified graphical illustration of a second possible outcome of the use of the treatment parameter with respect to the at least one body portion, based on the second dataset. The one or more instructions may be, for example, computer executable and/or logic-implemented instructions. In one implementation, the signal-bearing medium 1902 may include a computer-readable medium 1906. In one implementation, the signal bearing medium 1902 may include a recordable medium 1908. In one implementation, the signal bearing medium 1902 may include a communications medium 1910.

Figure 20:
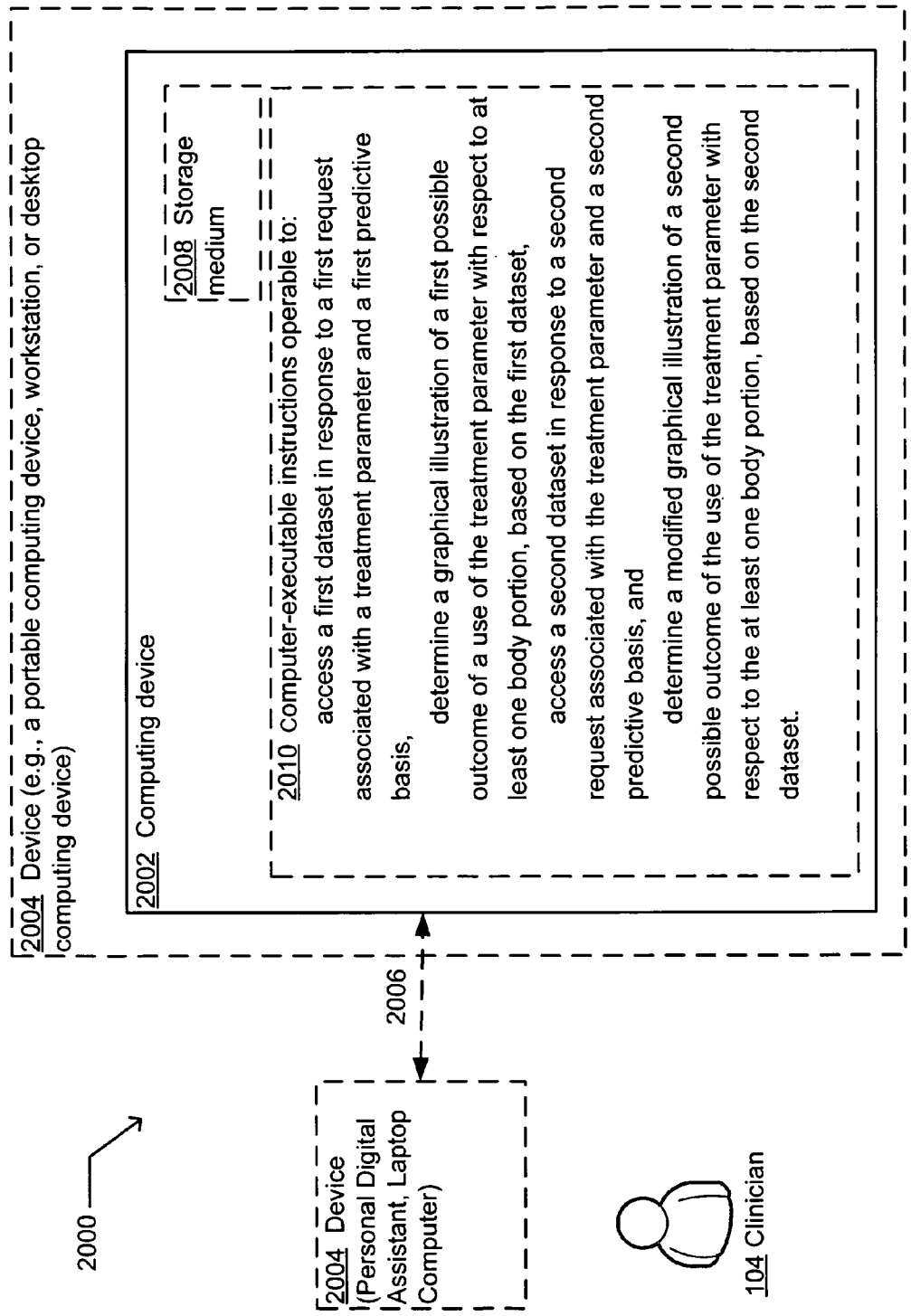
FIG. 20 illustrates an example system in which embodiments may be implemented.

FIG. 20 illustrates an example system 2000 in which embodiments may be implemented. The system 2000 includes a computing system environment. The system 2000 also illustrates the clinician 104 using a device 2004, which is optionally shown as being in communication with a computing device 2002 by way of an optional coupling 2006. The optional coupling 2006 may represent a local, wide-area, or peer-to-peer network, or may represent a bus that is internal to a computing device (e.g., in example embodiments in which the computing device 2002 is contained in whole or in part within the device 2004). A storage medium 2008 may be any computer storage media.

The computing device 2002 includes computer-executable instructions 2010 that when executed on the computing device 2002 cause the computing device 2002 to access a first dataset in response to a first request associated with a treatment parameter and a first predictive basis, determine a graphical illustration of a first possible outcome of a use of the treatment parameter with respect to at least one body portion, based on the first dataset, access a second dataset in response to a second request associated with the treatment parameter and a second predictive basis, and determine a modified graphical illustration of a second possible outcome of the use of the treatment parameter with respect to the at least one body portion, based on the second dataset. As referenced above and as shown in FIG. 20, in some examples, the computing device 2002 may optionally be contained in whole or in part within the clinician device 2004.

In FIG. 20, then, the system 2000 includes at least one computing device (e.g., 2002 and/or 2004). The computer-executable instructions 2010 may be executed on one or more of the at least one computing device. For example, the computing device 2002 may implement the computer-executable instructions 2010 and output a result to (and/or receive data from) the computing (clinician) device 2004. Since the computing device 2002 may be wholly or partially contained within the computing (clinician) device 2004, the computing (clinician) device 2004 also may be said to execute some or all of the computer-executable instructions 2010, in order to be caused to perform or implement, for example, various ones of the techniques described herein, or other techniques.

The clinician device 2004 may include, for example, one or more of a personal digital assistant (PDA), a laptop computer, a tablet personal computer, a networked computer, a computing system comprised of a cluster of processors, a workstation computer, and/or a desktop computer. In another example embodiment, the clinician device 2004 may be operable to communicate with the computing device 2002 to communicate with a database (e.g., implemented using the storage medium 2008) to access the first dataset and/or to access the second dataset.

Figure 21:
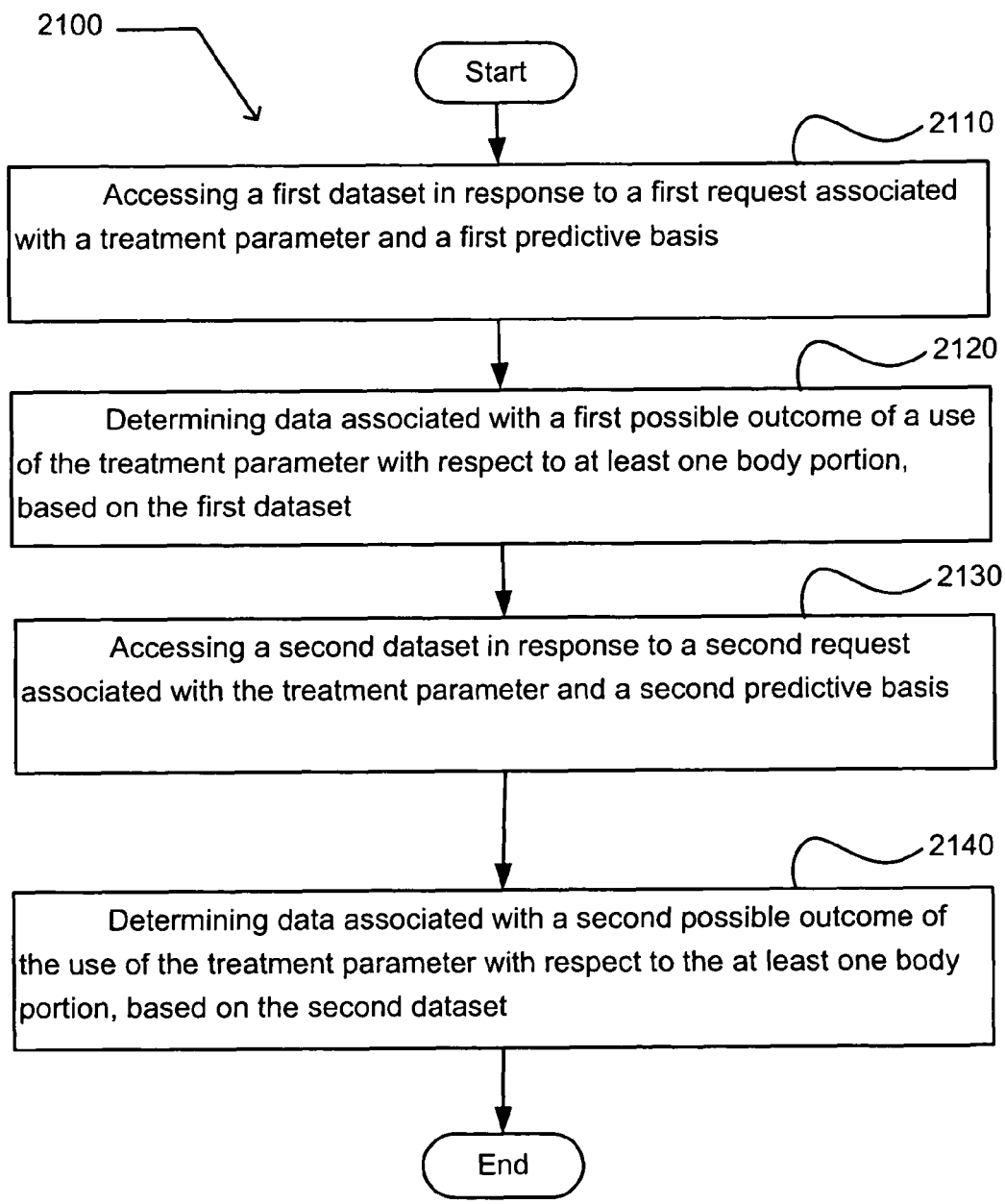
FIG. 21 illustrates an operational flow representing example operations related to accessing predictive data.

FIG. 21 illustrates an alternative operational flow 2100 representing example operations related to accessing predictive data. After a start operation, the operational flow 2100 moves to an accessing operation 2110 where a first dataset may be accessed in response to a first request associated with a first treatment parameter and a first predictive basis. For example, as shown in FIG. 9, a first dataset may be accessed from treatment data 126, in response to a first request received from/through the submission element 902 of the user interface 132, where the submission element 902 may include, for example, one or more of the fields 804-814. For example, the first request, as received at the event handler 906 and forwarded to the dataset view logic 908 within the treatment logic 128, may include a treatment agent "radionuclides" specified in the field 806, as well as a first predictive basis (e.g., "human trials") specified in the field 812. Accordingly, and as described herein (e.g., with reference to FIG. 9), the dataset view logic 908 may thus communicate/interface with the DBMS engine 130 to access the treatment data 126 and obtain the (corresponding) first dataset therefrom.

Then, in a determining operation 2120, data associated with a first possible outcome of a use of the treatment parameter with respect to at least one body portion may be determined, based on the first dataset. For example, the dataset view logic 908 may determine the data associated with the first possible outcome of a use of the treatment agent specified in the field 806 (and included in the first request), based on the first dataset, where the first possible outcome may include, for example, an efficacy of the treatment agent on a direct end target as the at least one body portion (e.g., on "cancer cells in lung," as may be specified in the field 804 and/or included in the first request).

In an accessing operation 2130, a second dataset may be accessed in response to a second request associated with the treatment parameter and a second predictive basis. For example, the dataset view logic 908, as just described, may receive the second request from the event handler 906 and/or the submission element(s) 902, where the second request may include the same treatment parameter (e.g., the treatment agent "radionuclides" specified in the field 806), but a different, or second, predictive basis (e.g., "animal studies," as specified in the field 812). Accordingly, the resulting accessing of the treatment data 126 may result in the accessing of an additional/alternative, or second, dataset therefrom.

Then, in a determining operation 2140, data associated with a second possible outcome of the use of the treatment parameter with respect to the at least one body portion may be determined, based on the second dataset. For example, and continuing the example(s) just given with respect to the operations 2110-2130, the dataset view logic 908 may determine the data associated with the second possible outcome, where the second possible outcome may include, for example, an efficacy of the treatment agent (e.g., "radionuclides") on the at least one body portion (e.g., the direct end target "cancer cells in lung"), as predicted by the second predictive basis (e.g., "animal studies"), based on the second dataset.

Figure 22:
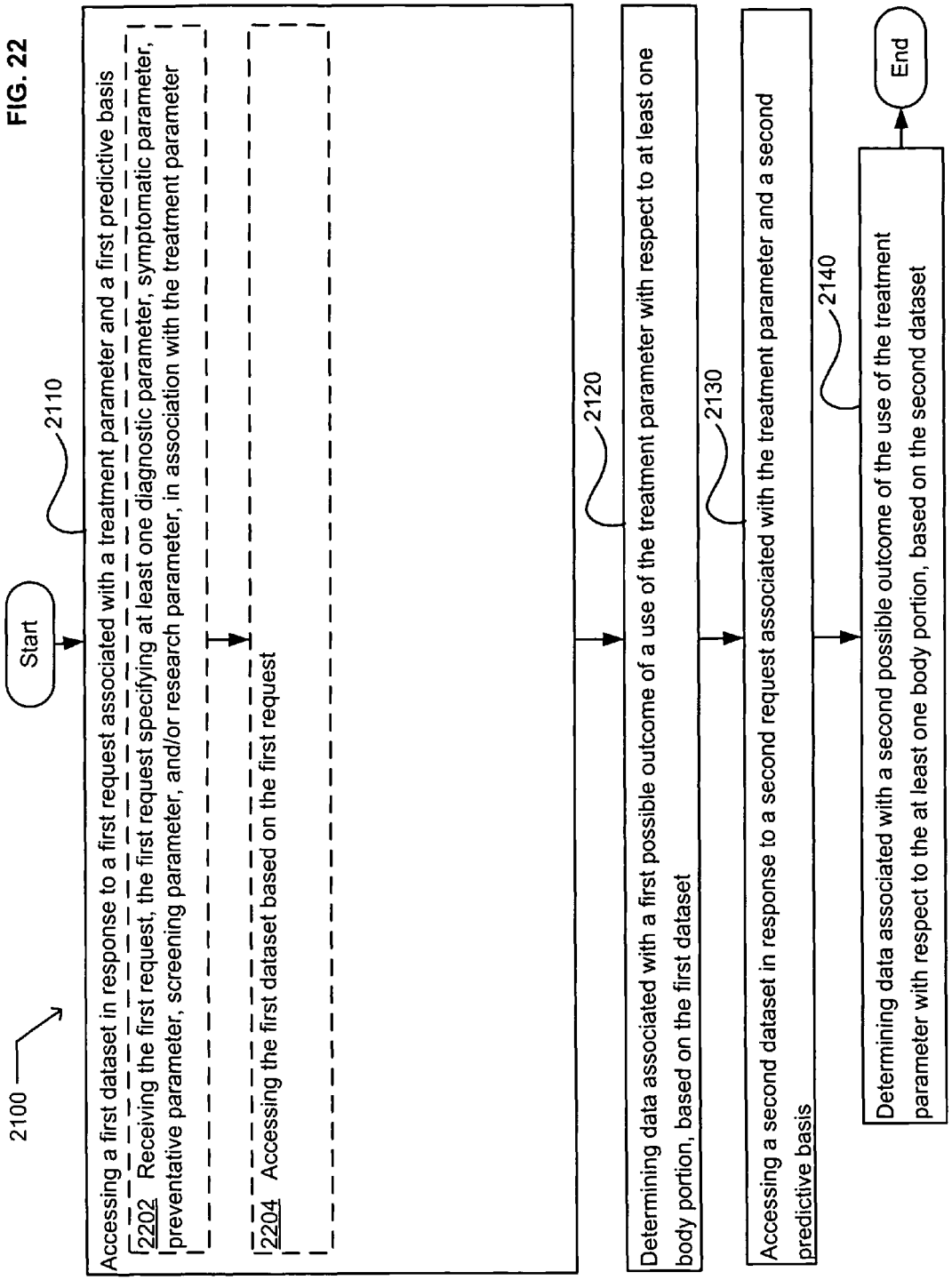
FIG. 22 illustrates an alternative embodiment of the example operational flow of FIG. 21.

FIG. 22 illustrates alternative embodiments of the example operational flow 2100 of FIG. 21. FIG. 22 illustrates example embodiments where the accessing operation 2110 may include at least one additional operation. Additional operations may include an operation 2202.

At the operation 2202, the first request may be received, the first request specifying at least one diagnostic parameter, symptomatic parameter, preventative parameter, screening parameter, and/or research parameter, in association with the treatment parameter. For example, the first request may specify a diagnostic parameter, such as, for example, an inflammation marker, as referenced herein, which may be used as a diagnostic parameter for diagnosing heart disease, and/or as a screening parameter for screening the patient 106 as being at risk for heart disease. Then, at the operation 2204, the first dataset may be accessed, based on the first request. For example, the treatment logic 128, e.g., the dataset view logic 908, may access the first dataset from the treatment data 126, by associating, for example, the diagnostic parameter with the associated treatment parameter. In this way, as described herein, the user interface 132 may require little or no knowledge of specific treatment parameters on the part of the clinician 104, since correlation or other association between the first request and the treatment parameter may occur internally within the treatment system 102.

Figure 23:
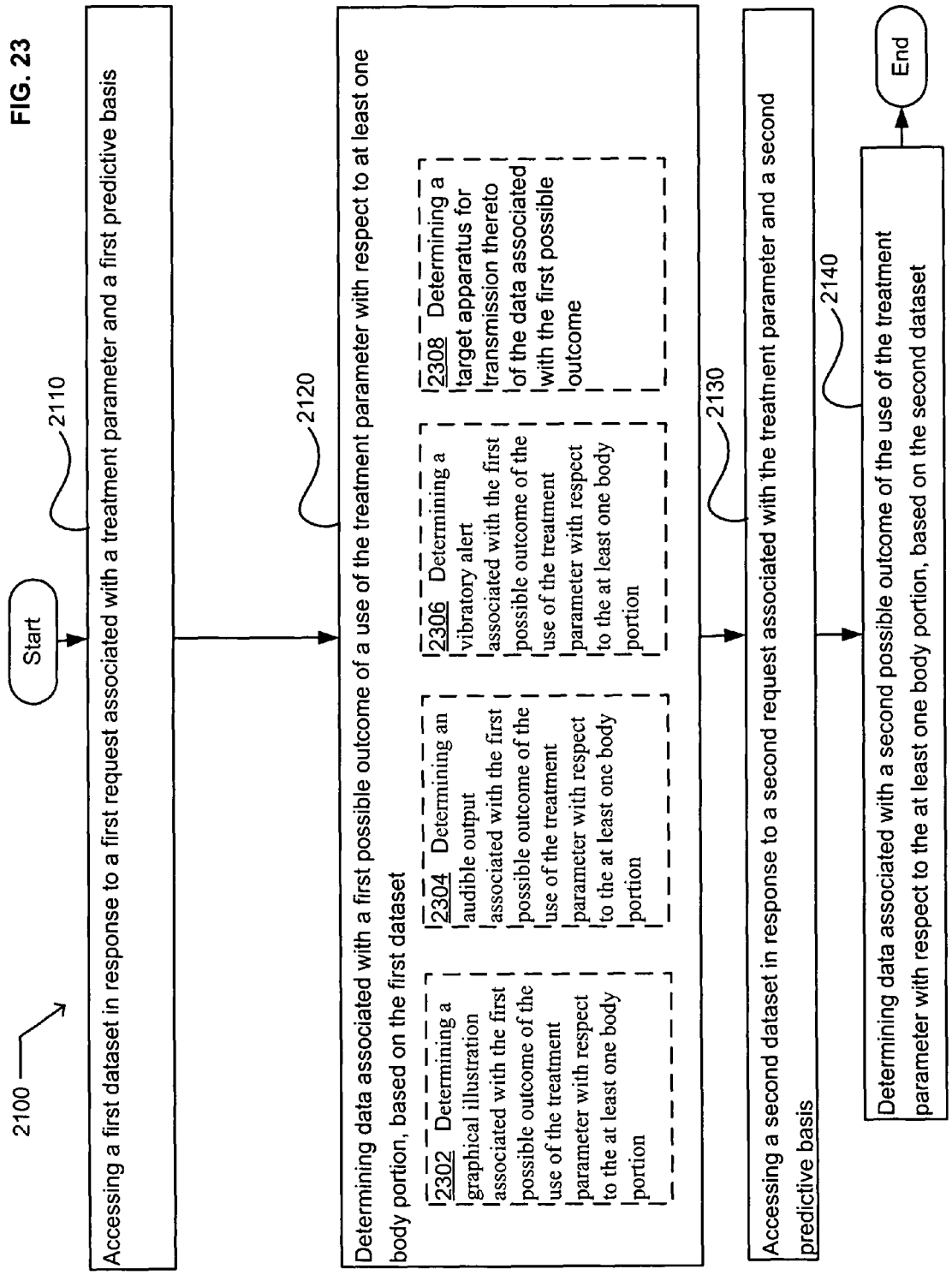
FIG. 23 illustrates an alternative embodiment of the example operational flow of FIG. 21.

FIG. 23 illustrates alternative embodiments of the example operational flow 2100 of FIG. 21. FIG. 23 illustrates example embodiments where the determining operation 2120 may include at least one additional operation. Additional operations may include an operation 2302, an operation 2304, an operation 2306, and/or an operation 2308.

At the operation 2302, a graphical illustration associated with the first possible outcome of the use of the treatment parameter with respect to the at least one body portion may be determined. For example, the dataset view logic 908 may determine, perhaps in conjunction with the display update logic 912, the graphical illustration, e.g., the graphical illustration 802 of at least a portion of a human body. In determining the graphical illustration, the various effects described herein may be employed, e.g., coloring, highlighting, or otherwise visually indicating the at least one body portion in order to indicate or convey the first possible outcome (e.g., a degree of brightness corresponding to a degree of efficacy or risk associated with the treatment agent). As should be apparent, then, the graphical illustration 802 may be provided using the user interface 132, e.g., by updating the display element 904 accordingly.

At the operation 2304, an audible output associated with the first possible outcome of the use of the treatment parameter with respect to the at least one body portion may be determined. For example, the treatment logic 128 may determine a sound to be played over a speaker of the clinician device 134 (see, e.g., FIGS. 1 and/or 2), based on the data associated with the first possible outcome. For example, in a case where a particularly dangerous side effect exists that is associated with the first possible outcome, the clinician device 134 may sound an alarm that notifies the clinician 104 not to proceed with an associated treatment. The audible output may be output in addition to, association with, or alternatively to, the graphical illustration 802.

At the operation 2306, a vibratory alert associated with the first possible outcome of the use of the treatment parameter with respect to the at least one body portion may be determined. For example, again in a case where a particularly dangerous side effect exists that is associated with the first possible outcome, the clinician device 134 may vibrate to notify the clinician 104 not to proceed with an associated treatment. The vibratory alert may be output in addition to, association with, or alternatively to, the graphical illustration 802 and/or the audible output just referenced.

At the operation 2308, a target apparatus for transmission thereto of the data associated with the first possible outcome may be determined. For example, the treatment system 102, or a portion thereof, may be implemented on the data management system 204 of FIG. 2, and may transmit the data associated with the first possible outcome to the clinician device 134, as illustrated in FIG. 2. In this way, for example, a memory or processing power of the clinician device 134 may be conserved.

Figure 24:
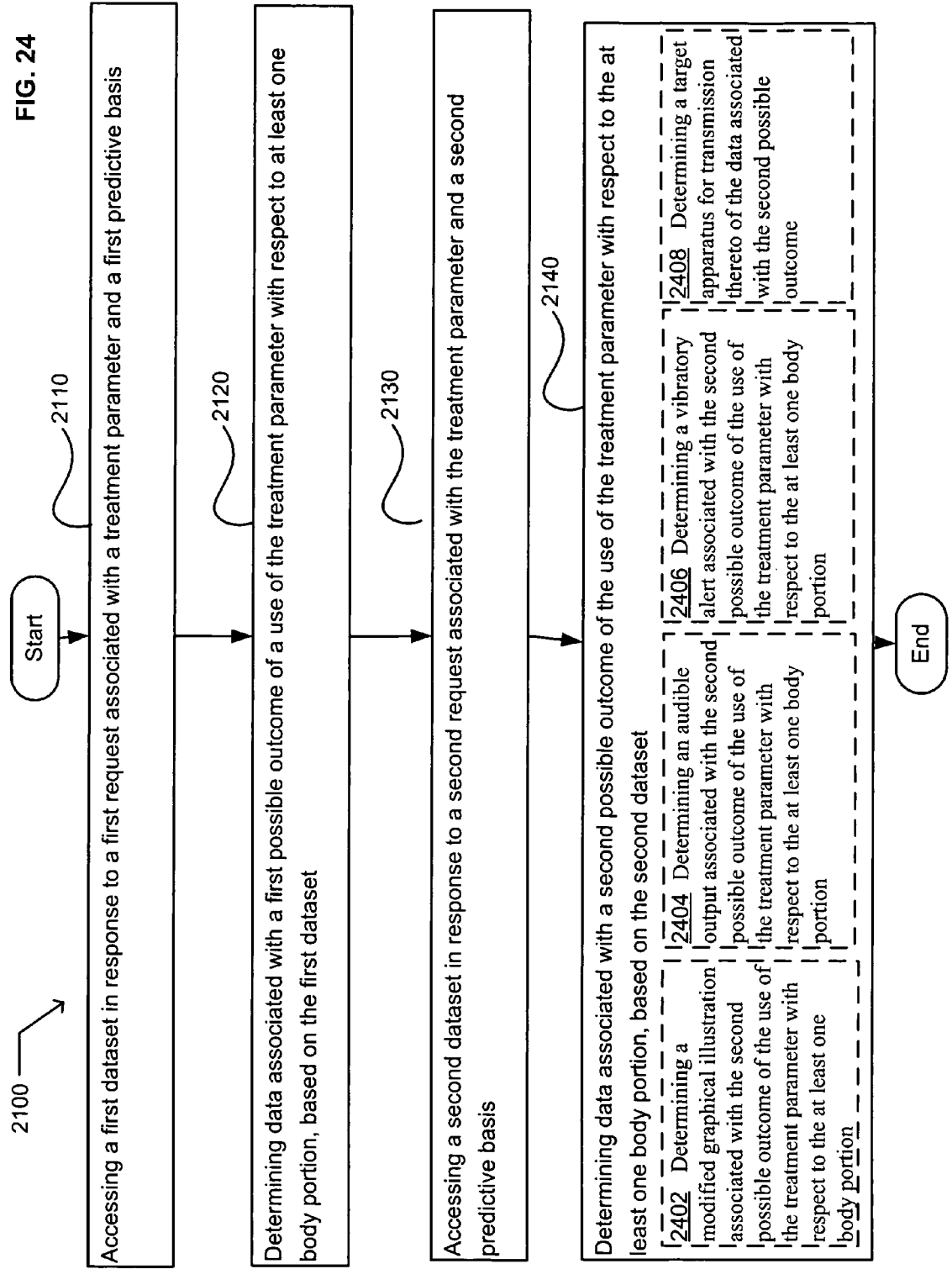
FIG. 24 illustrates an alternative embodiment of the example operational flow of FIG. 21.

FIG. 24 illustrates alternative embodiments of the example operational flow 2100 of FIG. 21. FIG. 24 illustrates example embodiments where the determining operation 2140 may include at least one additional operation. Additional operations may include an operation 2402, an operation 2404, an operation 2406, and/or an operation 2408.

At the operation 2402, a modified graphical illustration associated with the second possible outcome of the use of the treatment parameter with respect to the at least one body portion may be determined. For example, a modified graphical illustration (e.g., a modified version of the graphical illustration 802) may be determined, including a corresponding/modified altering, coloring, or indicating of the at least one body portion.

At the operation 2404, an audible output associated with the second possible outcome of the use of the treatment parameter with respect to the at least one body portion may be determined. For example, the treatment logic 128 may determine a sound to be played over a speaker of the clinician device 134 (see, e.g., FIGS. 1 and/or 2). As should be understood, since the data associated with the second possible outcome may be different from the data associated with the first possible outcome (e.g., may predict a higher or lesser degree of severity of a predicted side effect), the audible output associated with the second possible outcome may be, for example, louder or softer than an audible output associated with the first possible outcome.

At the operation 2406, a vibratory alert associated with the second possible outcome of the use of the treatment parameter with respect to the at least one body portion may be determined. For example, treatment system 102 may cause the clinician device 134 to vibrate to notify the clinician 104 not to proceed with an associated treatment.

At the operation 2408, a target apparatus for transmission thereto of the data associated with the second possible outcome may be determined. For example, as referenced herein, the treatment system 102, or a portion thereof, may be implemented on the data management system 204 of FIG. 2, and may transmit the data associated with the second possible outcome to the clinician device 134, as illustrated in FIG. 2.

Figure 25:
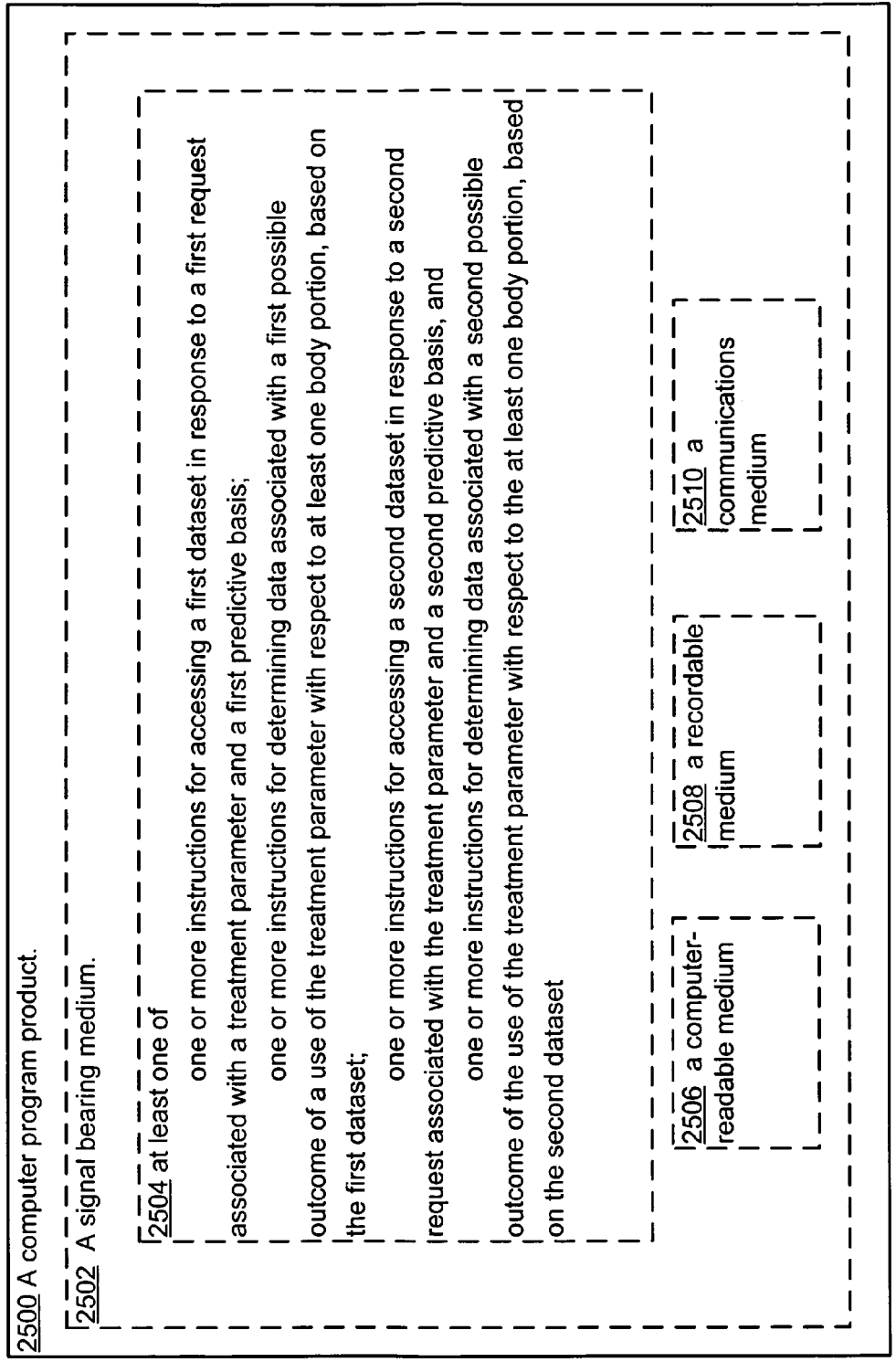
FIG. 25 illustrates a partial view of an example computer program product that includes a computer program for executing a computer process on a computing device.

FIG. 25 illustrates a partial view of an example computer program product 2500 that includes a computer program 2504 for executing a computer process on a computing device. An embodiment of the example computer program product 2500 is provided using a signal bearing medium 2502, and may include at least one of one or more instructions for accessing a first dataset in response to a first request associated with a treatment parameter and a first predictive basis, the signal bearing medium also bearing one or more instructions for determining data associated with a first possible outcome of a use of the treatment parameter with respect to at least one body portion, based on the first dataset, the signal bearing medium also bearing one or more instructions for accessing a second dataset in response to a second request associated with the treatment parameter and a second predictive basis, and the signal bearing medium also bearing one or more instructions for determining data associated with a second possible outcome of the use of the treatment parameter with respect to the at least one body portion, based on the second dataset. The one or more instructions may be, for example, computer executable and/or logic-implemented instructions. In one implementation, the signal-bearing medium 2502 may include a computer-readable medium 2506. In one implementation, the signal bearing medium 2502 may include a recordable medium 2508. In one implementation, the signal bearing medium 2502 may include a communications medium 2510.

Figure 26:
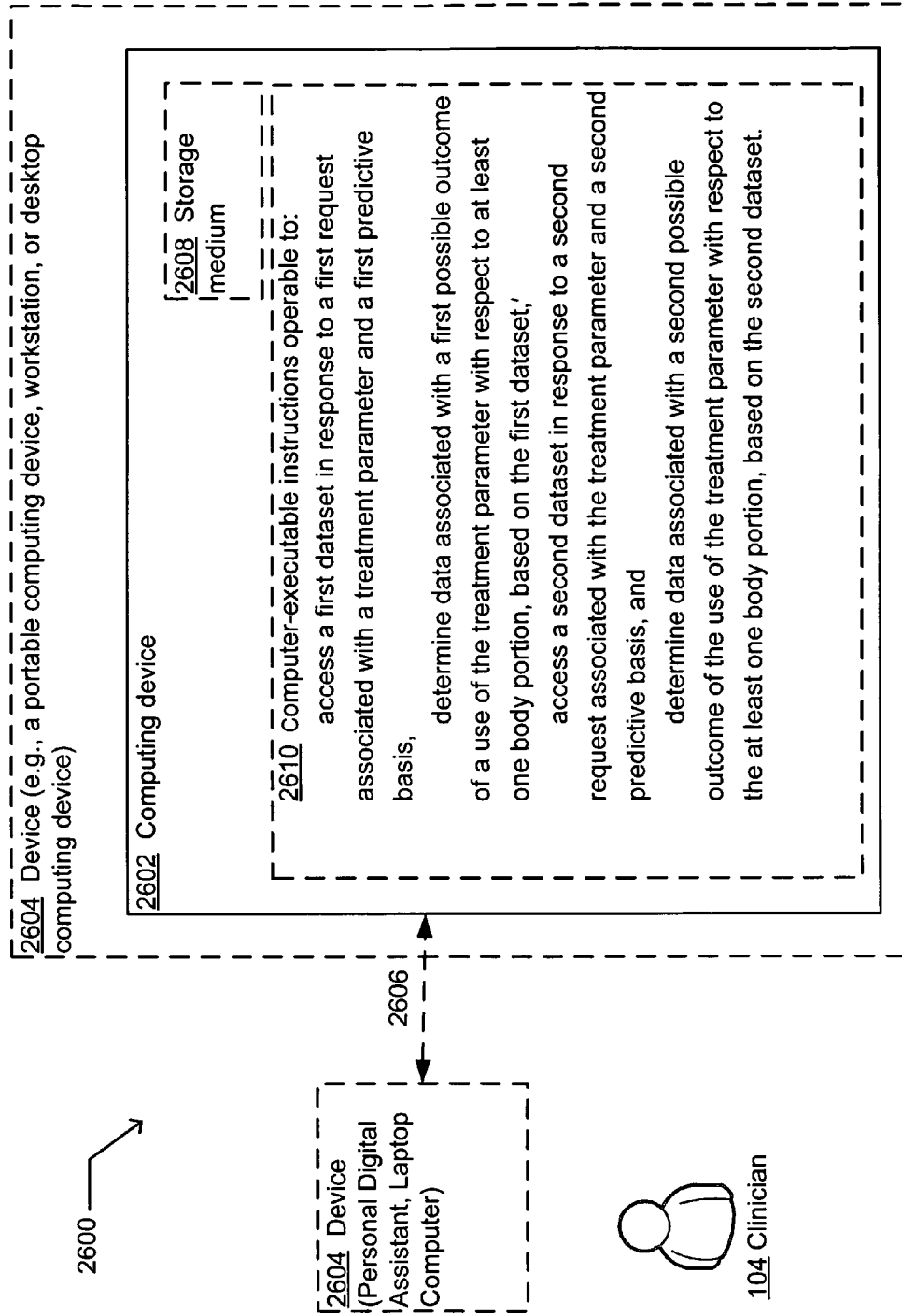
FIG. 26 illustrates an example system in which embodiments may be implemented.

FIG. 26 illustrates an example system 2600 in which embodiments may be implemented. The system 2600 includes a computing system environment. The system 2600 also illustrates the clinician 104 using a device 2604, which is optionally shown as being in communication with a computing device 2602 by way of an optional coupling 2606. The optional coupling 2606 may represent a local, wide-area, or peer-to-peer network, or may represent a bus that is internal to a computing device (e.g., in example embodiments in which the computing device 2602 is contained in whole or in part within the device 2604). A storage medium 2608 may be any computer storage media.

The computing device 2602 includes computer-executable instructions 2610 that when executed on the computing device 2602 cause the computing device 2602 to access a first dataset in response to a first request associated with a treatment parameter and a first predictive basis, determine data associated with a first possible outcome of a use of the treatment parameter with respect to at least one body portion, based on the first dataset, access a second dataset in response to a second request associated with the treatment parameter and a second predictive basis, and determine data associated with a second possible outcome of the use of the treatment parameter with respect to the at least one body portion, based on the second dataset. As referenced above and as shown in FIG. 26, in some examples, the computing device 2602 may optionally be contained in whole or in part within the clinician device 2604.

In FIG. 26, then, the system 2600 includes at least one computing device (e.g., 2602 and/or 2604). The computer-executable instructions 2610 may be executed on one or more of the at least one computing device. For example, the computing device 2602 may implement the computer-executable instructions 2610 and output a result to (and/or receive data from) the computing (clinician) device 2604. Since the computing device 2602 may be wholly or partially contained within the computing (clinician) device 2604, the computing (clinician) device 2604 also may be said to execute some or all of the computer-executable instructions 2610, in order to be caused to perform or implement, for example, various ones of the techniques described herein, or other techniques.

The clinician device 2604 may include, for example, one or more of a personal digital assistant (PDA), a laptop computer, a tablet personal computer, a networked computer, a computing system comprised of a cluster of processors, a workstation computer, and/or a desktop computer. In another example embodiment, the clinician device 2604 may be operable to communicate with the computing device 2602 to communicate with a database (e.g., implemented using the storage medium 2608) to access the first dataset and/or to access the second dataset.

In addition to references described above, the following are also hereby incorporated by reference in their entireties to the extent such are not inconsistent herewith:

Pasqualini et al., "Probing the Structural and Molecular Diversity of Tumor Vasculature," TRENDS in Molecular Medicine, vol. 8, No. 12, pp. 563-571 (December 2002);

Aird et al., "Vascular Bed-specific Expression of an Endothelial Cell Gene is Programmed by the Tissue Microenvironment," The Journal of Cell Biology, vol. 138, No. 5, pp. 1117-1124 (Sep. 8, 1997);

Pasqualini et al., "Organ Targeting In Vivo Using Phage Display Peptide Libraries," Nature, vol. 380, pp. 364-366 (Mar. 28, 1996);

Rajotte et al., "Molecular Heterogeneity of the Vascular Endothelium Revealed by In Vivo Phage Display," J. Clin. Invest., vol. 102, No. 2, pp. 430-437 (July 1998);

M'Rini, et al., "A Novel Endothelial L-Selectin Ligand Activity in Lymph Node Medulla That Is Regulated by (1,3)-Fucosyltransferase-IV," J. Exp. Med., vol. 198, No. 9, pp. 1301-1312 (Nov. 3, 2003);

Carver, et al., "Caveolae: Mining Little Caves for New Cancer Targets," Nature Reviews, vol. 3, pp. 571-572 (August 2003);

Folkman, Judah, "Looking For A Good Endothelial Address," Cancer Cell, pp. 113-115 (March 2002);

Brody, Lawrence C., "Treating Cancer by Targeting a Weakness," N Engl J Med, 353; 9 pp. 949-950 (1 Sep. 2005);

Farmer, et al., "Targeting the DNA Repair Defect in BRCA Mutant Cells as a Therapeutic Strategy," Nature, vol. 434, pp. 917-921 (14 Apr. 2005);

Bryant, et al., "Specific Killing of BRCA2-Deficient Tumours with Inhibitors of poly(ADP-ribose) Polymerase," Nature, vol. 434, pp. 913-917 (14 Apr. 2005);

Hsu, et al., "Neural Systems Responding to Degrees of Uncertainty in Human Decision-Making," Science, vol. 310, pp. 1680-1683 (9 Dec. 2005);

Kaplan, et al., "VEGFR1-Postive Haematopoietic Bone Marrow Progenitors Initiate The Pre-Metastatic Niche," Nature, vol. 438, pp. 820-825 (8 Dec. 2005).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

---

---

What is claimed is:

1. A system comprising:
   circuitry for accessing a first dataset in response to a first request associated with a treatment parameter and a first predictive basis;
   circuitry for determining a graphical illustration of a first possible outcome of a use of the treatment parameter with respect to at least one body portion, based on the first dataset;
   circuitry for accessing a second dataset in response to a second request associated with the treatment parameter and a second predictive basis; and
   circuitry for determining a modified graphical illustration of a second possible outcome of the use of the treatment parameter with respect to the at least one body portion, based on the second dataset.

2. The system of claim 1 wherein accessing a first dataset in response to a first request associated with a treatment parameter and a first predictive basis comprises:
   circuitry for receiving the first request from at least one submission element of a graphical user interface, the first request identifying the treatment parameter and the first predictive basis; and
   circuitry for accessing the first dataset in response to the first request.

3. The system of claim 1 wherein accessing a first dataset in response to a first request associated with a treatment parameter and a first predictive basis comprises:
   circuitry for accessing the first dataset taken from treatment data associated with a plurality of treatment parameters and predictive bases.

4. The system of claim 1 wherein accessing a first dataset in response to a first request associated with a treatment parameter and a first predictive basis comprises:
   circuitry for accessing the first dataset by corresponding the first predictive basis with at least one tag associated with at least one element of the first dataset.

5. The system of claim 1 wherein accessing a first dataset in response to a first request associated with a treatment parameter and a first predictive basis comprises:
   circuitry for accessing the first dataset by structuring a query of a database, based on the treatment parameter and the first predictive basis.

6. The system of claim 1 wherein accessing a first dataset in response to a first request associated with a treatment parameter and a first predictive basis comprises:
   circuitry for accessing the first dataset by corresponding the first predictive basis including at least one actual and/or theoretical analysis of the use of the treatment parameter with at least one element of the first dataset.

7. The system of claim 1 wherein accessing a first dataset in response to a first request associated with a treatment parameter and a first predictive basis comprises:
   circuitry for accessing the first dataset by corresponding the first predictive basis, including one or more of a human study, an animal study, a computer simulation, a speculation, and/or a professionally-informed speculation, with at least one element of the first dataset.

8. The system of claim 1 wherein accessing a first dataset in response to a first request associated with a treatment parameter and a first predictive basis comprises:
   circuitry for accessing the first dataset by corresponding the first predictive basis, including one or more of a human study and/or an animal study, with at least one element of the first dataset.

9. The system of claim 1 wherein accessing a first dataset in response to a first request associated with a treatment parameter and a first predictive basis comprises:
   circuitry for accessing the first dataset by corresponding the first predictive basis, including at least a computer simulation, with at least one element of the first dataset.

10. The system of claim 1 wherein accessing a first dataset in response to a first request associated with a treatment parameter and a first predictive basis comprises:
    circuitry for accessing the first dataset by corresponding the first predictive basis, including at least a speculation and/or a professionally-informed speculation, with at least one element of the first dataset.

11. The system of claim 1 wherein accessing a first dataset in response to a first request associated with a treatment parameter and a first predictive basis comprises:
    circuitry for accessing the first dataset as being associated with the first predictive basis, based on a characterization stored in association with each element of the first dataset and related to one or more of a source of the first dataset, a funding of the first dataset, a procedural aspect of the first dataset, a source of support associated with the first dataset, a research field of the first dataset, a time period or time interval of collection of the first dataset, a professional publication associated with the first dataset, a professional author or investigator associated with the first dataset, or a location of collection of the first dataset.

12. The system of claim 1 wherein accessing a first dataset in response to a first request associated with a treatment parameter and a first predictive basis comprises:
  circuitry for accessing the first dataset as being associated with the first predictive basis, based on a characterization stored in association with each element of the first dataset and related to at least a procedural aspect of the first dataset.

13. The system of claim 1 wherein accessing a first dataset in response to a first request associated with a treatment parameter and a first predictive basis comprises:
  circuitry for accessing the first dataset in response to the first request, the first request specifying the first predictive basis and at least one other predictive basis.

14. The system of claim 1 wherein accessing a first dataset in response to a first request associated with a treatment parameter and a first predictive basis comprises:
  circuitry for receiving the first request, the first request specifying at least one target-related tissue ancestry-correlated binding site as the treatment parameter; and
  circuitry for accessing the first dataset including the at least one target-related tissue ancestry- correlated binding site.

15. The system of claim 1 wherein accessing a first dataset in response to a first request associated with a treatment parameter and a first predictive basis comprises:
  circuitry for receiving the first request, the first request specifying at least one target-related tissue ancestry-correlated binding agent as the treatment parameter; and
  circuitry for accessing the first dataset including the at least one target-related tissue ancestry correlated binding agent.

16. The system of claim 1 wherein accessing a first dataset in response to a first request associated with a treatment parameter and a first predictive basis comprises:
  circuitry for receiving the first request, the first request specifying at least one direct end target as the treatment parameter; and
  circuitry for accessing the first dataset including the at least one direct end target.

17. The system of claim 1 wherein accessing a first dataset in response to a first request associated with a treatment parameter and a first predictive basis comprises:
  circuitry for receiving the first request, the first request specifying at least one discriminated end target as the treatment parameter; and
  circuitry for accessing the first dataset including the at least one discriminated end target.

18. The system of claim 1 wherein accessing a first dataset in response to a first request associated with a treatment parameter and a first predictive basis comprises:
  circuitry for receiving the first request, the first request specifying at least one direct intermediate target as the treatment parameter; and
  circuitry for accessing the first dataset including the at least one direct intermediate target.

19. The system of claim 1 wherein accessing a first dataset in response to a first request associated with a treatment parameter and a first predictive basis comprises:
  circuitry for receiving the first request, the first request specifying at least one discriminated intermediate target as the treatment parameter; and
  circuitry for accessing the first dataset including the at least one discriminated intermediate target.

20. The system of claim 1 wherein accessing a first dataset in response to a first request associated with a treatment parameter and a first predictive basis comprises:
  circuitry for receiving the first request, the first request specifying at least one treatment agent as the treatment parameter; and
  circuitry for accessing the first dataset including the at least one treatment agent.

21. The system of claim 1 wherein accessing a first dataset in response to a first request associated with a treatment parameter and a first predictive basis comprises:
  circuitry for receiving the first request, the first request specifying at least one treatment agent precursor as the treatment parameter; and
  circuitry for accessing the first dataset including the at least one treatment agent precursor.

22. The system of claim 1 wherein determining a graphical illustration of a first possible outcome of a use of the treatment parameter with respect to at least one body portion, based on the first dataset, comprises:
  circuitry for performing an analysis of one or more aggregated elements of the first dataset to determine the first possible outcome of the use of the treatment parameter on the at least one body portion; and
  circuitry for determining the graphical illustration, based on the analysis.

23. The system of claim 1 wherein determining a graphical illustration of a first possible outcome of a use of the treatment parameter with respect to at least one body portion, based on the first dataset, comprises:
  circuitry for performing an analysis of one or more aggregated elements of the first dataset to determine the first possible outcome, the first possible outcome including a desired healing, enhancing, improving, or mitigating effect of the use of the treatment parameter; and
  circuitry for determining the graphical illustration, based on the analysis.

24. The system of claim 1 wherein determining a graphical illustration of a first possible outcome of a use of the treatment parameter with respect to at least one body portion, based on the first dataset, comprises:
  circuitry for performing an analysis of one or more aggregated elements of the first dataset to determine the first possible outcome, the first possible outcome including an undesired risk, side effect, or consequence of the use of the treatment parameter; and
  circuitry for determining the graphical illustration, based on the analysis.

25. The system of claim 1 wherein determining a graphical illustration of a first possible outcome of a use of the treatment parameter with respect to at least one body portion, based on the first dataset, comprises:
  circuitry for determining the graphical illustration including the at least one body portion in association with a visual indicator related to the first possible outcome.

26. The system of claim 1 wherein determining a graphical illustration of a first possible outcome of a use of the treatment parameter with respect to at least one body portion, based on the first dataset, comprises:
  circuitry for determining the graphical illustration including at least one other body portion in association with a visual indicator related to the first possible outcome.

27. The system of claim 1 wherein determining a graphical illustration of a first possible outcome of a use of the treatment parameter with respect to at least one body portion, based on the first dataset, comprises:
  circuitry for determining a correlation between the first possible outcome and a type and/or characteristic of a visual indicator used in the graphical illustration to represent the first possible outcome.

28. The system of claim 1 wherein accessing a second dataset in response to a second request associated with the treatment parameter and a second predictive basis comprises:
 circuitry for accessing the second dataset from within treatment data from which some or all of the first dataset was accessed.

29. The system of claim 1 wherein accessing a second dataset in response to a second request associated with the treatment parameter and a second predictive basis comprises:
 circuitry for accessing the second dataset, the second dataset including some or all of the first dataset as a subset thereof.

30. The system of claim 1 wherein accessing a second dataset in response to a second request associated with the treatment parameter and a second predictive basis comprises:
 circuitry for accessing the second dataset in response to the second request, the second request being associated with the first predictive basis and the second predictive basis.

31. The system of claim 1 wherein accessing a second dataset in response to a second request associated with the treatment parameter and a second predictive basis comprises:
 circuitry for accessing the second dataset, the second dataset including elements that are each stored in association with the second predictive basis.

32. The system of claim 1 wherein accessing a second dataset in response to a second request associated with the treatment parameter and a second predictive basis comprises:
 circuitry for accessing the second dataset, the second dataset including elements that are each stored in association with a characterization of the second predictive basis as being relatively less predictively useful than the first predictive basis.

33. The system of claim 1 wherein accessing a second dataset in response to a second request associated with the treatment parameter and a second predictive basis comprises:
 circuitry for accessing the second dataset, the second dataset including elements that are each stored in association with a characterization of the second predictive basis as being relatively more predictively useful than the first predictive basis.

34. The system of claim 1 wherein determining a modified graphical illustration of a second possible outcome of the use of the treatment parameter with respect to the at least one body portion, based on the second dataset, comprises:
 circuitry for performing an analysis of aggregated elements of the first dataset and the second dataset to incorporate the first predictive basis and the second predictive basis in the second possible outcome; and
 circuitry for determining the modified graphical illustration based on the analysis.

35. The system of claim 1 wherein determining a modified graphical illustration of a second possible outcome of the use of the treatment parameter with respect to the at least one body portion, based on the second dataset, comprises:
 circuitry for performing an analysis of aggregated elements of the first dataset and the second dataset, the analysis including a weighting of the first predictive basis with respect to the second predictive basis in providing the second possible outcome; and
 circuitry for determining the modified graphical illustration based on the analysis.

36. A computer program product comprising:
 a non-transitory signal-bearing medium bearing at least one of
 (a) one or more instructions for accessing a first dataset in response to a first request associated with a treatment parameter and a first predictive basis,
 (b) one or more instructions for determining a graphical illustration of a first possible outcome of a use of the treatment parameter with respect to at least one body portion, based on the first dataset,
 (c) one or more instructions for accessing a second dataset in response to a second request associated with the treatment parameter and a second predictive basis, and
 (d) one or more instructions for determining a modified graphical illustration of a second possible outcome of the use of the treatment parameter with respect to the at least one body portion, based on the second dataset.

37. A system comprising:
a computing device; and
instructions that when executed on the computing device cause the computing device to
 (a) access a first dataset in response to a first request associated with a treatment parameter and a first predictive basis,
 (b) determine a graphical illustration of a first possible outcome of a use of the treatment parameter with respect to at least one body portion, based on the first dataset,
 (c) access a second dataset in response to a second request associated with the treatment parameter and a second predictive basis, and
 (d) determine a modified graphical illustration of a second possible outcome of the use of the treatment parameter with respect to the at least one body portion, based on the second dataset.

38. A method comprising:
accessing, using a microprocessor, a first dataset in response to a first request associated with a treatment parameter and a first predictive basis;
determining, using a microprocessor, a graphical illustration of a first possible outcome of a use of the treatment parameter with respect to at least one body portion, based on the first dataset;
accessing, using a microprocessor, a second dataset in response to a second request associated with the treatment parameter and a second predictive basis; and
determining, using a microprocessor, a modified graphical illustration of a second possible outcome of the use of the treatment parameter with respect to the at least one body portion, based on the second dataset.

39. A computer program product comprising:
a non-transitory signal-bearing medium bearing at least one of
 (a) one or more instructions for accessing a first dataset in response to a first request associated with a treatment parameter and a first predictive basis,
 (b) one or more instructions for determining data associated with a first possible outcome of a use of the treatment parameter with respect to at least one body portion, based on the first dataset,
 (c) one or more instructions for accessing a second dataset in response to a second request associated with the treatment parameter and a second predictive basis, and
 (d) one or more instructions for determining data associated with a second possible outcome of the use of the treatment parameter with respect to the at least one body portion, based on the second dataset.

40. A system comprising:
a computing device; and
instructions that when executed on the computing device cause the computing device to
 (a) access a first dataset in response to a first request associated with a treatment parameter and a first predictive basis, (b) determine data associated with a first possible outcome of a use of the treatment parameter with respect to at least one body portion, based on the first dataset,
(c) access a second dataset in response to a second request associated with the treatment parameter and a second predictive basis, and (d) determine data associated with a second possible outcome of the use of the treatment parameter with respect to the at least one body portion, based on the second dataset.

* * * * *